(12) United States Patent
Takabatake et al.

(10) Patent No.: US 10,675,415 B2
(45) Date of Patent: Jun. 9, 2020

(54) PHARMACEUTICAL SYRINGE UNIT, PHARMACEUTICAL INJECTION DEVICE EQUIPPED WITH SAID UNIT, INJECTION NEEDLE ATTACHMENT AND REMOVAL FIXTURE, AND STORAGE CASE

(71) Applicant: PHC Holdings Corporation, Minato-ku, Tokyo (JP)

(72) Inventors: Yukihiro Takabatake, Ehime (JP); Toshiaki Iio, Ehime (JP); Seiji Kikuchi, Ehime (JP); Yutaro Fujino, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 597 days.

(21) Appl. No.: 15/504,008

(22) PCT Filed: Sep. 25, 2015

(86) PCT No.: PCT/JP2015/077104
§ 371 (c)(1),
(2) Date: Feb. 14, 2017

(87) PCT Pub. No.: WO2016/052332
PCT Pub. Date: Apr. 7, 2016

(65) Prior Publication Data
US 2017/0274150 A1 Sep. 28, 2017

(30) Foreign Application Priority Data

Sep. 30, 2014 (JP) .................................. 2014-199834
Jan. 14, 2015 (JP) .................................. 2015-005220

(51) Int. Cl.
*A61M 5/32* (2006.01)
*A61M 5/20* (2006.01)
(Continued)

(52) U.S. Cl.
CPC .......... *A61M 5/3202* (2013.01); *A61M 5/002* (2013.01); *A61M 5/14546* (2013.01);
(Continued)

(58) Field of Classification Search
CPC .............. A61M 5/3202; A61M 5/3271; A61M 25/0631; A61M 5/14546; A61M 5/31505; A61M 5/31515
See application file for complete search history.

(56) References Cited

U.S. PATENT DOCUMENTS 5,092,842 A 3/1992 Bechtold et al.
6,544,234 B1 4/2003 Gabriel
(Continued)

FOREIGN PATENT DOCUMENTS

EP 2253348 A1 11/2010
EP 2357013 A1 8/2011
(Continued)

OTHER PUBLICATIONS

The International Search Report of Int'l Appln. No. PCT/JP2015/075633 dated Oct. 20, 2015.
(Continued)

*Primary Examiner* — Rebecca E Eisenberg
*Assistant Examiner* — Tasnim Mehjabin Ahmed
(74) *Attorney, Agent, or Firm* — Wenderoth, Lind & Ponack, L.L.P.

(57) ABSTRACT

A pharmaceutical syringe unit is configured to be mounted to a pharmaceutical injection device main body and hold a pharmaceutical-filled pharmaceutical syringe, in order to mount the pharmaceutical syringe to a pharmaceutical injection device, wherein a syringe cover is configured to slide forward and backward with respect to a distal end cap by operation of the pharmaceutical injection device main body, thereby allowing movement between a needle insertion
(Continued)

position at which insertion of an injection needle into a target is to be completed, and a needle withdrawal position at which withdrawal of the injection needle from the target is to be completed, and a guide component is configured to guide the syringe cover over a range that is greater than a distance between the needle insertion position and the needle withdrawal position.

20 Claims, 41 Drawing Sheets

(51) Int. Cl.
| | | |
|---|---|---|
| *A61M 5/24* | (2006.01) | |
| *A61M 5/00* | (2006.01) | |
| *A61M 5/145* | (2006.01) | |
| *A61M 5/315* | (2006.01) | |
| *A61M 5/34* | (2006.01) | |
| *A61M 5/36* | (2006.01) | |
| *A61M 5/31* | (2006.01) | |

(52) U.S. Cl.
CPC ............... *A61M 5/20* (2013.01); *A61M 5/24* (2013.01); *A61M 5/31505* (2013.01); *A61M 5/31515* (2013.01); *A61M 5/3205* (2013.01); *A61M 5/347* (2013.01); *A61M 5/36* (2013.01); *A61M 2005/206* (2013.01); *A61M 2005/3142* (2013.01); *A61M 2005/31588* (2013.01); *A61M 2005/3206* (2013.01); *A61M 2205/3306* (2013.01); *A61M 2205/52* (2013.01); *A61M 2205/581* (2013.01); *A61M 2205/582* (2013.01); *A61M 2205/8206* (2013.01)

(56) References Cited

U.S. PATENT DOCUMENTS

| | | |
|---|---|---|
| 8,398,602 B2 | 3/2013 | Iio et al. |
| 8,674,656 B2 | 3/2014 | Iio et al. |
| 2005/0197650 A1 | 9/2005 | Sugimoto et al. |
| 2007/0078408 A1 | 4/2007 | Wang |
| 2009/0043265 A1* | 2/2009 | Schneider ............... A61M 5/20 604/218 |
| 2010/0292643 A1 | 11/2010 | Wilmot et al. |
| 2011/0004165 A1* | 1/2011 | Iio ........................... A61M 5/20 604/197 |
| 2011/0218502 A1 | 9/2011 | Iio et al. |
| 2013/0172819 A1 | 7/2013 | Iio et al. |
| 2013/0175192 A1 | 7/2013 | Iio et al. |
| 2013/0274677 A1 | 10/2013 | Ekman et al. |
| 2014/0207106 A1 | 7/2014 | Bechmann et al. |
| 2014/0330215 A1 | 11/2014 | Kikuchi et al. |

FOREIGN PATENT DOCUMENTS

| | | |
|---|---|---|
| JP | H02-502971 A | 9/1990 |
| JP | 2005-245852 A | 9/2005 |
| JP | 2007-111301 A | 5/2007 |
| JP | 2010-035925 A | 2/2010 |
| JP | 2014-502888 A | 2/2014 |
| JP | 2014-111173 A | 6/2014 |
| JP | 2014-526297 A | 10/2014 |
| WO | 00/41754 A1 | 7/2000 |
| WO | 2009/125582 A1 | 10/2009 |
| WO | 2010/000559 A1 | 1/2010 |
| WO | 2012/064258 A1 | 5/2012 |
| WO | 2012/066767 A1 | 5/2012 |
| WO | 2013/084505 A1 | 6/2013 |
| WO | 2014/049924 A1 | 4/2014 |

OTHER PUBLICATIONS

The International Search Report of Int'l Appln. No. PCT/JP2015/077104 dated Dec. 15, 2015.
The Search Report from the relevant European Patent Application No. 15845876.0 dated Oct. 5, 2017.
The Search Report from the corresponding European Patent Application No. 15847515.2 dated Oct. 17, 2017.

* cited by examiner

PHARMACEUTICAL SYRINGE UNIT, PHARMACEUTICAL INJECTION DEVICE EQUIPPED WITH SAID UNIT, INJECTION NEEDLE ATTACHMENT AND REMOVAL FIXTURE, AND STORAGE CASE

PRIORITY

This is a National Stage application under 35 U.S.C. § 365 of International Application PCT/JP2015/077104, with an international filing date of Sep. 25, 2015, which claims priority to Japanese Patent Application No. 2014-199834 filed on Sep. 30, 2014 and Japanese Patent Application No. 2015-005220 filed on Jan. 14, 2015. The entire disclosures of International Application PCT/JP2015/077104, Japanese Patent Application No. 2014-199834 and Japanese Patent Application No. 2015-005220 are hereby incorporated by reference.

TECHNICAL FIELD

Certain implementations of the present invention relate to a pharmaceutical syringe unit having a needle mounting component for mounting an injection needle, and to a pharmaceutical injection device equipped with this unit, to an injection needle attachment and removal fixture for replacing the injection needle of the pharmaceutical syringe unit, and to a storage case equipped with this fixture.

BACKGROUND

A pharmaceutical syringe that contains a growth hormone, for example, is mounted to a pharmaceutical injection device in a state of being mounted to a syringe cover. Then, a distal end cap is mounted around the outside of the syringe cover, after which an injection needle for injecting a pharmaceutical is mounted from the distal end side of the distal end cap. Then, the air is expelled as needed, and when this is finished, the pharmaceutical is injected by the pharmaceutical injection device into the patient's body.

The injection operation with a pharmaceutical injection device such as this is summarized below.

When he distal end side of the pharmaceutical injection device is placed against the injection site on the body (at this point the distal end side of the distal end cap will be touching the skin) and the inject button is pressed, from there on the pharmaceutical injection device performs a series of injection operations automatically.

That is, first a needle insertion operation is performed to insert the needle into the body, after which a specific amount of the pharmaceutical is injected into the body, and when the pharmaceutical injection is complete, a needle withdrawal operation is performed to withdraw the needle from the body, and this completes the series of injection operations.

After this pharmaceutical injection operation has been completed, the user removes the injection needle that had been mounted to the distal end side of the distal end cap (at this point a needle case, which is a protective cover for the injection needle that had been removed before injection, is reattached), after which the distal end cap is removed from the pharmaceutical injection device, and then the pharmaceutical syringe is removed from the syringe cover, and the pharmaceutical syringe is stored as needed in a refrigerator or other cool place.

SUMMARY

Sometimes, when a pharmaceutical is to be injected, the user first mounts the pharmaceutical syringe to the inside of the syringe cover, then mounts the syringe cover (to which this pharmaceutical syringe has been mounted) to the pharmaceutical injection device main body. After this the user mounts the distal end cap to the outer periphery of the syringe cover, and then mounts an injection needle for injecting the pharmaceutical from the distal end side of the distal end cap. Then, the air is expelled as needed, and when this is finished the pharmaceutical can be injected.

That is, to perform the injection of a pharmaceutical using a pharmaceutical syringe, each time the user has to go through the above series of jobs (mounting the pharmaceutical syringe to the inside of the syringe cover, then mounting the syringe cover with its attached pharmaceutical syringe to the pharmaceutical injection device, and then mounting the distal end cap around the outside of the syringe cover), after which the job of mounting the injection needle to the distal end side is performed.

At this point a needle case (protective cover) or the like needs to be removed after attaching the needle to the needle mounting component of the syringe cover located inside the distal end cap through the distal end opening in the distal end cap in the state of a needle unit that includes an injection needle. Since the injection needle has to be mounted or removed through the distal end opening, the mounting of the injection needle entailed some difficult work.

Also, after the pharmaceutical injection, the injection needle is removed from the distal end side of the distal end cap, and this entails the job of attaching the needle case of the injection needle from the distal end side of the injection needle, but this was difficult because it was performed on an injection needle that was mounted to the needle mounting component, which is in the interior of the distal end opening of the distal end cap.

Thus, when the injection needle is mounted or removed, this has to be done through the distal end opening in the distal end cap, and while the job is made somewhat easier by modifying the shape of the distal end opening, the job of removing the injection needle has room for improvement.

In view of this, it is an object of certain implementations of the present invention to provide a pharmaceutical syringe unit with which it is easier to mount and remove the injection needle, as well as a pharmaceutical injection device equipped with this unit, an injection needle attachment and removal fixture, and a storage case equipped with this fixture.

To achieve the stated object, certain implementations of the pharmaceutical syringe unit of the present invention are pharmaceutical syringe units that hold a pharmaceutical syringe and is mounted to a pharmaceutical injection device main body in order to mount a pharmaceutical-filled syringe to a pharmaceutical injection device, said units comprising a distal end cap and a syringe cover. The distal end cap has openings on the front end side and the rear end side. The syringe cover is held in a state of being able to slide in the forward and backward direction with respect to the distal end cap. The distal end cap has a guide component, and a first engagement component. The guide component guides the sliding of the syringe cover forward and backward. The first engagement component can be engaged with the pharmaceutical injection device main body. The syringe cover has on the front end portion a needle mounting component used to mount an injection needle for injecting the pharmaceutical. The syringe cover is slid in the forward and backward direction with respect to the distal end cap by the operation of the pharmaceutical injection device main body, and is able to move between a needle insertion position at which the operation of inserting the injection needle into the target is completed, and a needle withdrawal position at which the operation of withdrawing the injection needle from the target is completed. The range over which the syringe cover can be slid by the guide component is greater than the distance between the needle insertion position and the needle withdrawal position.

Specifically, because the sliding range of the syringe cover within the distal end cap is greater than the distance between the needle insertion position and needle withdrawal position of the pharmaceutical injection device, when the injection needle is mounted or removed, the large-diameter part, which is farther away from the center axis of the injection needle, can be exposed from the distal end opening of the distal end cap, and makes it extremely easy to mount or remove the needle case (protective cover), and makes the job of mounting and removing the injection needle extremely easy.

Certain implementations provide a pharmaceutical syringe unit with which it is easier to mount and remove the injection needle, as well as a pharmaceutical injection device equipped with this unit, an injection needle attachment and removal fixture, and a storage case equipped with this fixture.

DETAILED DESCRIPTION

Certain implementations of the present invention will now be described through reference to the drawings.

Embodiment 1

1. Overview of Pharmaceutical Injection Device

Figure 1:
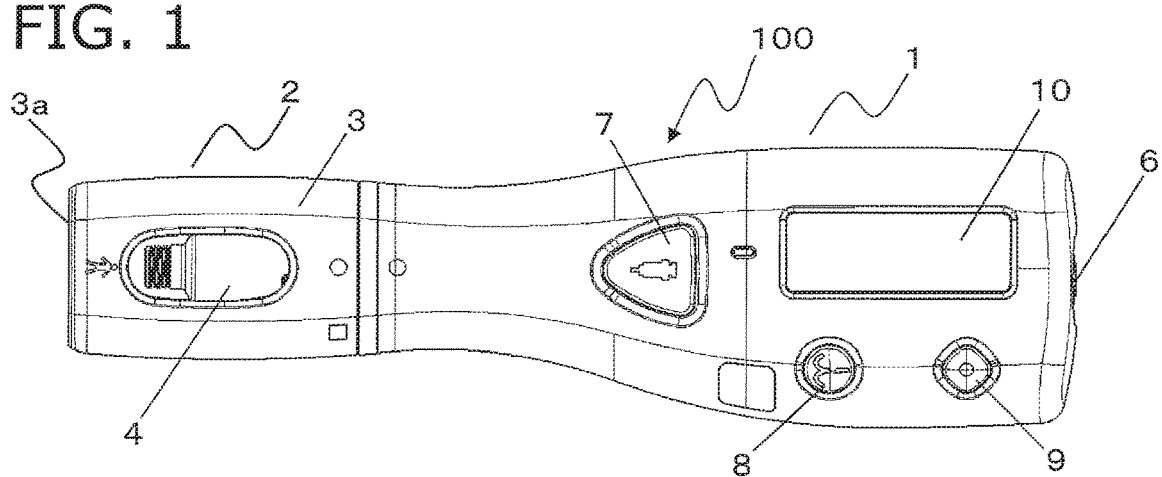
FIG. 1 is a front view of the pharmaceutical injection device in Embodiment 1 pertaining to the present invention.

FIG. 1 is a front view of the pharmaceutical injection device in Embodiment 1 pertaining to the present invention. As shown in FIG. 1, the pharmaceutical injection device in this embodiment comprises a pharmaceutical injection device main body 100 and a pharmaceutical syringe unit 2. The pharmaceutical syringe unit 2 is configured so as to be removably mounted on the distal end side (also called the front end side; in FIG. 1, the left side) of the main body case 1 of the pharmaceutical injection device main body 100.

More specifically, the pharmaceutical syringe unit 2 has a cylindrical distal end cap 3 having openings at both ends, and a cylindrical syringe cover 4 that is disposed in the interior of this distal end cap 3. The openings at the both ends of the pharmaceutical syringe unit 2 are the distal end opening 3c and the rear end opening 3e shown in FIG. 2 (discussed below).

Also, the distal end cap 3 serves to restrict the injection position and depth when the distal end face 3a side makes contact with the skin when a pharmaceutical is injected into the body.

The syringe cover 4 attached in the interior of the distal end cap 3 also has openings at both ends, just like the distal end cap 3, and is configured to be able to accommodate in its interior a pharmaceutical syringe 5 containing a pharmaceutical.

As shown in FIG. 1, a power button 6 is provided to the rear end side face of the main body case 1 of the pharmaceutical injection device, and the power to the pharmaceutical injection device can be switched on and off by pressing this button.

An inject button 7, a display component 10 disposed next to the inject button 7, an air expel button 8 disposed below the display component 10, and a complete button (confirm button) 9 disposed below the display component 10 are provided around the outside of the front face of the main body case 1.

The inject button 7 is used to start a pharmaceutical injection. The display component 10 displays the dose, messages, and so forth. The air expel button 8 is used to start expelling air. The complete button (confirm button) 9 is used to complete a set operation, confirm the end of processing, and so forth.

The air expel button 8 and the complete button 9 can also serve as a select button when looking at injection history, selecting setting data, and so forth.

In this Specification, the distal end face 3a side shall be the front side or distal end side of the pharmaceutical syringe unit 2 and the pharmaceutical injection device, and the opposite side (the power button 6 side, or the X direction side in FIG. 5) shall be the rear side.

2. Internal Configuration of Pharmaceutical Injection Device

The internal configuration and basic operation of the pharmaceutical injection device will now be described through reference to FIGS. 2 to 4.

Figure 2:
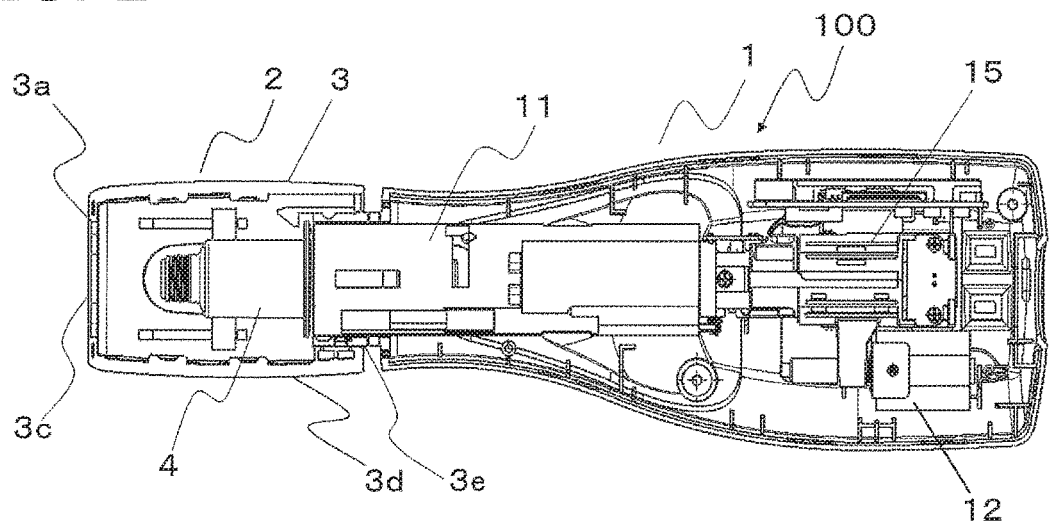
FIG. 2 is a cross section of the internal configuration of the pharmaceutical injection device in FIG. 1.
Figure 3:
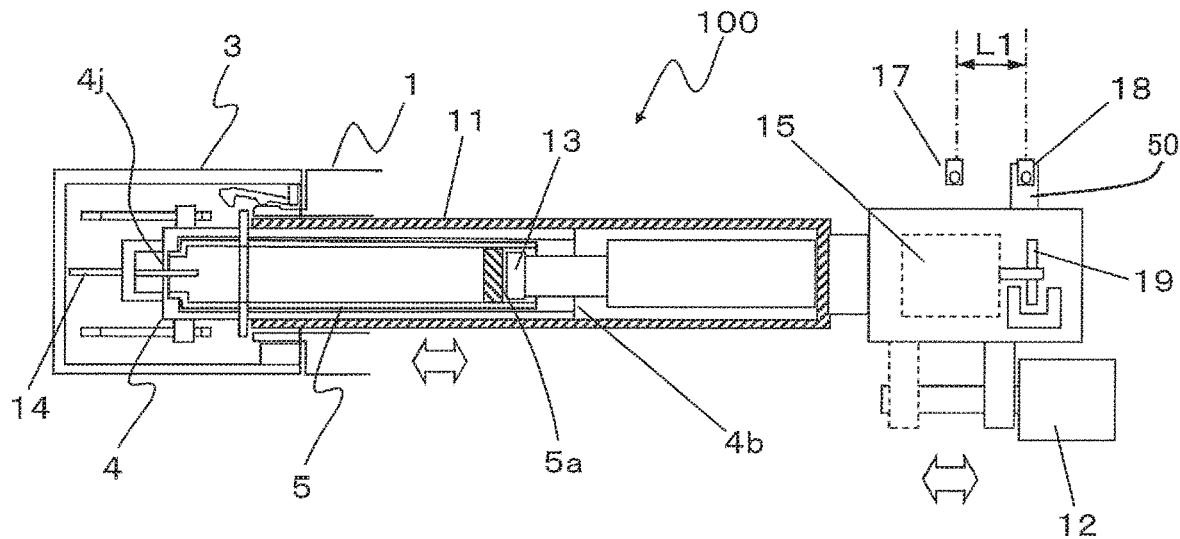
FIG. 3 is a simplified cross section of the pharmaceutical injection device in FIG. 1.

FIG. 2 is a cross section of the internal configuration of the pharmaceutical injection device in a state in which the pharmaceutical syringe unit 2 has been mounted, and FIG. 3 is a simplified cross section of the internal configuration.

An inner case 11 to which is mounted the syringe cover 4 in which the pharmaceutical syringe 5 is housed is provided on the distal end side (the left side in FIGS. 2 and 3) of the pharmaceutical injection device.

Figure 6:
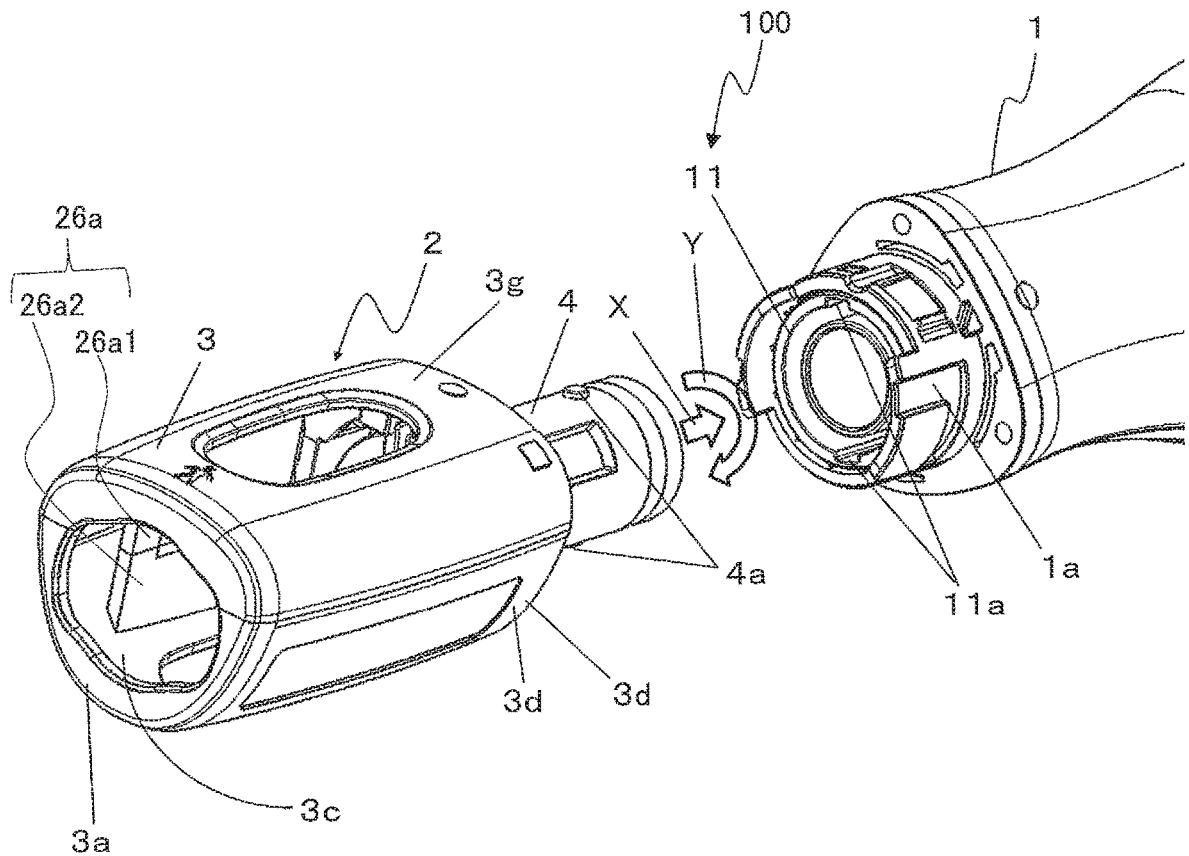
FIG. 6 is a main component oblique view of the state when a pharmaceutical syringe unit is mounted to the pharmaceutical injection device in FIG. 1.
Figure 10A:
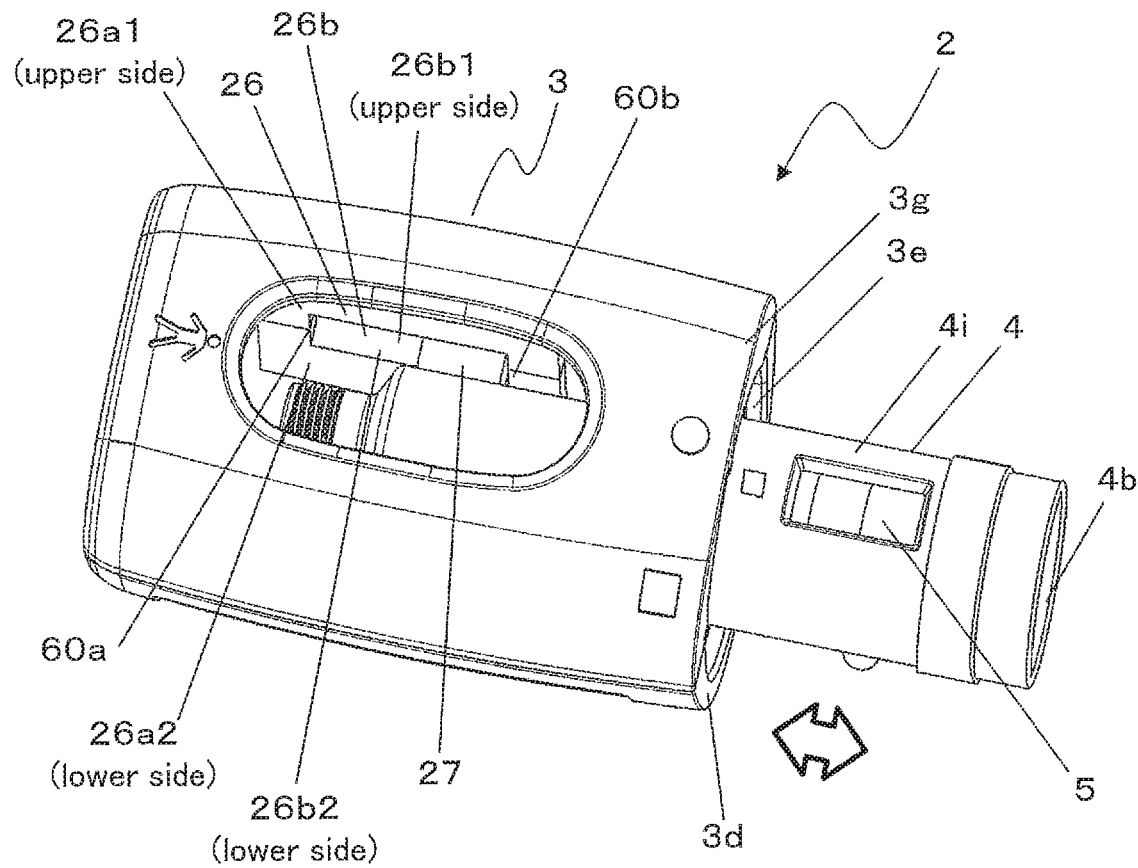
FIG. 10A is an oblique view of the pharmaceutical syringe unit in FIG. 5.
Figure 10B:
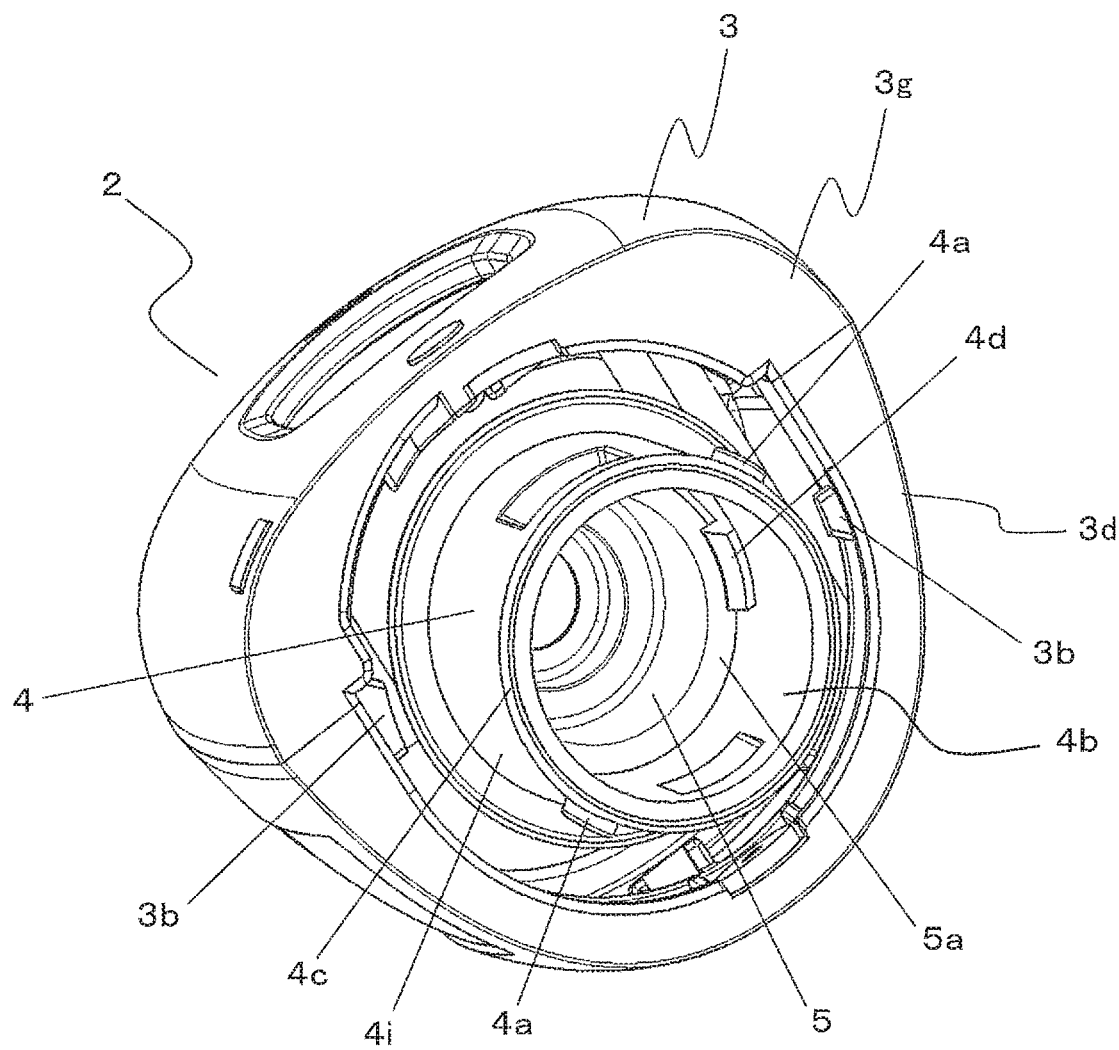
FIG. 10B is an oblique view of the pharmaceutical syringe unit in FIG. 5 (rear end side: opposite side from injection needle mounting side)
Figure 10C:
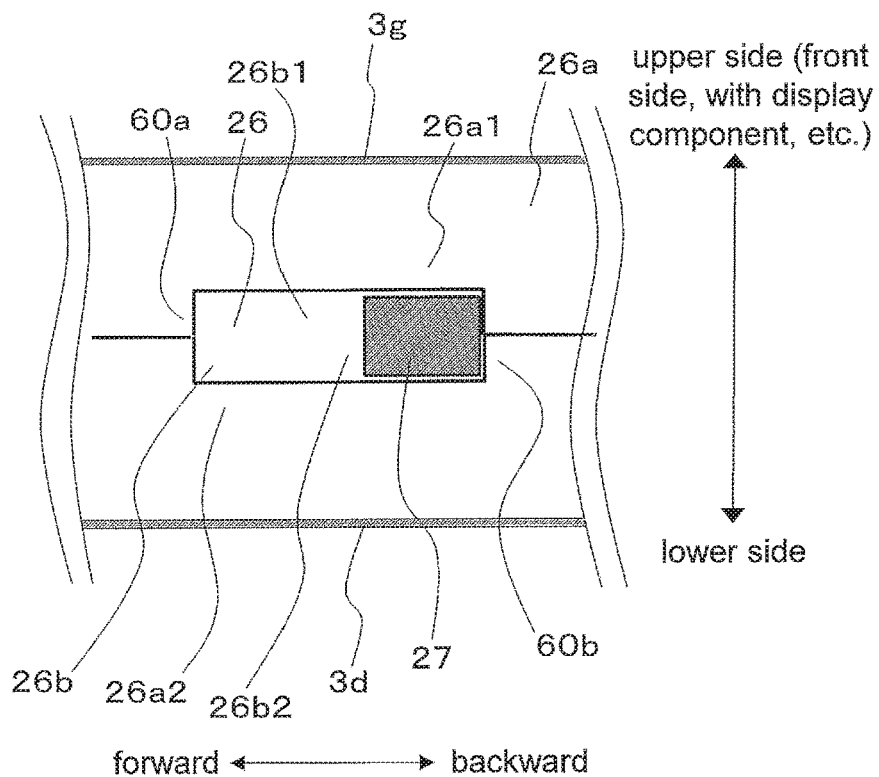
FIG. 10C illustrates the guide component of the pharmaceutical syringe unit in FIG. 10A.
Figure 10D:
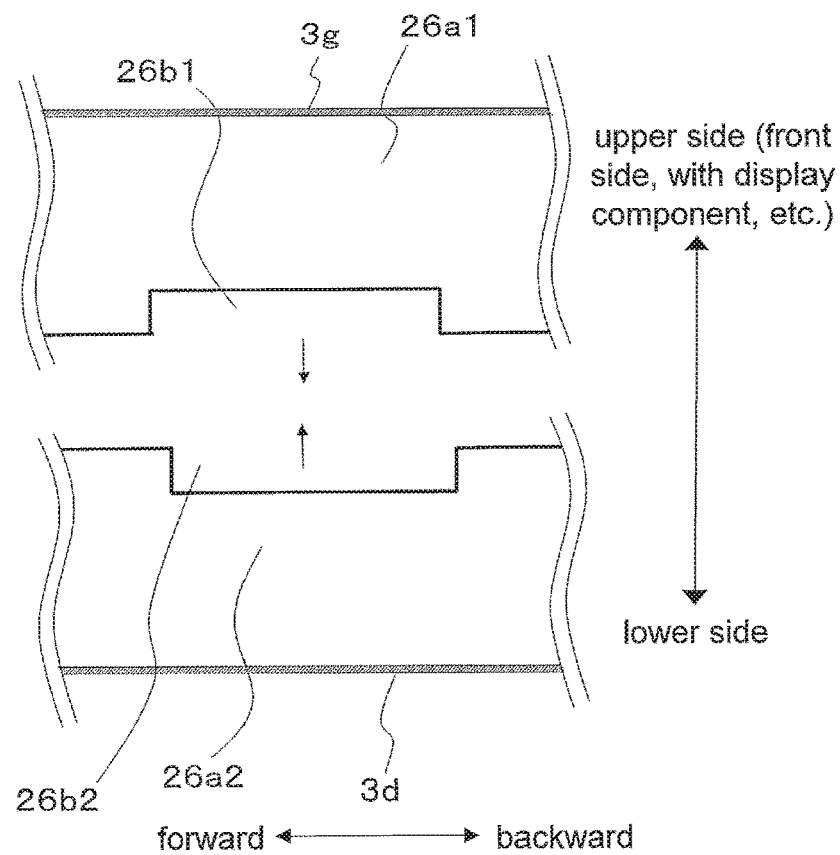
FIG. 10D illustrates the guide component of the pharmaceutical syringe unit in FIG. 10A.

In this case, the distal end cap 3 that encloses the syringe cover 4 is engaged on the distal end side of the main body case 1 (see FIGS. 6 and 10B).

Also, a slide motor 12 that performs the needle insertion and needle withdrawal operations and a piston drive motor 15 that drives a piston 13 are provided to the rear inside the main body case 1.

The piston drive motor 15 is disposed to the rear of the piston 13 and the piston drive motor 15 moves the piston 13 forward and backward. The piston drive motor 15 causes the piston 13 to be inserted from a rear opening (piston insertion opening) 4b in the syringe cover 4, and the rear end 5a of the pharmaceutical syringe 5 that is housed in the interior is pushed to the left in FIG. 2 by the piston 13, whereupon the pharmaceutical in the interior is injected in a specific amount from an injection needle 14 on the distal end side into the body.

Figure 4:
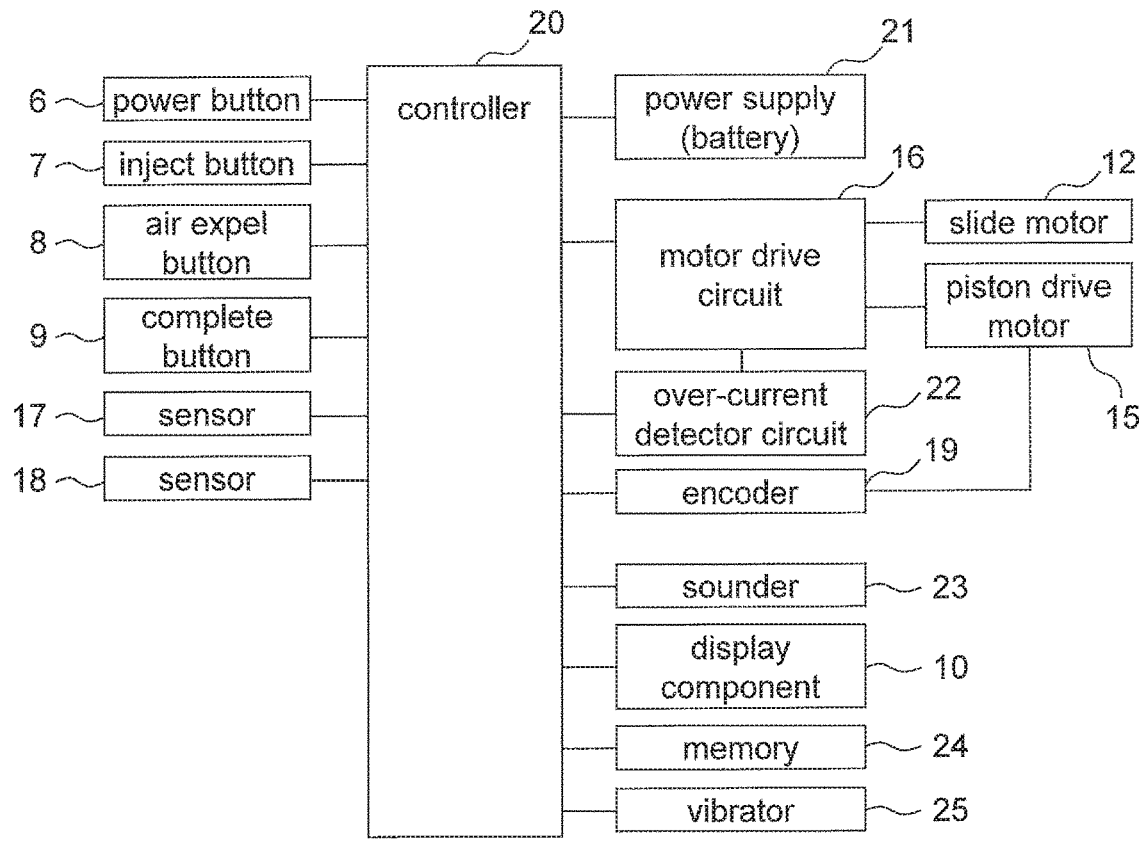
FIG. 4 is an electrical block diagram of the pharmaceutical injection device in FIG. 1.

The slide motor 12 and the piston drive motor 15 are connected to a motor drive circuit 16 that controls the drive of these motors (see FIG. 4).

A sensor 17 which confirms the position (needle insertion position) to which the inner case 11 has moved forward (the distal end side; to the left in FIGS. 2 and 3) when the inner case 11 is moved in the forward and backward direction by the slide motor 12, and a sensor 18 which confirms the position (needle withdrawal position) to which the inner case 11 has moved rearward (rear end side; to the right in FIGS. 2 and 3) are provided inside the main body case 1.

The sensor 17 and the sensor 18 are constituted by a reflecting or transmitting type of photosensor, etc., and perform position confirmation by using a blocking plate 50 that is connected to the inner case 11 and moves along with it. Specifically, the sensor 17 and the sensor 18 are each made up of a light emitting element and a light receiving element, and when the blocking plate 50 moves in between the light emitting element and the light receiving element and blocks the light from the light emitting element, the light emitting element detects this change, allowing the position to be confirmed.

This is how the slide motor 12 is driven and stopped.

The distance between the sensor 17 and the sensor 18 corresponds to the distance L1 between the needle insertion position and the needle withdrawal position. That is, the distance L1 is the slide stroke (movement distance) indicating the range over which the slide motor 12 can move the inner case 11 in the forward and backward direction (see FIG. 3).

An encoder 19 is provided near the piston drive motor 15 that drives the piston 13. The pharmaceutical dose is confirmed from how far the piston 13 moves, and the amount of movement of the piston 13 can be found by this encoder 19. Consequently, the injection operation is controlled while the proper dose is confirmed.

3. Control Blocks of Pharmaceutical Injection Device

The block configuration of the internal electrical control system will now be described through reference to the control block diagram in FIG. 4.

A controller 20 that performs main control over the pharmaceutical injection device is connected to the above-mentioned power button 6, inject button 7, air expel button 8, and complete button 9, and the input signals of these buttons all go into the controller 20.

The controller 20 is also connected to the sensor 17, the sensor 18, and the encoder 19. The signals from these are inputted to the controller 20, and the controller 20 obtains information about the positions of the various drive systems.

Furthermore, the controller 20 is connected to an over-current detector circuit 22 that detects abnormalities in the motor drive circuit 16 and the motor drive system, and the controller 20 outputs control instructions to the motor drive system, and inputs motor drive system abnormalities to control the operations for handling them.

With the pharmaceutical injection device, the controller 20 is also connected to the display component 10, a sounder 23 that emits audible output such as sound, a vibrator 25 that gives vibration output, a power supply (battery) 21 (the power supply for the pharmaceutical injection device), and a memory 24 that holds setting data and injection history information.

4. Mounting Between Pharmaceutical Syringe Unit and Main Body Case

The portion where the pharmaceutical syringe unit 2 is mounted to the main body case 1 will now be described through reference to FIGS. 5 and 6.

Figure 5:
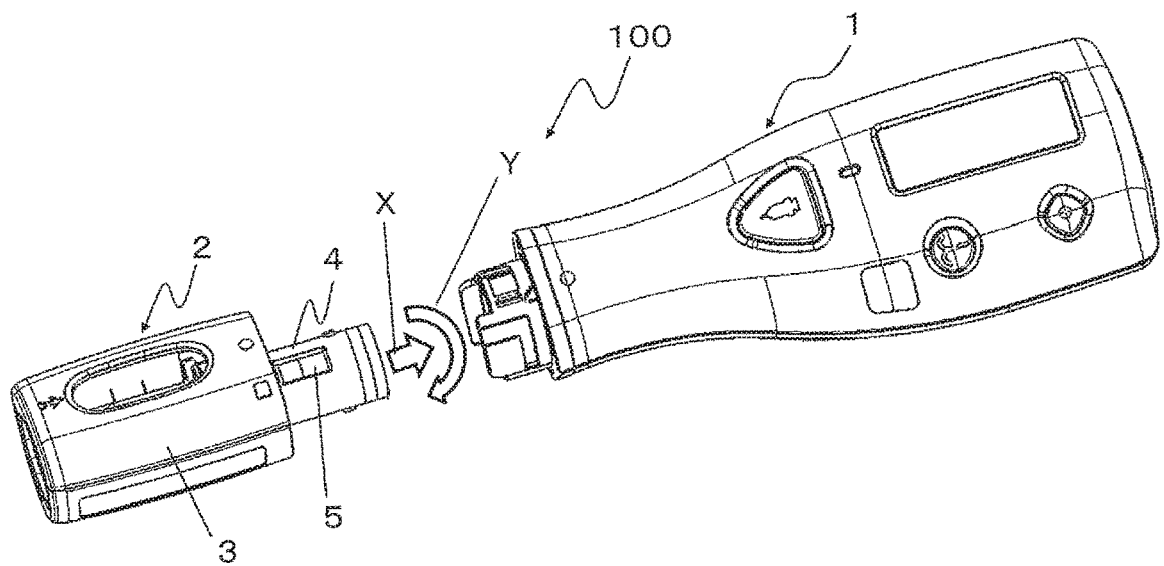
FIG. 5 is an oblique view of the state when a pharmaceutical syringe unit is mounted to the pharmaceutical injection device in FIG. 1.

As shown in FIGS. 5 and 6, protrusions 4a that engage with grooves 11a in the inner case 11 disposed in the interior of the main body case 1 are provided to the syringe cover 4 constituting part of the pharmaceutical syringe unit 2. In FIG. 6, two each of the protrusions 4a and the grooves 11a are provided, and in this example they are disposed at positions offset by 180 degrees, but this is not the only option, and just one of each may be provided, or three or more.

Consequently, when the pharmaceutical syringe unit 2 is mounted to the main body case 1, the protrusions 4a on the syringe cover 4 are guided by the grooves 11a in the inner case 11 as they move inward in the direction indicated by the arrow X (a direction parallel to the axis of the cylindrical syringe cover 4; toward the main body case 1). After this, when the pharmaceutical syringe unit 2 is rotated in the direction indicated by the arrow Y (rotated to the right (clockwise) around the axis of the above-mentioned arrow X), the protrusions 4a move in along the grooves 11a, all the way to the back. This results in the syringe cover 4 being mounted to the inner case 11.

The protrusions 4a on the syringe cover 4 here correspond to an example of a second engagement component, and the grooves 11a in the inner case 11 correspond to an example of a second engaged part.

At the same time as this, the distal end cap 3 is mounted to the main body case 1. Specifically, just as with the protrusions 4a, protrusions 3b (an example of a first engagement component; see FIG. 10B) are provided on the inner peripheral side of the distal end cap 3 provided to the pharmaceutical syringe unit 2, and main body grooves 1a (see FIG. 6) are provided to the main body case 1 so as to engage with the protrusions 3b of the distal end cap 3.

The grooves 11a here are formed in an L shape so as to guide the protrusions 4a in the axial direction and the rotation direction. The main body grooves 1a are formed in an L shape so as to guide the protrusions 3b (see FIG. 10B) provided on the inner peripheral side of the distal end cap 3 in the axial direction and the rotation direction. The phases of the protrusions 4a and the grooves 11a, and of the protrusions 3b and the main body grooves 1a are matched up (in other words, the positional relations are matched up) so that the main body grooves 1a will coincide with the protrusions 3b (see FIG. 10B) formed on the outer peripheral side of the distal end cap 3 when the protrusions 4a are inserted into the grooves 11a, so the distal end cap 3 is mounted to the main body case 1, and the syringe cover 4 to the inner case 11, by operation in the X and Y directions as discussed above. The above-mentioned inner case 11 is disposed in the interior of the main body case 1, and is able to slide with respect to the main body case 1, so when the pharmaceutical syringe unit 2 is mounted to the main body case 1, the syringe cover 4 is able to slide along with the inner case 11.

5. Needle Insertion Position and Needle Withdrawal Position

Figure 7:
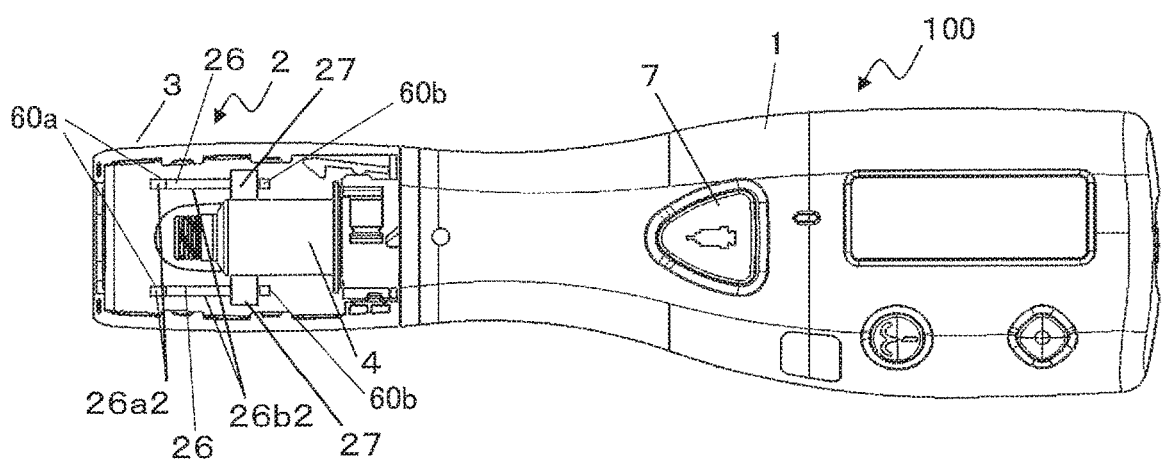
FIG. 7 is a plan view of the pharmaceutical injection device in FIG. 1, showing a cross section of part of the pharmaceutical syringe unit.
Figure 8:
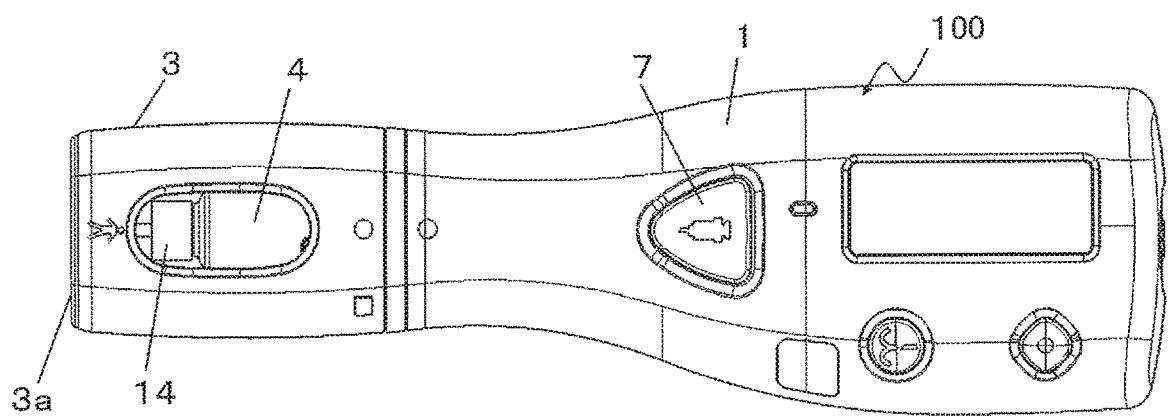
FIG. 8 is a plan view of the pharmaceutical injection device in FIG. 1 (when the injection needle is withdrawn)
Figure 9:
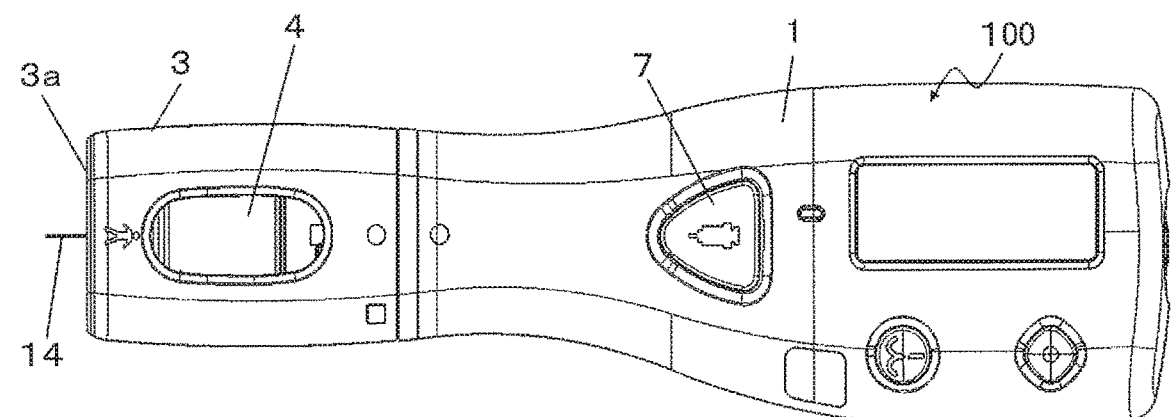
FIG. 9 is a plan view of the pharmaceutical injection device in FIG. 1 (when the injection needle is inserted)

FIGS. 1 and 7 show the state when the pharmaceutical syringe unit 2 has been mounted to the distal end side of the main body case 1, as discussed above. FIGS. 8 and 9 show the state when the injection needle 14 has been mounted to a needle mounting component 28 (see FIGS. 11 to 13, etc.) on the distal end side of the syringe cover 4.

The mounting of the injection needle 14 to the syringe cover 4 will be described in detail below through reference to FIGS. 16 to 22, but in the state when the injection needle 14 has been mounted to the syringe cover 4, as shown in FIG. 8, the distal end of the injection needle 14 is not exposed from the distal end face 3a of the distal end cap 3. Consequently, the injection needle 14 is prevented from accidentally puncturing the skin, except during the injection operation.

In the state in FIG. 8, when the distal end face 3a of the distal end cap 3 is placed against the skin and the inject button 7 is pressed in this state, the inner case 11 is moved to the distal end side by the above-mentioned slide motor 12 (also called a needle insertion and withdrawal driver), and along with this the syringe cover 4 that is mounted to the inner case 11 and the injection needle 14 that is mounted to the needle mounting component 28 of the syringe cover 4 also move to the distal end side. As a result, as shown in FIG. 9, the injection needle 14 sticks out from the distal end face 3a of the distal end cap 3 and punctures the skin.

This is the needle insertion operation. When this operation is complete, that is, when the blocking plate 50 has been detected by the sensor 17, the positions of the inner case 11 and the syringe cover 4 are the needle insertion position.

In this needle insertion state, the piston 13 is then moved to the distal end side by drive of the piston drive motor 15 (also called an injection driver), and the rear end 5a of the pharmaceutical syringe 5 is pushed to the distal end side. Consequently, the pharmaceutical inside the pharmaceutical syringe 5 is injected through the injection needle 14 and into the body (see FIG. 3).

After this, when the specified amount of pharmaceutical has been injected (the injected amount is monitored by the encoder 19, etc.), the controller 20 stops the piston drive motor 15, and the piston 13 comes to a stop. This operation is the injection operation.

Once the piston 13 has come to a stop, the inner case 11 is then moved to the rear end side by the inner case 11, and consequently, the syringe cover 4 also moves to the rear end side, and the injection needle 14 attached to the needle mounting component 28 at the distal end of the syringe cover 4 also moves into the interior from the distal end face 3a of the distal end cap 3.

That is, the needle is withdrawn from the skin (the injection needle 14 is pulled out), and this is the needle withdrawal operation. Once the needle withdrawal operation is complete, that is, once the blocking plate 50 has been detected by the sensor 18, the positions of the inner case 11 and the syringe cover 4 are the needle withdrawal position.

If the pharmaceutical in the pharmaceutical syringe 5 runs out, the piston drive motor 15 will pull the piston 13 back to the rear end side, and the piston 13 will be retracted to its home position (its initial position).

After this pharmaceutical injection, in this embodiment the pharmaceutical syringe unit 2 is removed from the main body case 1, and then the injection needle 14 is removed from the syringe cover 4, resulting in the state in FIGS. 10A and 10B, and in this state the unit is put into the storage case and stored in a refrigerator or other cool place.

That is, a unit is created (the pharmaceutical syringe unit 2) in a state in which the pharmaceutical syringe 5 is held in the syringe cover 4 and the syringe cover 4 is held in the distal end cap 3, and the unit is stored in this state. The configuration is such that at this time the syringe cover 4 does not come loose from the distal end cap 3, and the pharmaceutical syringe 5 does not come loose from the syringe cover 4.

6. Pharmaceutical Syringe Unit

The configuration of the pharmaceutical syringe unit will now be described.

As shown in FIGS. 10A and 10B, the pharmaceutical syringe unit 2 in this embodiment comprises the distal end cap 3 and the syringe cover 4 that is disposed inside the distal end cap 3 so as to be capable of moving in the forward and backward direction with respect to the distal end cap 3.

7. Distal End Cap

As discussed above, the distal end cap 3 is substantially cylindrical, has the distal end opening 3c on the front end side (see FIG. 2), and has the rear end opening 3e on the rear end side. The distal end face 3a comes into contact with the body during needle insertion.

As will be discussed in detail below, a mechanism for releasing a restrictor 29 that restricts the movement of the syringe cover 4 when the pharmaceutical syringe unit 2 has been mounted to the main body case 1 is provided on the outer peripheral side of the rear end opening 3e and inside the distal end cap 3 (see FIG. 13).

8. Syringe Cover

Figure 11:
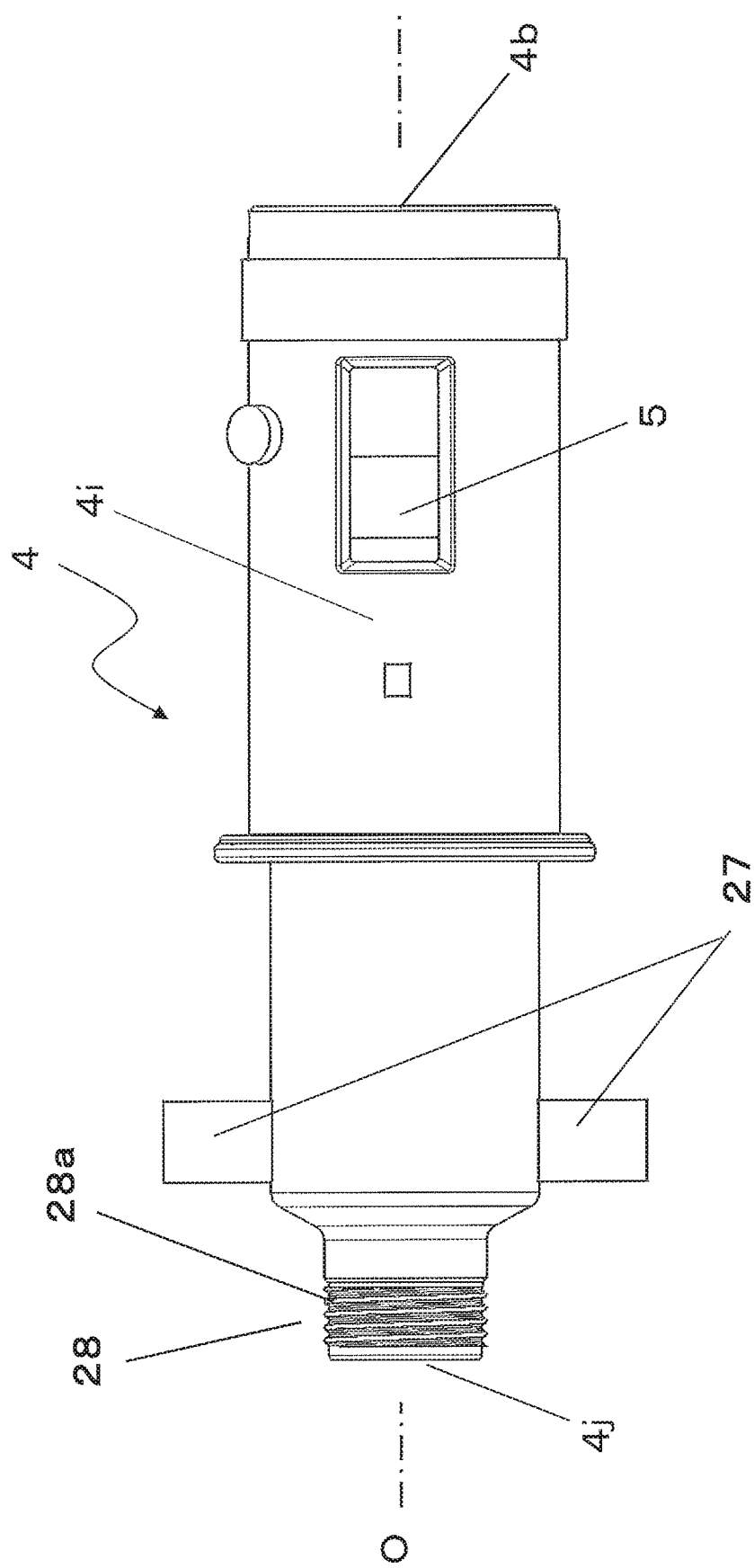
FIG. 11 is a plan view of the syringe cover of the pharmaceutical syringe unit in FIG. 10A.

The configuration of the syringe cover 4 will now be described. FIG. 11 is a plan view of the syringe cover 4. The syringe cover 4 has a cover main body 4i that is substantially cylindrical. A front opening 4j (see FIG. 3) is formed on the front end side of the syringe cover main body 4i, and the rear opening 4b is formed on the rear end side.

The injection needle 14 is mounted to the front opening 4j, and the piston 13 is inserted into the rear opening 4b. As shown in FIG. 11, the syringe cover main body 4i has flat flanges 27 formed sticking out from the side faces. The flanges 27 are disposed so that their plane follows the center axis O of the syringe cover main body 4i. Also, two of the flanges 27 are provided, and these flanges 27 are disposed symmetrically to the center axis O of the syringe cover main body 4i. As will be discussed in further detail below, the flanges 27 mate with guide components 26.

As shown in FIG. 10B, the syringe cover 4 has a turning ring 4c. The turning ring 4c is attached to the peripheral edge of the rear opening 4b, on the outside of the syringe cover main body 4i. This turning ring 4c is able to rotate around the center axis of the syringe cover 4, and has protrusions (not shown) facing the inner periphery.

The syringe cover 4 further has support tabs 4d that are attached on the inside of the syringe cover main body 4i and are configured such that they widen to conform to the inner peripheral face side of the cover main body 4i in a state of not supporting the pharmaceutical syringe 5, and do not catch on the rear end 5a of the pharmaceutical syringe 5.

When it is time to replace the pharmaceutical syringe 5, the turning ring 4c is turned counter-clockwise to move the protrusions of the turning ring 4c to a position where they do not push the support tabs 4d inward, creating a state in which the support tabs 4d do not catch on the rear end 5a of the pharmaceutical syringe 5.

On the other hand, when the pharmaceutical syringe 5 is inserted into and held in the syringe cover 4, the turning ring 4c is turned clockwise to move the protrusions of the turning ring 4c to a position where they do push the support tabs 4d inward, creating a state in which the support tabs 4d do catch on the rear end 5a of the pharmaceutical syringe 5.

The turning ring 4c may also be given the same function in the reverse rotation direction from that discussed above.

Also, the turning ring 4c and the support tabs 4d correspond to an example of a support component that supports the pharmaceutical syringe.

9. Syringe Cover Support Configuration of Distal End Cap

As discussed above, the flanges 27 (correspond to a guided part), which are guided in the forward and backward direction by the groove-like guide components 26 provided to the distal end cap 3, are provided on the left and right around the outside of the syringe cover 4 as shown in FIG. 11. In FIG. 11 there are two flanges 27, one above and one below, but this is not the only option.

The guide components 26 have guide grooves 26b into which the flanges 27 fit, and stoppers 60a and 60b that prevent the flanges 27 from coming out of the guide grooves 26b.

As shown in FIGS. 6, 7, and 10A to 10D, the guide components 26 are formed by plate-like risers 26a disposed on the inside of the distal end cap 3. The groove-like guide grooves 26b are formed in the approximate center in the up and down direction of the risers 26a, passing through the risers 26a in the forward and backward direction, with the portion of the risers 26a on the front side of the guide grooves 26b forming the stopper 60a, and the portion of the risers 26a on the rear side of the guide grooves 26b forming the stopper 60b.

This will now be described in further detail. As can be seen from FIGS. 7 and 10A to 10D, risers 26a1 and 26a2 for forming the guide components 26 are provided in the interiors of an upper member 3g and a lower member 3d obtained by dividing the distal end cap 3 into upper and lower parts. The riser 26a1 is formed facing down from the inside of the upper member 3g, and a recess 26b1 is formed along the forward and backward direction at the lower end thereof. The riser 26a2 is formed facing up from the inner periphery of the lower member 3d of the distal end cap 3, and a recess 26b2 is formed along the forward and backward direction at the upper end thereof.

The groove-like guide grooves 26b are formed by the recesses 26b1 and 26b2 formed at the contact parts of the risers 26a1 and 26a2 by bringing these risers 26a1 and 26a2 into contact in the up and down direction. Inside these guide components 26, the flanges 27 of the syringe cover 4 are guided slidably in the forward and backward direction.

Also, because the flanges 27 are in the guide components 26, the syringe cover 4 is prevented from coming loose from the distal end cap 3.

That is, since contact between the risers 26a1 and 26a2 forms the stoppers 60a and 60b ahead of and behind the guide grooves 26b, the flanges 27 do not slide forward and backward past the risers 26a1 and 26a2, and this prevents the syringe cover 4 from coming loose from the distal end cap 3.

The guide components 26 are provided on the left and right so as to correspond to the two flanges 27.

Figure 12:
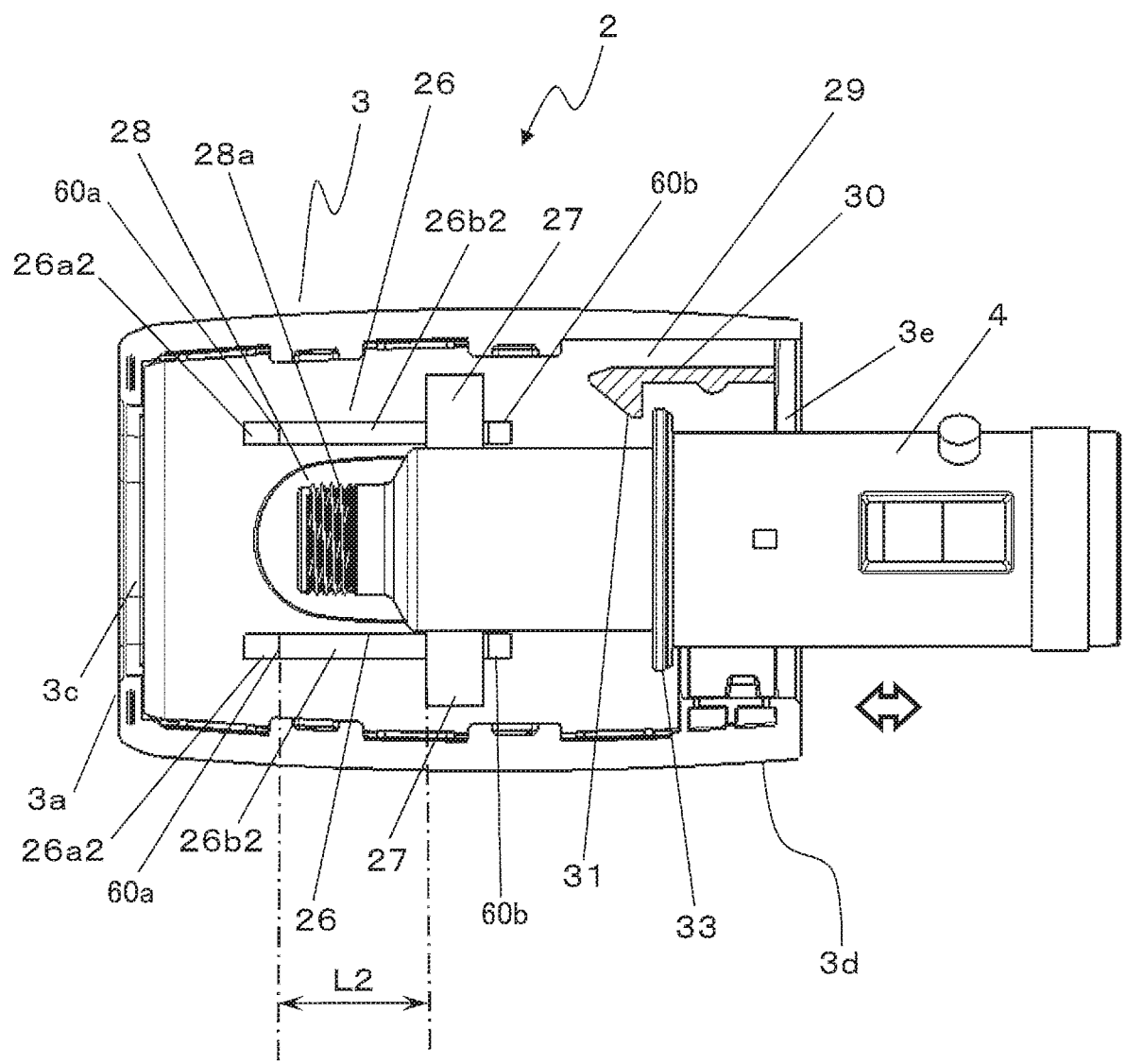
FIG. 12 is a cross section of the pharmaceutical syringe unit in FIG. 10A.
Figure 13:
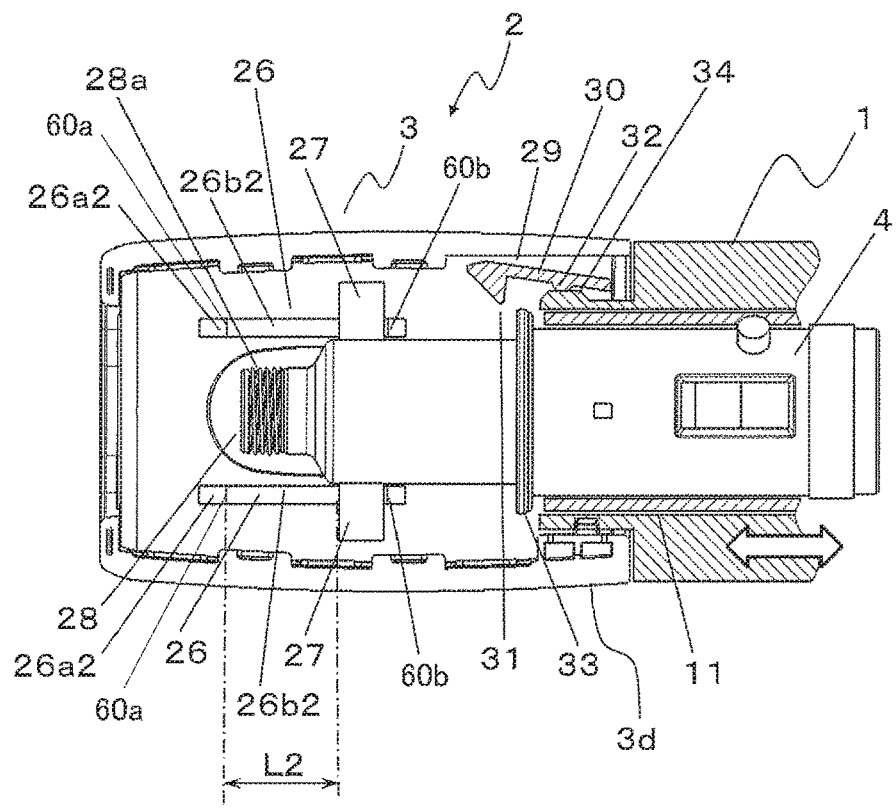
FIG. 13 is a cross section of part of the main body case and the pharmaceutical syringe unit in FIG. 10A.

Also, in this embodiment, as shown in FIG. 13, in a state in which the distal end cap 3 of the pharmaceutical syringe unit 2 has been mounted to (engaged with) the main body case 1 of the pharmaceutical injection device, sliding of the syringe cover 4 to the distal end side of the distal end cap 3 is permitted. As shown in FIG. 12, in a state in which the distal end cap 3 has been removed (disengaged) from the main body case 1 of the pharmaceutical injection device, sliding of the syringe cover 4 to the distal end side of the distal end cap 3 is restricted by the above-mentioned restrictor 29. This restrictor 29 is provided to the inside of the rear part of the distal end cap 3. In FIG. 12, the upper member 3g of the distal end cap 3 has been removed for the sake of illustration.

The restrictor 29 will now be described in further detail. This restrictor 29 has a catch 30 formed facing forward from the outer edge of the rear end opening 3e of the distal end cap 3. The catch 30 is biased to the outer peripheral part side of the syringe cover 4 from the distal end cap 3.

This catch 30 has a first protrusion 31 formed at the distal end and facing inward, and a second protrusion 32 formed in the approximate center in the forward and backward direction and facing inward.

As shown in FIG. 12, in a state in which the distal end cap 3 is not mounted to (is disengaged from) the main body case 1 of the pharmaceutical injection device, the first protrusion 31 restricts the sliding of the syringe cover 4 to the distal end side of the distal end cap 3. As shown in FIG. 13, in a state in which the distal end cap 3 has been mounted to (engaged with) the main body case 1 of the pharmaceutical injection device, the second protrusion 32 moves the catch 30 in the outer peripheral direction of the syringe cover 4, so the restriction on the sliding of the syringe cover 4 to the distal end side of the distal end cap 3 is released.

More precisely, a flange 33 that engages with the first protrusion 31 of the catch 30 is provided to the outer peripheral part of the syringe cover 4. Also, in a state in which the distal end cap 3 constituting the pharmaceutical syringe unit 2 has been rotated in the Y direction in FIG. 5, that is, in a state in which the pharmaceutical syringe unit 2 has been mounted to the main body case 1, a protrusion 34 formed on the main body case 1 pushes the second protrusion 32 outward, as shown in FIG. 13.

That is, in the state in FIG. 13, the distal end cap 3 of the pharmaceutical syringe unit 2 is mounted to the main body case 1, so at this point, as shown in FIGS. 8 and 9, the injection needle 14 needs to be moved along with the syringe cover 4 to the distal end side. Accordingly, the first protrusion 31 of the restrictor 29 is moved to the outer peripheral side, and the first protrusion 31 does not engage with the flange 33 provided around the outside of the syringe cover 4.

In contrast, FIG. 12 shows a state in which the pharmaceutical syringe unit 2 has been removed from the main body case 1, so at this point the first protrusion 31 of the restrictor 29 moves to the inner peripheral side as shown in FIG. 12 (moves closer to the center of the axis of the syringe cover 4), and the first protrusion 31 engages with the flange 33 provided around the outside of the syringe cover 4. The term "engage" here encompasses a state in which the first protrusion 31 is located near the front side of the flange 33 as shown in FIG. 12, and the first protrusion 31 will be engaged by a small forward movement of the syringe cover 4.

This prevents the syringe cover 4 from moving to the distal end side.

Thus, in this embodiment, after the injection of the pharmaceutical, the pharmaceutical syringe unit 2 is removed from the main body case 1, and the injection needle 14 is removed from the syringe cover 4 to create the state in FIG. 12, 10A, or 10B, and in this state (in which the pharmaceutical syringe 5 is housed in the pharmaceutical syringe unit 2), the unit is put in its storage case and stored in a refrigerator or other cool place.

That is, a unit is created (corresponds to the pharmaceutical syringe unit 2) in a state in which the pharmaceutical syringe 5 is held in the syringe cover 4 and the syringe cover 4 is held in the distal end cap 3, and the unit is put into its storage case in this state and stored in a refrigerator. The pharmaceutical syringe unit 2 is configured such that at this time the syringe cover 4 does not come loose from the distal end cap 3, and the pharmaceutical syringe 5 does not come loose from the syringe cover 4.

10. Injection Needle 14 and Needle Unit 35 Including Same

Next, the injection needle 14 used for injecting the pharmaceutical contained in the pharmaceutical syringe 5 into a body, and the needle unit 35 that includes this injection needle 14, with the pharmaceutical injection device will now be described through reference to FIGS. 14 and 15.

Figure 14:
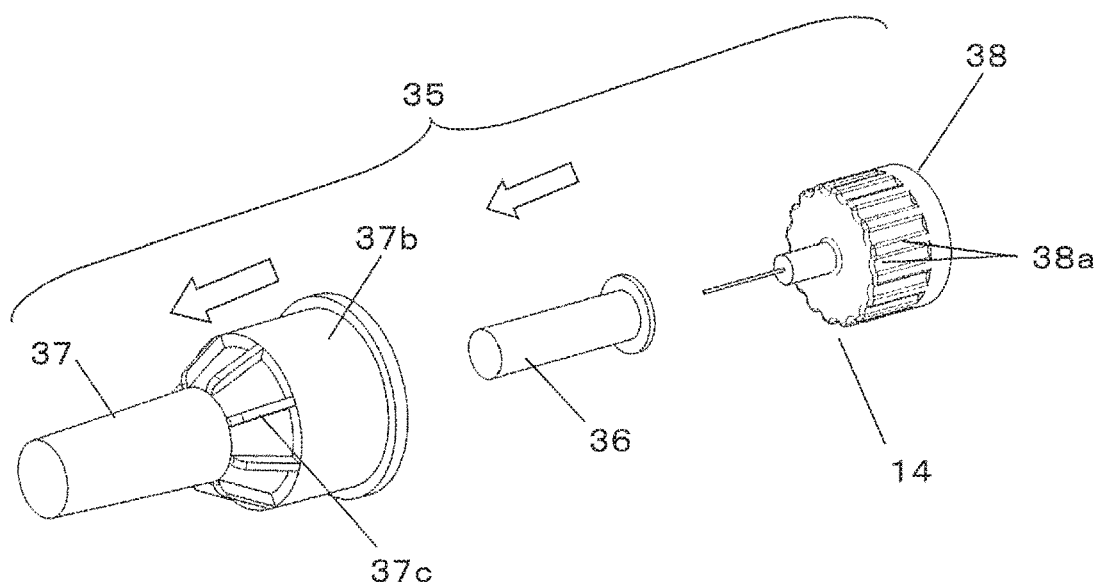
FIG. 14 is an exploded oblique view of a needle unit that is mounted to the pharmaceutical syringe unit in FIG. 10A.
Figure 15:
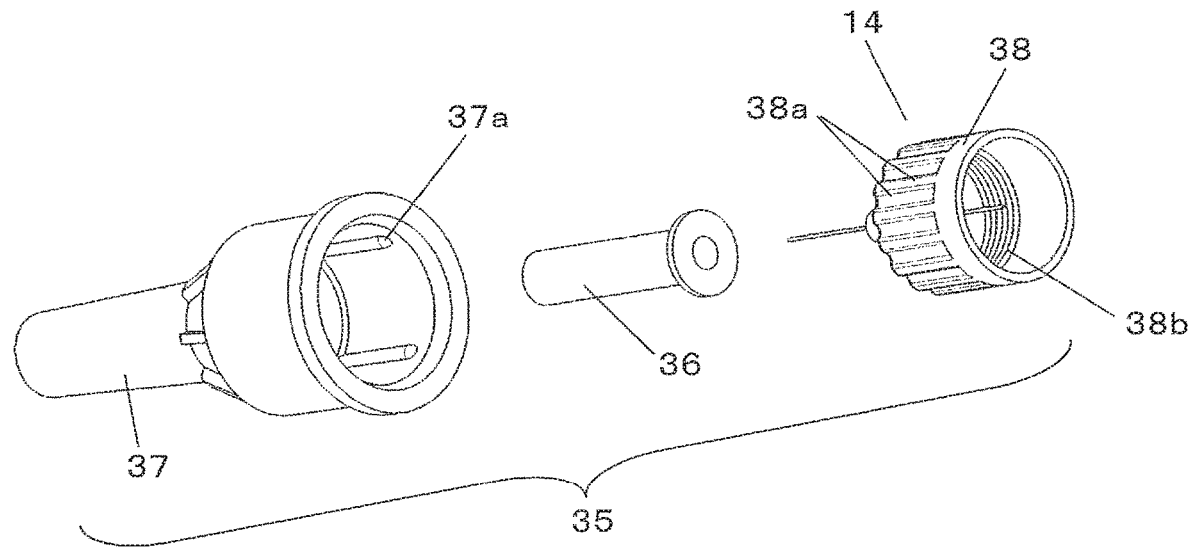
FIG. 15 is an exploded oblique view of the needle unit in FIG. 14.

FIGS. 14 and 15 are exploded oblique views of the needle unit 35. As shown in FIGS. 14 and 15, the needle unit 35 is made up of the injection needle 14, a needle cap 36 that covers the needle tip portion, and a needle case 37 that covers the injection needle 14 and the needle cap 36.

A needle base 38, which is the main portion of the injection needle 14, is cylindrical in shape, and has a textured part 38a consisting of bumps and recesses formed on its outer peripheral face. These engage with protrusions 37a provided to the inner peripheral part of the needle case 37.

These protrusions 37a are provided to allow operation even when the injection needle 14 is covered by the needle case 37 during attachment and removal of the injection needle 14, and allow the user to safely operate the unit without having to grip the injection needle 14 directly with his fingers.

The needle case 37 has on one side a large-diameter part 37b, and a knurled part 37c is provided to the portion to which this large-diameter part 37b is linked.

Consequently, when the user operates the needle case 37 with his fingers, the large-diameter part 37b is a size that is easy to grip, and the knurled part 37c allows the needle case 37 and the injection needle 14 to be operated together, affording to good grip to the fingers and making operation easier.

Female threads 38b (see FIG. 15) are provided on the inner peripheral side of the needle base 38 of the injection needle 14. These threads 38b mesh with male threads 28a on the needle mounting component 28 provided to the distal end part of the syringe cover main body 4i, which attaches the injection needle 14 to the needle mounting component 28 (see FIGS. 1 to 13 and FIGS. 20 and 21).

After the injection of the pharmaceutical, if the injection needle 14 is removed and discarded, the needle cap 36 is not used, and the injection needle 14 is covered directly by the needle case 37.

11. Pharmaceutical Injection Method

The method for mounting the pharmaceutical syringe unit 2 to the main body case 1 of the pharmaceutical injection device and actually injecting the pharmaceutical will now be described through reference to FIGS. 16 and 17.

First, the pharmaceutical syringe unit 2 in the state prior to being mounted to the main body case 1 will be described. As shown in FIGS. 10A, 10B, 12, 18, and 19, the pharmaceutical syringe 5 is put into the syringe cover 4, and in this state the pharmaceutical syringe 5 is held in the interior of the syringe cover 4.

The syringe cover 4 that holds the pharmaceutical syringe 5 is mounted in the interior of the distal end cap 3, thereby constituting the pharmaceutical syringe unit 2.

As shown in FIGS. 12 and 13, at this point the flanges 27 provided around the outside of the syringe cover 4 are engaged with the groove-like guide components 26 of the distal end cap 3, so that movement of the syringe cover 4 in the opposite direction from the needle mounting component 28 is restricted by the stopper 60b. Consequently, the syringe cover 4 is prevented from coming loose from the distal end cap 3 constituting the pharmaceutical syringe unit 2.

Therefore, because the pharmaceutical syringe 5 is held in the syringe cover 4, and the syringe cover 4 is restricted by the distal end cap 3, the pharmaceutical syringe 5 is prevented from coming loose from or falling out of the pharmaceutical syringe unit 2.

Thus, the pharmaceutical syringe unit 2 can be put in a dedicated storage case and stored in a refrigerator or the like, or taken out of its storage case and the refrigerator and mounted to the main body case 1 of the pharmaceutical injection device, in a state in which the pharmaceutical syringe 5 is held, which makes the unit extremely convenient to use.

Next, the pharmaceutical syringe unit 2 with the mounted pharmaceutical syringe 5 is mounted to the main body case 1 as shown in FIGS. 5 and 6.

At this point, the syringe cover 4 engages with the inner case 11 of the main body case 1. Also, the piston 13 that moves through the inner case 11 is disposed through the rear opening 4b of the pharmaceutical syringe unit 2 at a position that is opposite the rear end of the pharmaceutical syringe 5 housed in the interior of the syringe cover 4 (see FIGS. 3 and 4).

That is, the piston 13 of the pharmaceutical injection device is disposed at a position that is opposite the rear end 5a of the pharmaceutical syringe 5 containing the pharmaceutical and housed in the interior of the syringe cover 4, through the rear opening 4b, which is the piston insertion opening of the syringe cover 4.

Therefore, when the piston drive motor 15 is driven and this piston 13 is moved, the rear end 5a is pushed to the distal end side, and as a result the pharmaceutical in the pharmaceutical syringe 5 can be injected into the body.

Thus, pharmaceutical injection preparation merely entails mounting the pharmaceutical syringe 5 to the main body case 1 of the pharmaceutical injection device in a state in which the pharmaceutical syringe 5 has already been mounted to the pharmaceutical syringe unit 2, and after the injection, the pharmaceutical syringe unit 2, with the pharmaceutical syringe 5 still mounted, can be put in its storage case and stored in a refrigerator, etc., which makes the unit very reliable and easy to use.

12. Pharmaceutical Syringe Unit in Injection Needle Mounted State

The features of the pharmaceutical syringe unit 2 when the injection needle 14 and the needle unit 35 that includes this injection needle 14 have been mounted, will now be described through reference to FIGS. 16 to 22.

Certain implementations of present invention are developed for use in a pharmaceutical injection device, so naturally, when it is time for pharmaceutical injection, the injection needle 14 is used to inject the pharmaceutical into the body.

Figure 16:
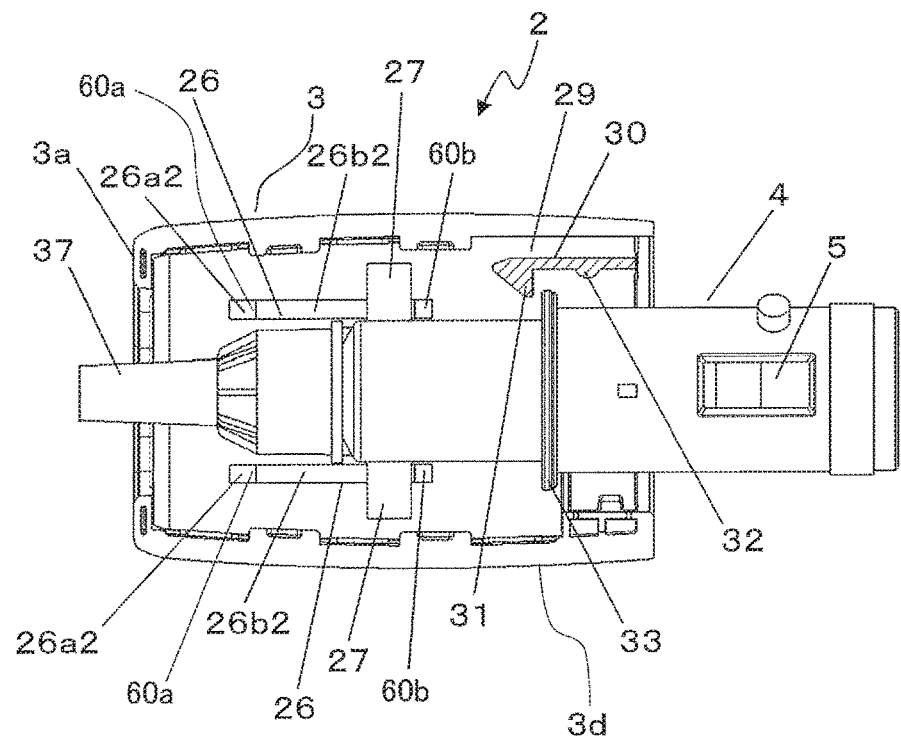
FIG. 16 is a cross section of the mounted state of the needle unit in FIG. 14.
Figure 17:
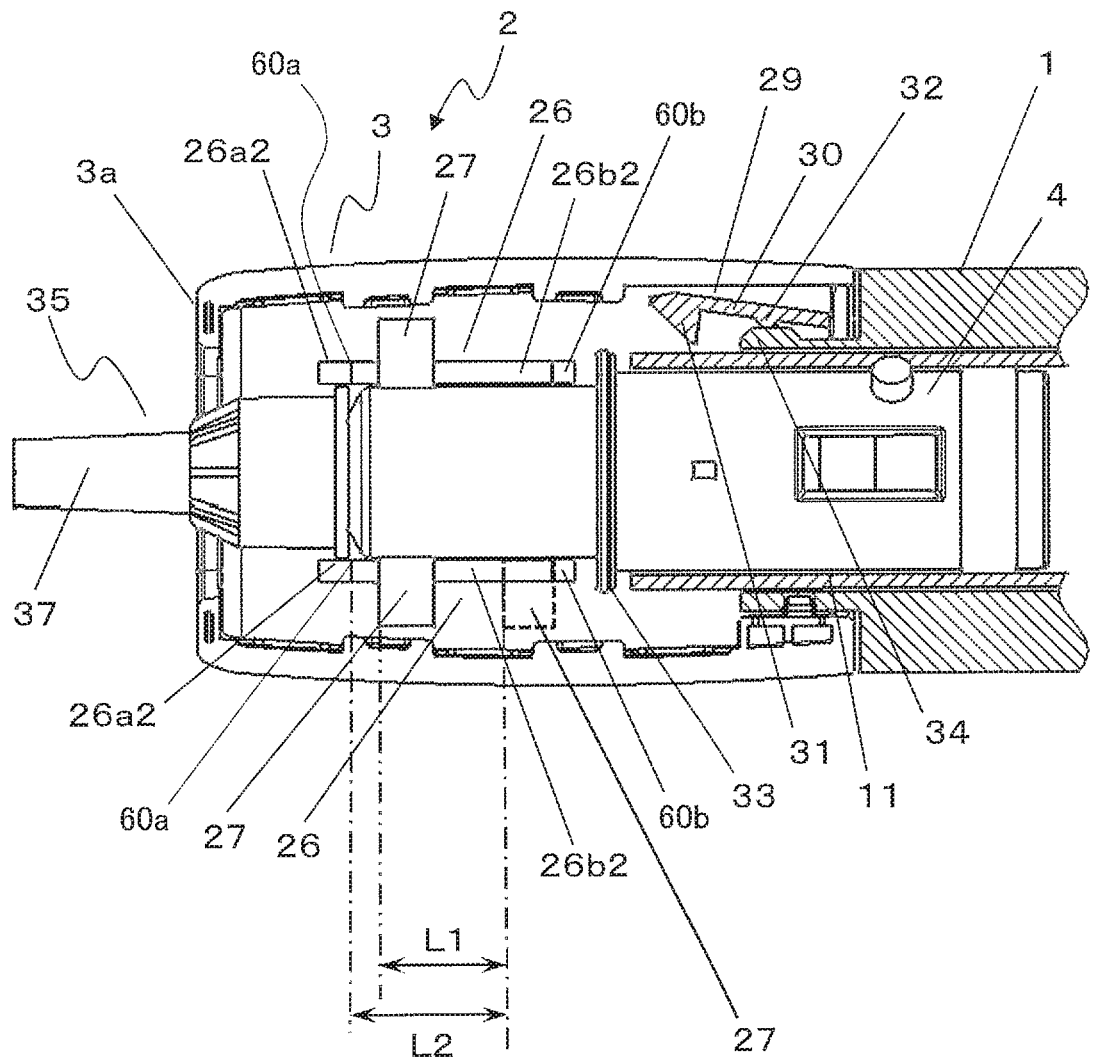
FIG. 17 is a cross section of the mounted state of the needle unit in FIG. 14.

FIGS. 16 and 17 show the pharmaceutical syringe unit 2 in a state in which an unused needle unit 35 (made up of the injection needle 14, the needle cap 36, and the needle case 37), or a needle case 37 containing a used injection needle 14, has been mounted to the needle mounting component 28 provided to the distal end part of the syringe cover 4. The needle case 37 is shown in FIGS. 16 and 17, but the needle unit 35 may be mounted instead of the needle case 37. FIG. 16 shows the state when the pharmaceutical syringe unit 2 has been removed from the main body case 1 of the pharmaceutical injection device, and FIG. 17 shows the state when the pharmaceutical syringe unit 2 has been mounted to the main body case 1.

Figure 18:
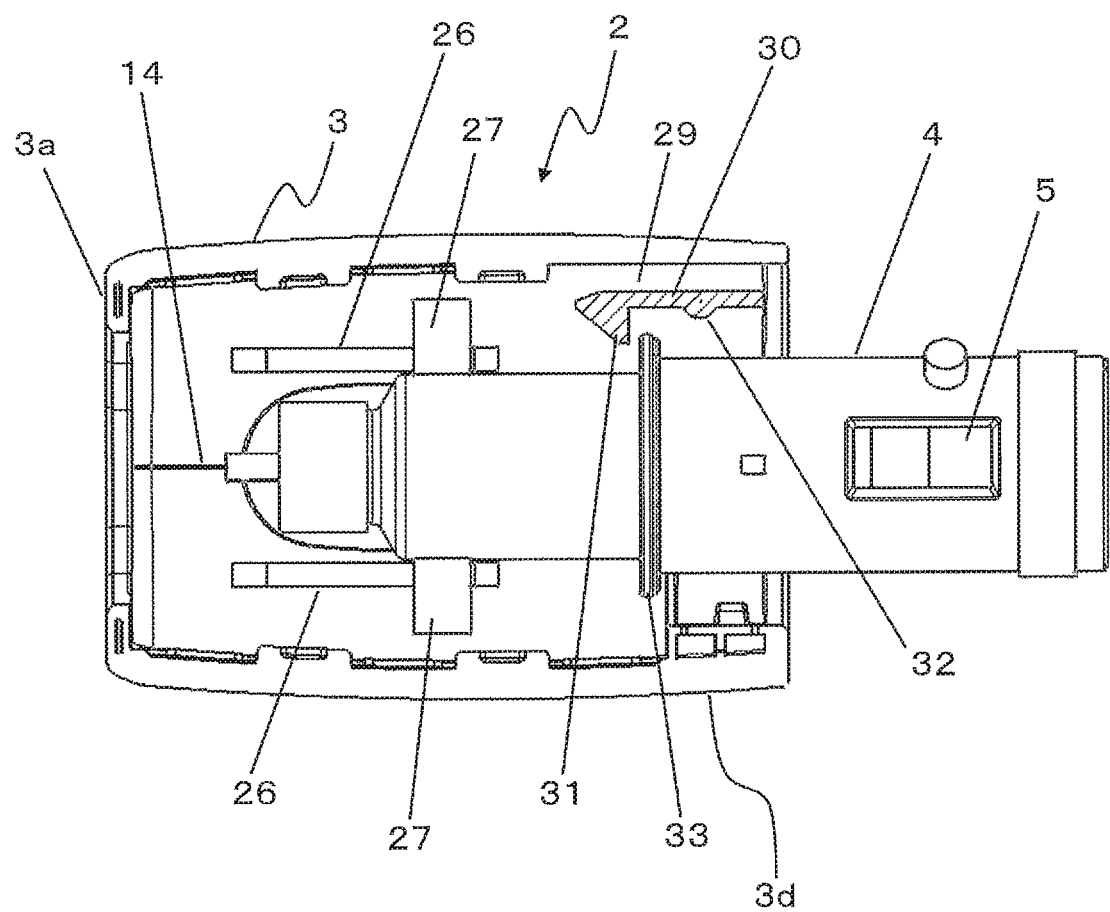
FIG. 18 is a cross section of the mounted state of the injection needle in FIG. 14.
Figure 19:
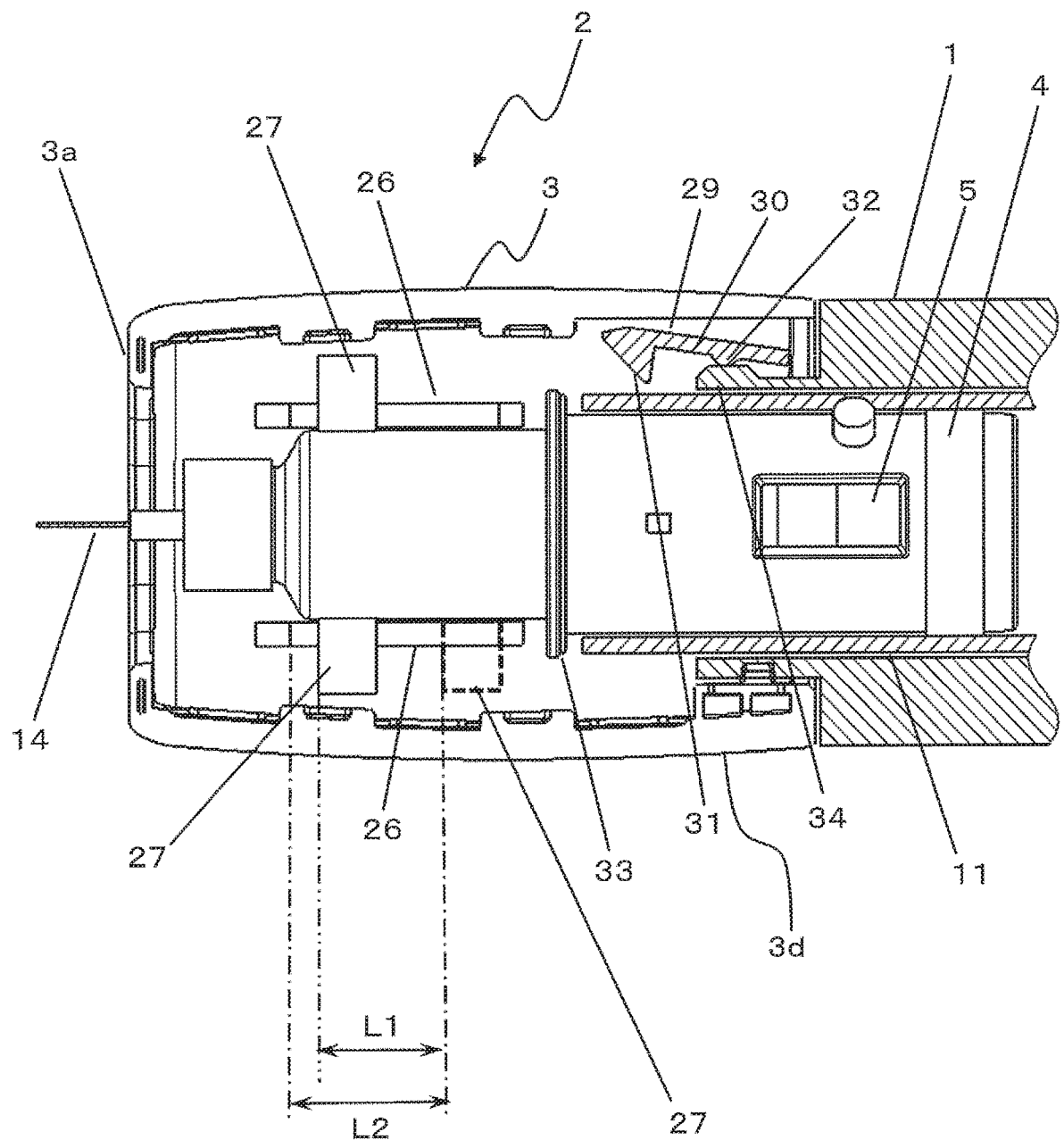
FIG. 19 is a cross section of the mounted state of the injection needle in FIG. 14.

FIG. 18 corresponds to FIG. 16, and FIG. 19 corresponds to FIG. 17. That is, FIG. 18 is the state when the needle cap 36 or the needle case 37 has been removed from the state in FIG. 16, and FIG. 19 shows the state when the needle cap 36 and the needle case 37 have been removed from the state in FIG. 17. As to the rest of the portions, those that are numbered the same have the same configuration.

First, the pharmaceutical syringe unit 2 in a state in which the needle cap 36 or the needle case 37 has been removed from the main body case 1 of the pharmaceutical injection device will be described through reference to FIGS. 16 and 18.

The pharmaceutical syringe unit 2 is made up of the distal end cap 3 and the syringe cover 4, and the pharmaceutical syringe 5 is housed and held in the interior of the syringe cover 4.

The syringe cover 4 that houses and holds the pharmaceutical syringe 5 is held in the distal end cap 3 so that more than half of it goes into the interior of the distal end cap 3. That is, the flanges 27 of the syringe cover 4 are guided by the guide components 26 of the distal end cap 3, and the syringe cover 4 is held in the distal end cap 3 in a state of being able to move in the forward and backward direction. More specifically, the configuration is such that the flanges 27 of the syringe cover 4 are sandwiched between the risers 26a1 and 26a2 constituting the guide components 26, and stay in the recesses 26b1 and 26b2 of the guide components 26.

In FIGS. 16 to 22, the two flanges 27 are guided by the two guide components 26 so as to be sandwiched between two pairs of risers 26a1 and 26a2.

Therefore, the syringe cover 4 is able to slide over the range of the recesses 26b1 and 26b2 forming the guide components 26 (in other words, between the stoppers 60a and 60b).

In removing the pharmaceutical syringe unit 2 from the main body case 1, basically this is performed after the injection needle 14 is covered with the needle case 37 and the injection needle 14 and the needle case 37 are removed, or after the injection needle 14 is covered with the needle case 37.

As shown in FIGS. 16 and 18, the restrictor 29, which restricts the sliding of the syringe cover 4 to the distal end side of the distal end cap 3 in a state in which the distal end cap 3 has been removed (disengaged) from the main body case 1 of the pharmaceutical injection device, is provided to the inside of the rear part of the distal end cap 3.

As discussed above, this restrictor 29 has the catch 30, which is biased to the outer peripheral part side of the syringe cover 4 from the distal end cap 3, and the first protrusion 31 is provided to the distal end portion of this catch 30. When this first protrusion 31 restricts the flange 33 provided around the outside of the syringe cover 4, movement of the syringe cover 4 to the distal end side of the distal end cap 3 is restricted.

With this configuration, in a state in which the flanges 27 of the syringe cover 4 are restricted by the rear end side of the risers 26a (the stopper 60b) of the distal end cap 3, movement of the syringe cover 4 to the distal end side of the flange 33 is restricted by the first protrusion 31 of the catch 30 of the distal end cap 3. As a result, the syringe cover 4 is held in the interior of the distal end cap 3.

Therefore, the injection needle 14 mounted to the needle mounting component 28 at the distal end part of the syringe cover 4 is not exposed from the distal end face 3a on the distal end side of the distal end cap 3, as shown in FIG. 18, which is safer.

When the needle case 37 is mounted as in FIG. 16, part of the needle case 37 is exposed from the distal end face 3a.

This takes into account a situation in which the needle case 37 is removed from the syringe cover 4 while still covering the injection needle 14.

A state in which the pharmaceutical syringe unit 2 has been mounted to the main body case 1 of the pharmaceutical injection device will now be described through reference to FIGS. 17 and 19. The difference between FIGS. 17 and 19 is just whether or not the needle case 37 is mounted to the injection needle 14. FIG. 17 is the state when the needle case 37 is mounted to the injection needle 14, and FIG. 19 is the state when the needle case 37 is not mounted to the injection needle 14.

Any redundant portions that are the same as what was described for FIGS. 16 and 18 above will be omitted here.

FIGS. 17 and 19 show the state when the pharmaceutical syringe unit 2 is mounted to (engaged with) the main body case 1. At this point, a protrusion 34 provided to part of the main body case 1 hits the second protrusion 32 of the catch 30 provided to the inside and to the rear of the distal end cap 3, and the second protrusion 32 is pushed outward by the protrusion 34.

Specifically, when the protrusion 34 of the main body case 1 and the second protrusion 32 of the catch 30 engage, the catch 30 that had been restricting the flange of the syringe cover 4 is pushed outward (in the opposite direction from the axial center direction of the syringe cover 4) as shown in FIGS. 17 and 19.

Along with this, the restriction of the first protrusion 31, which had been holding and restricting the flange 33 of the syringe cover 4, is released, allowing the syringe cover 4 to slide in the range of the guide grooves 26b of the guide components 26 of the distal end cap 3.

Specifically, in a state in which the pharmaceutical syringe unit 2 has been mounted to the main body case 1, the syringe cover 4 to which the injection needle 14 has been mounted is allowed to slide in order to make the needle insertion and withdrawal operations possible. The syringe cover 4 is connected to the inner case 11 of the main body case 1, and the sliding range is restricted by the inner case 11. Therefore, the range of the recesses 26b1 and 26b2 (the range of the guide components 26, or between the stopper 60a and the stopper 60b) should be set slightly greater than the sliding range of the inner case 11.

That is, as shown in FIGS. 13 and 17, when the pharmaceutical syringe unit 2 is mounted to the main body case 1 of the pharmaceutical injection device, the sliding range of the syringe cover 4 is the needle insertion and withdrawal stroke of the pharmaceutical injection device (L1 in FIGS. 13 and 17), is equal to the distance between the sensor 17 and the sensor 18 moved by the slide motor 12, and corresponds to the sliding range of the inner case 11. L1 can also be called the distance between the needle insertion position and the needle withdrawal position.

Meanwhile, the stroke that is the movable range of the guide components 26 (can also be called the range of the recesses 26b1 and 26b2 in the forward and backward direction) is indicated by L2 in FIGS. 17, 19, etc. L2 could also be called the movable range of the syringe cover 4.

L1 and L2 are in the following relation.

$$L2 > L1 \quad (1)$$

Thus, the relation between the stroke of the inner case 11 (L1) and the stroke of the guide components 26 (L2) can be used to make work easier with the needle replacement tool discussed below.

FIGS. 17 and 19 show the needle insertion state. This needle insertion state is one in which the flanges 27 of the syringe cover 4 have moved forward to the front position where they touch the distal end side of the risers 26a of the guide components 26, that is, a state in which the inner case 11 has slid in the needle insertion direction, which is a state in which the injection needle 14 sticks out from the distal end face 3a of the distal end cap 3.

That is, during pharmaceutical injection, this is a state in which the injection needle 14 has punctured the skin, after which the injection of the pharmaceutical can commence.

A needle withdrawal state, as shown in FIGS. 12, 13, 16, and 18, is one in which the flanges 27 of the syringe cover 4 have retracted to a position where they touch the risers 26a on the rear end side of the guide components 26, that is, a state in which the inner case 11 has slid in the needle withdrawal direction, which is a state in which the injection needle 14 is not exposed from the distal end face 3a of the distal end cap 3 at this point. That is, this is a state in which pharmaceutical injection is complete and the injection needle 14 has been withdrawn from the skin. The positions of the flanges 27 at the needle withdrawal position (the position after movement to the rear end side) are indicated by dotted lines in FIGS. 17 and 19.

13. Mounting and Removal of Injection Needle

The method for mounting the needle unit 35 to the needle mounting component 28 of the syringe cover 4 of the pharmaceutical syringe unit 2, and the method for removing the needle case 37 including the injection needle 14 from the needle mounting component 28 will now be described through reference to FIGS. 20 and 21. The positions of the flanges 27 after movement to the rear end side are also indicated by dotted lines in FIGS. 20 and 21.

Usually, as shown in the above-mentioned FIG. 13, the needle unit 35 including the injection needle 14 (made up of the injection needle 14, the needle cap 36, and the needle case 37) is mounted, or the needle case 37 including the injection needle 14 is removed, in a state in which the pharmaceutical syringe unit 2 has been mounted to the main body case 1 of the pharmaceutical injection device, but in the mounting and removal of the injection needle 14, the syringe cover 4 to which the injection needle 14 is mounted is at the needle withdrawal position (the position where it has been retracted all the way from the distal end side), so although mounting and removal are possible, they can hardly be considered convenient.

In view of this, an easy method is given for mounting and removing the injection needle 14 even in a state in which the pharmaceutical syringe unit 2 has been removed from the main body case 1 of the pharmaceutical injection device.

Figure 20:
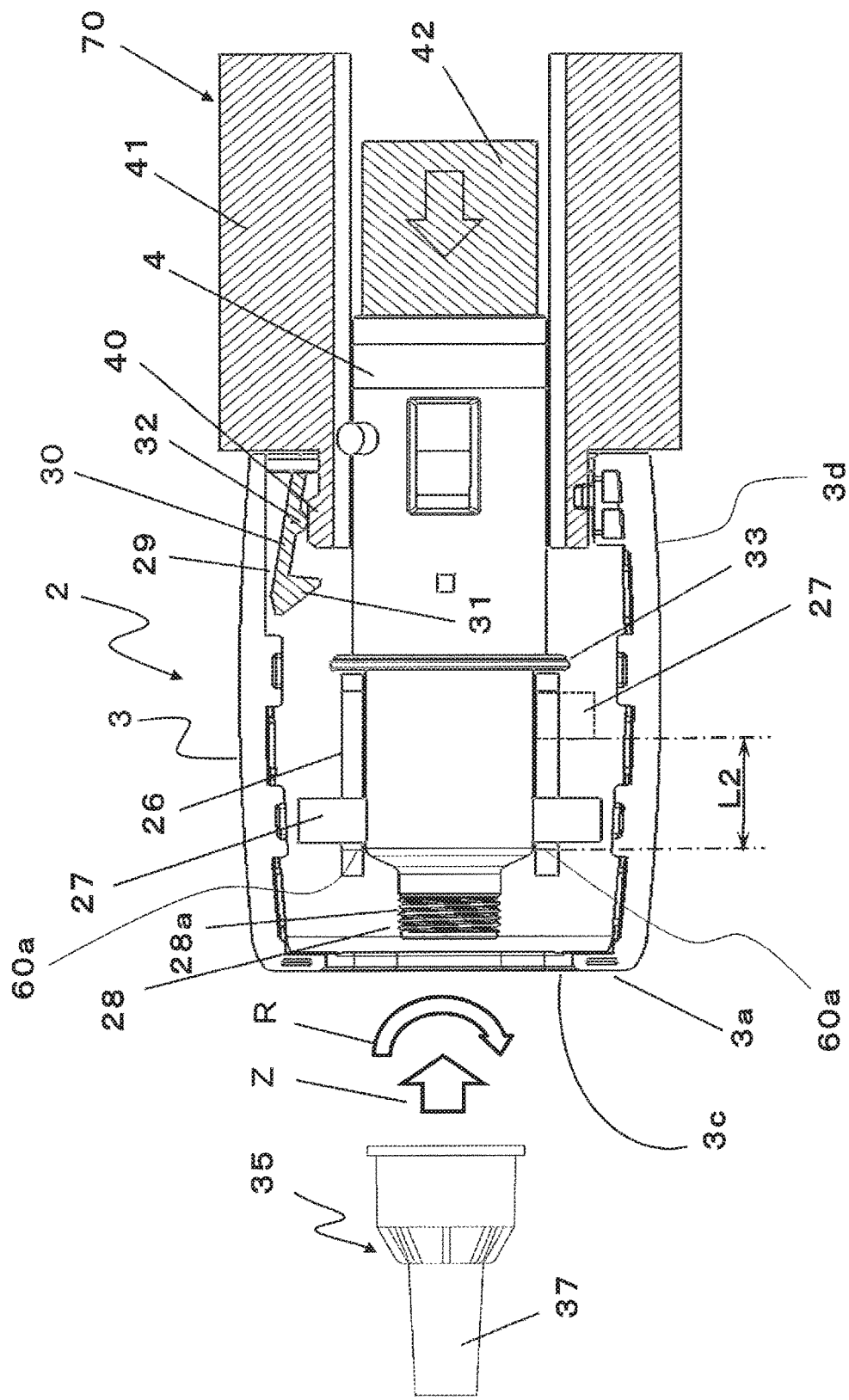
FIG. 20 is a cross section of the method for attaching and removing the needle unit in FIG. 14.

FIG. 20 shows an injection needle mounting and removal tool 70 provided to the storage case (see FIGS. 24 and 25), the housing case of the pharmaceutical injection device, etc. The injection needle mounting and removal tool 70 works as a tool for mounting and removing the injection needle 14 of the pharmaceutical syringe unit 2. The injection needle mounting and removal tool 70 comprises a stationary part 41 (an example of a unit mounting component) on which the pharmaceutical syringe unit 2 is placed, and a sliding part 42 for moving the syringe cover 4.

That is, the purpose of the stationary part 41 is to allow the syringe cover 4 to slide by mounting the pharmaceutical syringe unit 2 and releasing the catch 30 that restricts the syringe cover 4.

The sliding part 42 moves the syringe cover 4, having the needle mounting component 28 to which the injection needle 14 is mounted, to the distal end side by moving the sliding part 42 in the distal end direction after the holding of the syringe cover 4 in the pharmaceutical syringe unit 2 has been released and it is made able to slide by the stationary part 41.

Specifically, just as with the main body case 1, the stationary part 41 is provided with a protrusion 40 for releasing the engagement of the syringe cover 4 with the flange 33 by moving the catch 30 provided on the inside of the distal end cap 3 constituting the pharmaceutical syringe unit 2 outward (the opposite direction from the direction facing the axial center of the syringe cover 4). When the pharmaceutical syringe unit 2 is mounted to the stationary part 41, the protrusion 40 pushes the second protrusion 32 provided to the catch 30, which causes the catch 30 to move so as to spread outward, and as a result the first protrusion 31 of the catch 30 removes the restriction of the flange 33 of the syringe cover 4. Consequently, the syringe cover 4, which has the needle mounting component 28 to which the injection needle 14 is mounted, is able to slide over a specific range of the guide components 26.

After this, the sliding part 42 is slid to the distal end side, which moves the syringe cover 4 to the distal end face 3a side of the distal end cap 3.

At this point, the flanges 27 of the syringe cover 4 have moved to the position where they touch the risers 26a on the distal end side of the guide components 26 (the position where they touch the stopper 60a) (stroke L2) as shown in FIG. 20, which makes it easy to attach or remove the needle case 37 or the needle unit 35 including the injection needle 14. As mentioned above, L2 is the stroke of the guide components 26 (the recesses 26b1 and 26b2), and is the movable range of the syringe cover 4.

More specifically, when the injection needle 14 is mounted to the needle mounting component 28 of the syringe cover 4, if the needle unit 35 including the injection needle 14 is inserted in the direction of the arrow Z and turned to the right (clockwise) in the direction of the arrow R, the female threads 38b of the needle base 38 of the injection needle 14 housed in the interior of the needle unit 35 will mesh with the male threads 28a of the needle mounting component 28 (see FIG. 20), so the mounting is simple.

Also, when the injection needle 14 is removed from the needle mounting component 28, the needle case 37 is grasped and placed over the injection needle 14 mounted to the needle mounting component 28, after which the male threads 28a of the needle mounting component 28 are unthreaded from the female threads 38b of the injection needle 14 by turning in the opposite direction from the arrow R (counter-clockwise), and the injection needle 14 goes into the needle case 37. The injection needle 14 can then be simply removed by pulling out the needle case 37 in the opposite direction from the arrow Z.

In this case, since the protrusions 37a provided around the inside of the needle case 37 engage with the textured part 38a provided around the outside of the needle base 38 constituting the injection needle 14, the injection needle 14 rotates along with the needle case 37, and mounting and removal with the needle mounting component 28 can be carried out easily (see FIG. 15).

Figure 21:
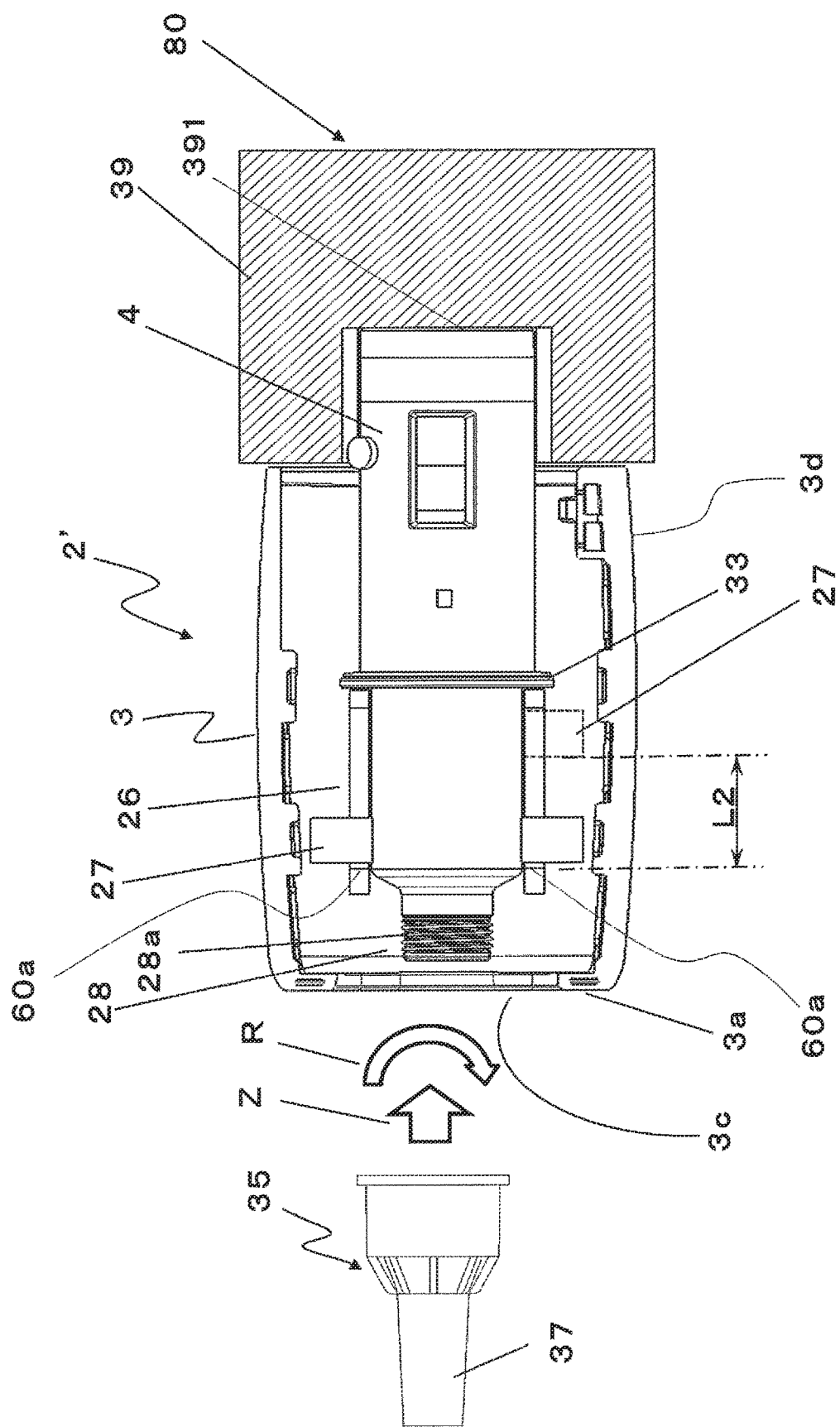
FIG. 21 is a cross section of the method for attaching and removing the needle unit in FIG. 14.

Next, a modification example that is a simplified version of the present invention is shown in FIG. 21.

The pharmaceutical syringe unit 2' shown in FIG. 21 does not have the restrictor 29 had by the pharmaceutical syringe unit 2 shown in FIG. 20, which restricts the flange 33 of the syringe cover 4.

However, just as with the pharmaceutical syringe unit 2 in FIG. 20, the pharmaceutical syringe unit 2' comprises a distal end cap 3 having openings on the distal end side and the rear end side, and a syringe cover 4 that is held in this distal end cap 3 in a state of being able to slid forward and backward, and the distal end cap 3 is provided with guide components 26 that slide the syringe cover 4 forward and backward over a specific range. Therefore, the syringe cover 4 that can include a pharmaceutical syringe can slide over a range of L2, which is the stroke of the guide components 26, but will not come loose from the distal end cap 3.

In the example in FIG. 21, a stationary part 39 (an example of a unit mounting component) that works as a tool for mounting and removing the injection needle 14 of this pharmaceutical syringe unit 2' is provided to the storage case (see FIGS. 24 and 25), the housing case of the pharmaceutical injection device, etc.

When the pharmaceutical syringe unit 2' is mounted to this stationary part 39, the syringe cover 4 hits the distal end side of the guide components 26 of the distal end cap 3 (that is, the flanges 27 of the syringe cover 4 are in contact with the risers 26a on the distal end side of the guide components 26 (see FIG. 17, etc.) (this can also be called a state of being in contact with the stopper 60a), allowing the needle case 37 or the needle unit 35 including the injection needle 14 to be mounted and removed easily.

The center portion of this stationary part 39 is formed in a concave shape, and the bottom portion thereof functions as a slide component 391 that slides the syringe cover 4 forward. Specifically, when the pharmaceutical syringe unit 2 is disposed in the stationary part 39, the rear end of the syringe cover 4 is pushed forward by the slide component 391, and the syringe cover 4 moves forward. By adjusting the depth of the concave shape here, the flanges 27 of the syringe cover 4 can be moved in the direction of the stopper 60a when the pharmaceutical syringe unit 2 has been disposed in the stationary part 39.

That is, just as discussed above about FIG. 20, when the injection needle 14 is mounted to the needle mounting component 28 of the syringe cover 4, if the needle unit 35 including the injection needle 14 is inserted in the direction of the arrow Z and turned to the right (clockwise) in the direction of the arrow R, the female threads 38b of the needle base 38 of the injection needle 14 housed in the interior of the needle unit 35 will mesh with the male threads 28a of the needle mounting component 28 (see FIG. 15), so the mounting of the injection needle 14 is simple.

Also, when the injection needle 14 is removed from the needle mounting component 28, the needle case 37 is grasped and placed over the injection needle 14 mounted to the needle mounting component 28, after which the male threads 28a of the needle mounting component 28 are unthreaded from the female threads 38b of the injection needle 14 by turning in the opposite direction from the arrow R (counter-clockwise), and the injection needle 14 goes into the needle case 37. The injection needle 14 can be simply removed by pulling out the needle case 37 in the opposite direction from the arrow Z.

The method for mounting the needle unit 35 to the pharmaceutical syringe unit 2, and for removing the injection needle 14 from the pharmaceutical syringe unit 2 with using the needle case 37 when the injection operation is finished, as well as the efficacy thereof, will now be described through reference to FIG. 22.

Figure 22:
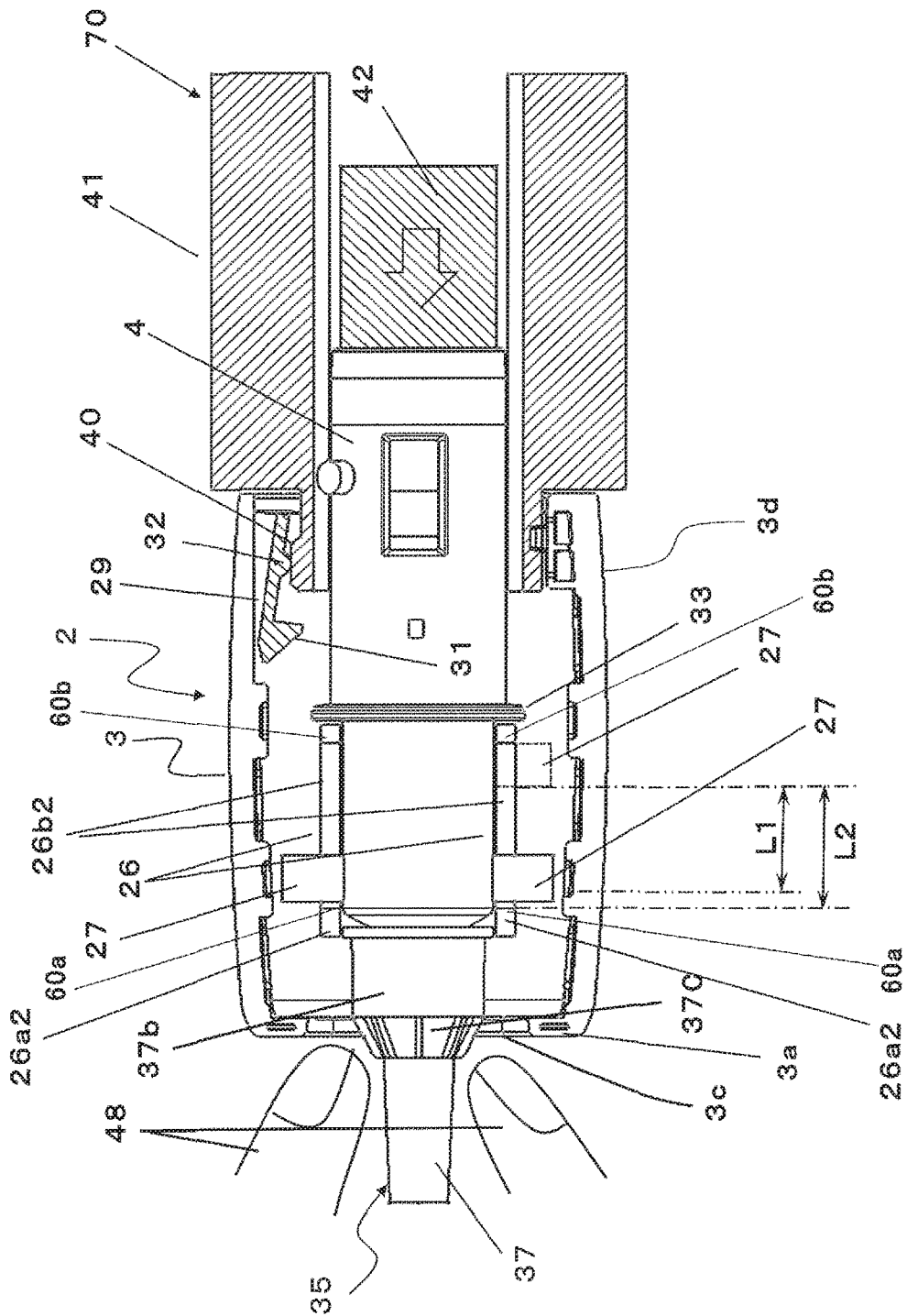
FIG. 22 is a cross section of the method for attaching and removing the needle unit in FIG. 14.

FIG. 22 is similar to FIG. 20 discussed above in that it shows the state when the rear end part of the pharmaceutical syringe unit 2 (made up of the syringe cover 4 including the pharmaceutical syringe 5, and the distal end cap 3 that covers this syringe cover 4; see FIGS. 10A and 10B) has been mounted to the stationary part 41 had by a dedicated injection needle mounting and removal tool 70, or an injection needle replacement mechanism provided to the housing case, etc., of the pharmaceutical injection device or the storage case (see FIGS. 24 and 25), and the needle unit 35 (made up of the injection needle 14, the needle cap 36, and the needle case 37; see FIGS. 14 and 15) has been mounted to the needle mounting component 28 of the syringe cover 4 disposed inside the pharmaceutical syringe unit 2 in a state in which the sliding part 42 has been slid to the distal end side.

FIG. 22 also shows the state when the pharmaceutical syringe unit 2 has been removed from the pharmaceutical injection device and mounted to the stationary part 41 after the injection of the pharmaceutical is complete, the sliding part 42 has been slid to the distal end side, and the needle case 37 has covered the injection needle 14 in this state. Again in FIG. 22, the positions of the flanges 27 after movement to the rear end side are indicated by dotted lines.

The position of the syringe cover 4 in this state, as shown in FIG. 22, is such that the protrusion 40 provided on the stationary part 41 side comes into contact with the second protrusion 32 provided on the side of the restrictor 29 provided around the outside of the distal end cap 3, and the restrictor 29 is pushed in the outer peripheral direction, which disengages the flange 33 of the syringe cover 4 from the first protrusion 31 of the restrictor 29, and causes the syringe cover 4 to move to the distal end side.

In a state in which the pharmaceutical syringe unit 2 in FIGS. 20 and 22 has been mounted to the stationary part 41 of the injection needle mounting and removal tool 70, and the sliding part 42 has slid to the distal end side, the syringe cover 4 is moved to the distal end side, the flanges 27 provided to the syringe cover 4 slide through the guide components 26 provided in the interior of the distal end cap 3, and the flanges 27 come into contact with the risers 26a (the stopper 60a) on the distal end side.

Thus, in the state in FIG. 22, the syringe cover 4 is able to slide over the entire range of the guide components 26. That is, the syringe cover 4 slides over the range of the sliding stroke (L2) of the guide components 26 shown in FIG. 22.

Meanwhile, when the pharmaceutical syringe unit 2 has been mounted to the main body case 1 of the pharmaceutical injection device, the inner case 11 slides over the range of the stroke (L1) of the slide motor 12. Therefore, the syringe cover 4 mounted to the inner case 11 does not hit the riser 26a (stopper 60a) on the distal end side of the guide components 26 (see FIG. 17, etc.).

Because of the relation in which the stroke L2 of the guide components 26 is greater than the stroke L1 of the slide motor 12, the stroke L2 when the syringe cover 4 is mounted to the stationary part 41 can protrude more to the distal end side than the stroke L2 when the syringe cover 4 is mounted to the pharmaceutical injection device (in this example, L2 is about 2 mm longer, but anywhere between 1 and 10 mm is effective).

Specifically, the needle unit 35 and so forth will be more exposed from the distal end face 3a of the distal end cap 3 to the outside, through the distal end opening 3c, when the pharmaceutical syringe unit 2 is mounted to the stationary part 41 than when it is mounted to the pharmaceutical injection device.

Therefore, as shown in FIG. 22, the job of mounting the needle unit 35 to the needle mounting component 28 of the syringe cover 4 can be done by using the fingers 48 to grab the knurled part 37c of the needle case 37 constituting the needle unit 35. This knurled part 37c has an inclined portion in which the diameter gradually increases toward the large-diameter part 37b whose diameter is larger than the slender distal end portion of the needle case 37, and convex parts that provide grip to the fingers 48, so it is easy to grasp with the fingers 48 and can be easily turned with the fingers 48 when it is time to replace the injection needle 14.

Similarly, upon completion of the pharmaceutical injection, when the pharmaceutical syringe unit 2 is removed from the pharmaceutical injection device and mounted to the stationary part 41 of the injection needle mounting and removal tool 70 or to an injection needle replacement mechanism provided to the storage case or the housing case of the pharmaceutical injection device, the syringe cover 4 will slide over the stroke range L2 along with the sliding of the sliding part 42. Accordingly, just as when the needle unit 35 is mounted, the sliding part 42 is slid to the distal end side, and the flanges 27 of the syringe cover 4 are moved to the position where they hit the risers 26a (stopper 60a) on the distal end side of the guide components 26, and in this state the knurled part 37c is grabbed by the fingers 48 (the entire needle case 37 covering the injection needle 14) and rotated in the opposite direction from that during mounting (counter-clockwise), which allows the injection needle 14 covered with the needle case 37 to be easily removed, and it can be simply discarded in this state.

The pharmaceutical syringe unit 2' shown in FIG. 23 will now be described.

Figure 23:
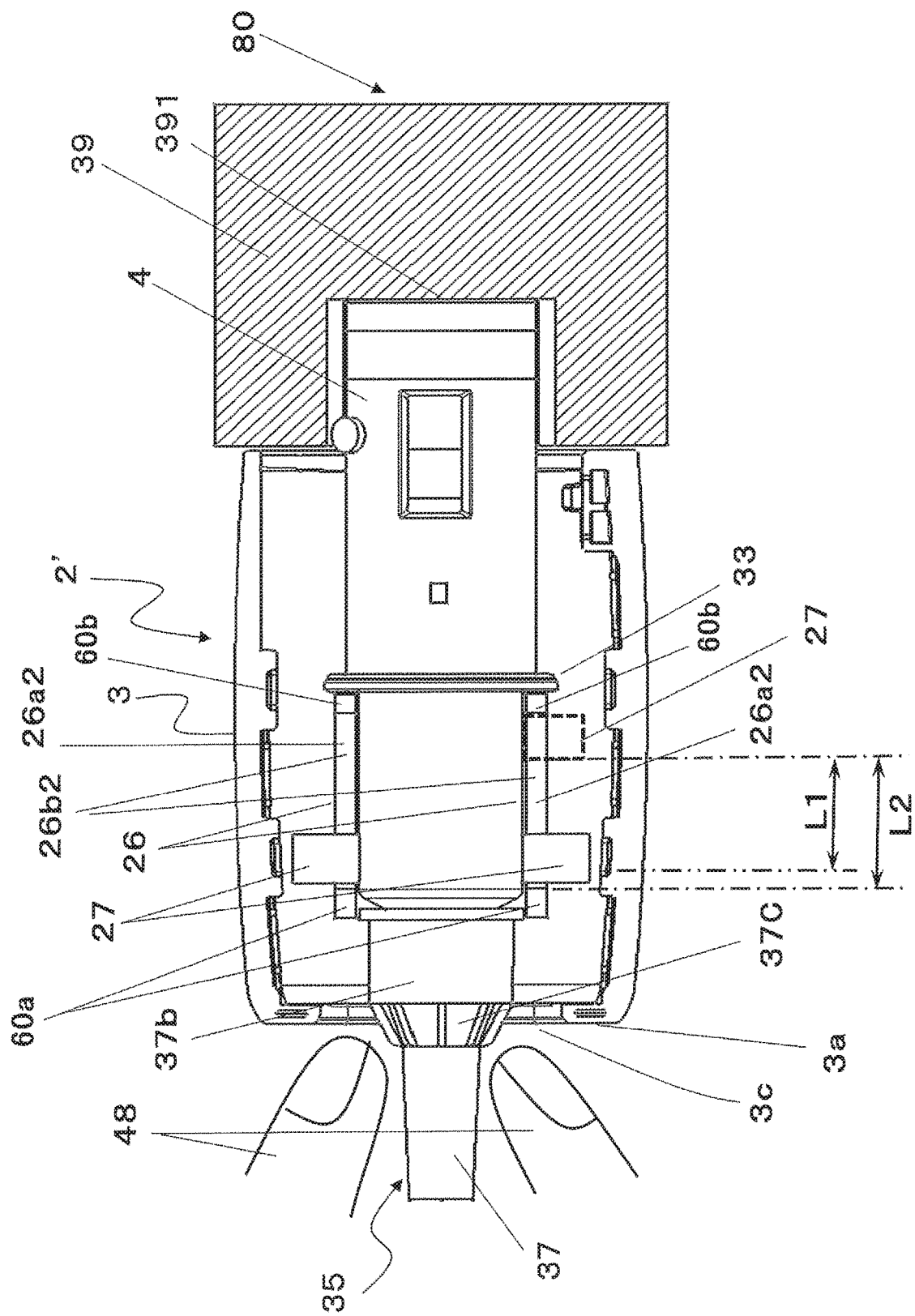
FIG. 23 is a cross section of the method for attaching and removing the needle unit in FIG. 14.

FIG. 23 shows an example in which the simplified pharmaceutical syringe unit 2' illustrated in FIG. 21 is mounted to the stationary part 39 of an injection needle mounting and removal tool 80 or simplified injection needle replacement mechanism provided to a storage case (see FIGS. 24 and 25), etc.

The pharmaceutical syringe unit 2' does not have the restrictor 29, and the injection needle replacement mechanism is just the stationary part 39, with no sliding part 42 being provided as in FIGS. 20 and 22.

In FIG. 23, when the pharmaceutical syringe unit 2' is mounted to the stationary part 39, the syringe cover 4 moves to the distal end side of the guide components 26 of the distal end cap 3 (when the stroke of the guide components 26 is L2, the flanges 27 of the syringe cover 4 are in the position where they hit the risers 26a (the stopper 60a) on the distal end side of the guide components 26), and the needle unit 35 or the needle case 37 including the injection needle 14 can be easily replaced. Again in FIG. 23 the positions of the flanges 27 after movement to the rear end side are indicated by dotted lines.

Specifically, the needle unit 35 or the needle case 37 is more exposed from the distal end face 3a of the distal end cap 3 to the outside, through the distal end opening 3c, when the pharmaceutical syringe unit 2' is mounted to the stationary part 41 than when it is mounted to the pharmaceutical injection device.

Therefore, when the needle unit 35 is mounted to the needle mounting component 28 of the syringe cover 4 constituting the pharmaceutical syringe unit 2', as shown in FIG. 23, the fingers 48 can easily grab the knurled part 37c of the needle case 37, and this part can be easily turned with the fingers 48 when it is time to replace the injection needle 14.

Similarly, upon completion of the pharmaceutical injection, when the pharmaceutical syringe unit 2' is removed from the pharmaceutical injection device and mounted to the stationary part 39, the knurled part 37c is grabbed by the fingers 48 (the entire needle case 37 covering the injection needle 14) and rotated in the opposite direction from that during mounting (counter-clockwise), which allows the injection needle 14 covered with the needle case 37 to be easily removed, and it can be simply discarded in this state.

As discussed above, with certain implementations of the present invention, when the pharmaceutical syringe unit 2' (or the pharmaceutical syringe unit 2) has been removed from the pharmaceutical injection device, the movable range of the syringe cover 4 expands (in other words, the syringe cover 4 can move farther forward), which makes it extremely easy to replace the injection needle 14, the needle unit 35, and the needle case 37.

14. Storage Case

An example in which the needle replacement tool of an implementation of the present invention is applied to a storage case will now be described through reference to FIGS. 24A to 24D and FIGS. 25A to 25C.

Figure 24A:
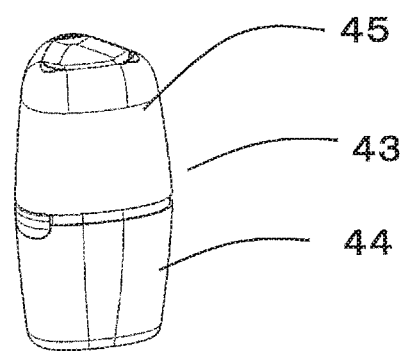
FIG. 24A is an oblique view of the mounting method for a pharmaceutical syringe unit and needle unit using the storage case for the pharmaceutical syringe unit shown in FIG. 5.

FIGS. 24A to 24D are oblique views of the procedure for mounting the needle unit 35 to the pharmaceutical syringe unit 2' (or the pharmaceutical syringe unit 2) and then mounting the pharmaceutical syringe unit 2' to the pharmaceutical injection device. FIG. 24A is an oblique view of a storage case 43 in which the pharmaceutical syringe unit 2' is housed. The storage case 43 is made up of a base component 44 and a lid 45.

Figure 24B:
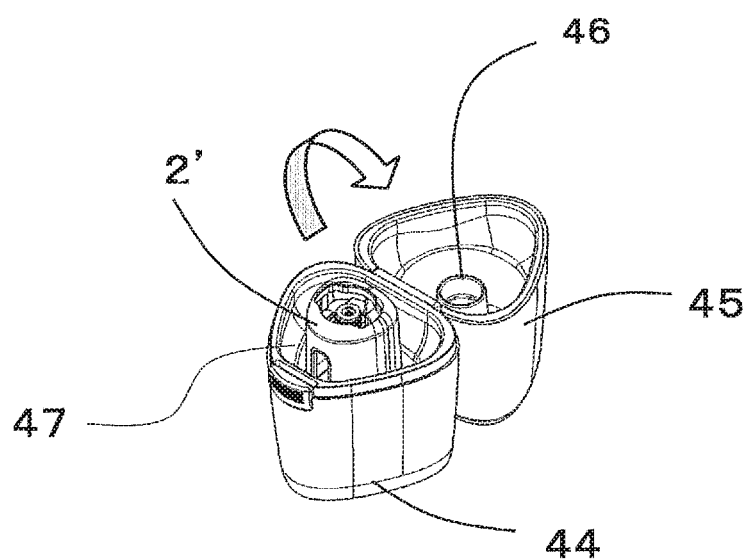
FIG. 24B is an oblique view of the mounting method for a pharmaceutical syringe unit and needle unit using the storage case for the pharmaceutical syringe unit shown in FIG. 5.

FIG. 24B shows the state when the lid 45 of the storage case 43 has been opened in the arrow direction (upward). The pharmaceutical syringe unit 2' including the pharmaceutical syringe 5 and the syringe cover 4 is inside the base component 44.

On the inside of the lid 45 is provided a needle case holder 46, which is used to store the needle case 37 used to cover the injection needle 14 after injection, and is left off during pharmaceutical injection. The needle case 37 is placed in the needle case holder 46 during the pharmaceutical injection work.

Furthermore, a pharmaceutical syringe unit housing 47 that houses the pharmaceutical syringe unit 2' (or the pharmaceutical syringe unit 2) is provided in the interior of the base component 44.

This pharmaceutical syringe unit housing 47 has the injection needle mounting and removal tool 80 shown in FIGS. 21 and 23.

After the lid 45 is opened, the needle unit 35 is mounted to the needle mounting component 28 of the syringe cover 4 constituting the pharmaceutical syringe unit 2'.

Figure 24C:
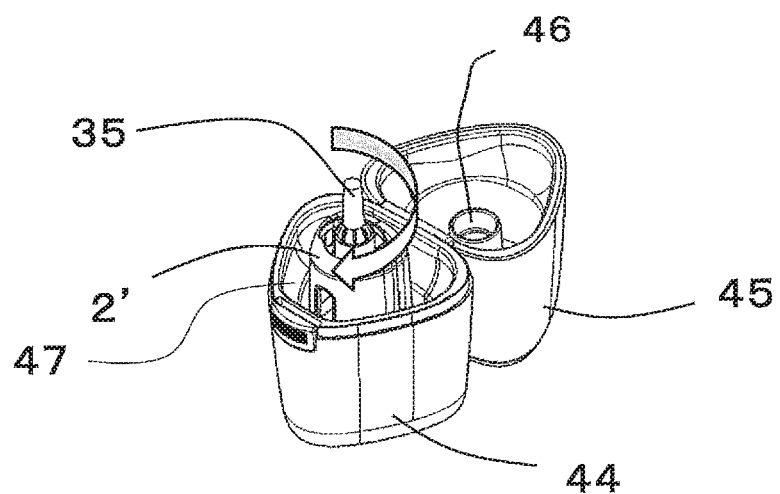
FIG. 24C is an oblique view of the mounting method for a pharmaceutical syringe unit and needle unit using the storage case for the pharmaceutical syringe unit shown in FIG. 5.

In this case, the female threads 38b provided around the inside of the needle base 38 of the injection needle 14 constituting the needle unit 35 are engaged with the male threads 28a of the needle mounting component 28 provided on the distal end side of the syringe cover 4 by turning in the direction of the arrow shown in FIG. 24C (clockwise), and this mounts the needle unit 35 to the pharmaceutical syringe unit 2 (see FIGS. 15, 21, etc.).

Here, the state in FIGS. 24B and 24C is the same as the state in the cross sections shown in FIGS. 21 and 23.

Specifically, when the pharmaceutical syringe unit 2' is mounted to the stationary part 39 provided to the lower part of the pharmaceutical syringe unit housing 47, the syringe cover 4 having the needle mounting component 28 to which the injection needle 14 is mounted is slid (moved) to the distal end side of the guide components 26 (in the example in FIG. 21 or 23, to the position where the flanges 27 of the syringe cover 4 hit the risers 26a on the distal end side of the guide components 26).

In a state in which the pharmaceutical syringe unit 2' is stored in the pharmaceutical syringe unit housing 47, just as in FIG. 21, the syringe cover 4 is pushed out by the stationary part 39 in the distal end direction, and moves to the position where the flanges 27 of the syringe cover 4 hit the risers 26a (the stopper 60a) on the distal end side of the guide components 26 provided in the distal end cap 3 (this means it moves by the distance L2 shown in FIG. 21 to the distal end side).

This distance is greater than the movement range L1 in a state of being mounted to the pharmaceutical injection device. Therefore, the needle unit 35 or the needle case 37 is in a state of sticking out more to the distal end face 3a side of the distal end cap 3, so the needle unit 35 or the needle case 37 can be easily mounted.

Then, the pharmaceutical syringe unit 2' to which the needle unit 35 is mounted is itself mounted on the distal end side of the main body case 1 of the pharmaceutical injection device.

That is, the protrusions 4a provided around the outside on the rear end side of the syringe cover 4 engage with the L-shaped grooves 11a of the inner case 11 in the main body case 1, and are fixed there (see FIG. 6).

Figure 24D:
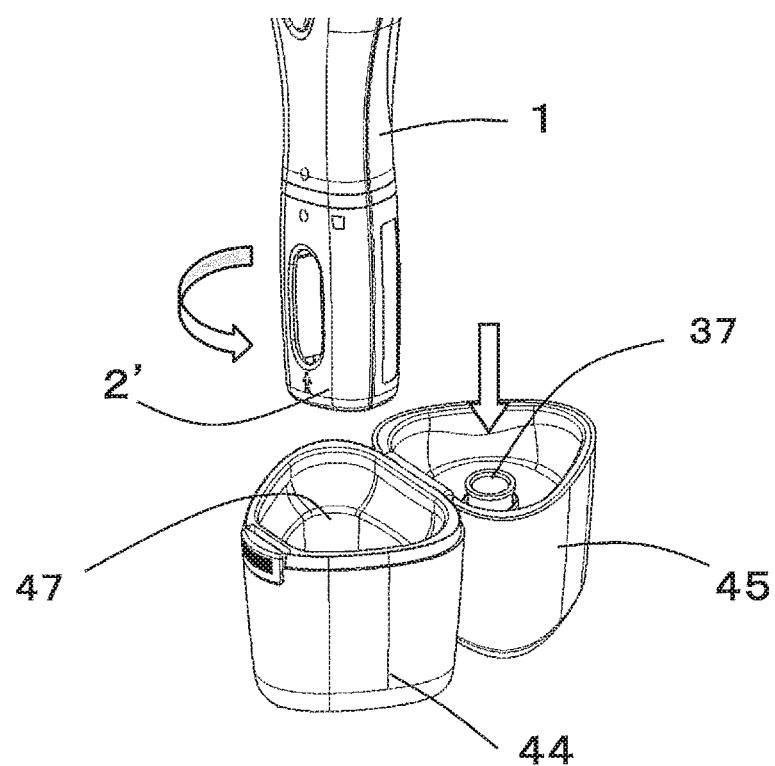
FIG. 24D is an oblique view of the mounting method for a pharmaceutical syringe unit and needle unit using the storage case for the pharmaceutical syringe unit shown in FIG. 5.

That is, the pharmaceutical syringe unit 2' (or the pharmaceutical syringe unit 2) is inserted from the distal end side of the pharmaceutical injection device, after which it is rotated in the direction indicated by the arrow in FIG. 24D to mount and fix the pharmaceutical syringe unit 2' to the pharmaceutical injection device.

At this point, the protrusions 3b provided to the inner peripheral part of the distal end cap 3 are engaged with the main body grooves 1*a* provided on the distal end side of the main body case (see FIGS. 6 and 10).

After this, the needle case 37 constituting the needle unit 35 is removed, and the needle case 37 is stored in the needle case holder 46 inside the lid 45.

In this case, the needle case 37 is placed with the distal end side facing down, which stabilizes the case and affords easy work when it is remounted to the injection needle 14 after injection.

Furthermore, the injection needle 14 is exposed when the needle cap 36 is removed, but at this point, the position of the inner case 11 of the pharmaceutical injection device is retracted to the needle withdrawal position (the position of the sensor 18 in FIG. 3), so the injection needle 14 does not protrude to the front side from the distal end face 3*a* of the distal end cap 3.

As discussed above, once preparation for pharmaceutical injection is complete, the power button 6 on the pharmaceutical injection device is pressed to turn on the power. This turning on of the power may be done before the above-mentioned removal of the needle case 37.

After this, the air expel button 8 is pressed to expel any air bubbles as needed.

The distal end side of the pharmaceutical injection device (the distal end face 3*a* of the distal end cap 3) is then placed against the injection site, and the inject button 7 provided to the main body case 1 of the pharmaceutical injection device is pressed to carry out the series of injection operations discussed above.

Specifically, when the inject button 7 is pressed, the controller 20 of the pharmaceutical injection device drives the slide motor 12 via the motor drive circuit 16, and moves the inner case 11 in the distal end direction.

Consequently, the syringe cover 4 mounted on the distal end side of the inner case 11 also moves to the distal end side, and along with this the injection needle 14 mounted to the needle mounting component 28 at the distal end part of the syringe cover 4 sticks out from the distal end opening 3*c* of the distal end cap 3, and punctures the skin. In FIG. 3, the slide motor 12 is halted upon sensing that the sensor 17 has been blocked by the blocking plate 50. This constitutes the needle insertion operation.

After the injection needle 14 has been inserted into the skin, the controller 20 then drives the piston drive motor 15 via the motor drive circuit 16, moves the piston 13 to the distal end side, and pushes the rear end 5*a* of the pharmaceutical syringe 5 housed in the interior through the rear opening 4*b* (piston insertion opening) at the rear end of the syringe cover 4.

When the rear end 5*a* of the pharmaceutical syringe 5 is thus pushed to the distal end side by the piston 13, the pharmaceutical is injected from the injection needle 14 into the body.

Once the piston 13 is moved by an amount corresponding to the preset injection amount, the controller 20 halts the piston drive motor 15 (this also stops the piston 13). This is the injection operation.

The controller 20 then drives the slide motor 12 via the motor drive circuit 16 to move the inner case 11 in the rear end direction.

Consequently, the syringe cover 4 mounted on the distal end side of the inner case 11 also moves to the rear end side, and along with this the injection needle 14 mounted to the needle mounting component 28 at the distal end part of the syringe cover 4 is withdrawn from the skin. In FIG. 3, the slide motor 12 is halted when the blocking plate 50 moves from the sensor 17 and it is sensed that it is blocking the sensor 18. This is the needle withdrawal operation. Once this needle withdrawal operation is complete, the distal end of the injection needle 14 no longer protrudes from the distal end face of the distal end cap 3.

The method for removing the injection needle 14, etc., after completion of the above-mentioned series of jobs consisting of the needle insertion operation, the injection operation, and the needle withdrawal operation will now be described.

Figure 25A:
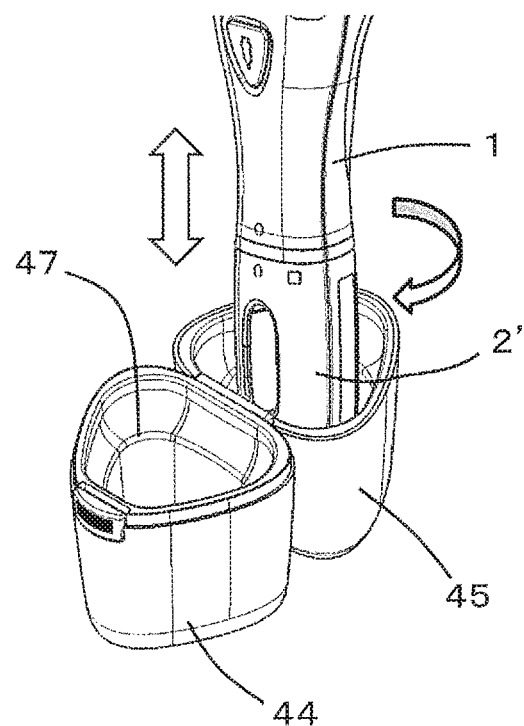
FIG. 25A is an oblique view of the method for removing the injection needle shown in FIG. 14 and the pharmaceutical syringe unit shown in FIG. 5.
Figure 25B:
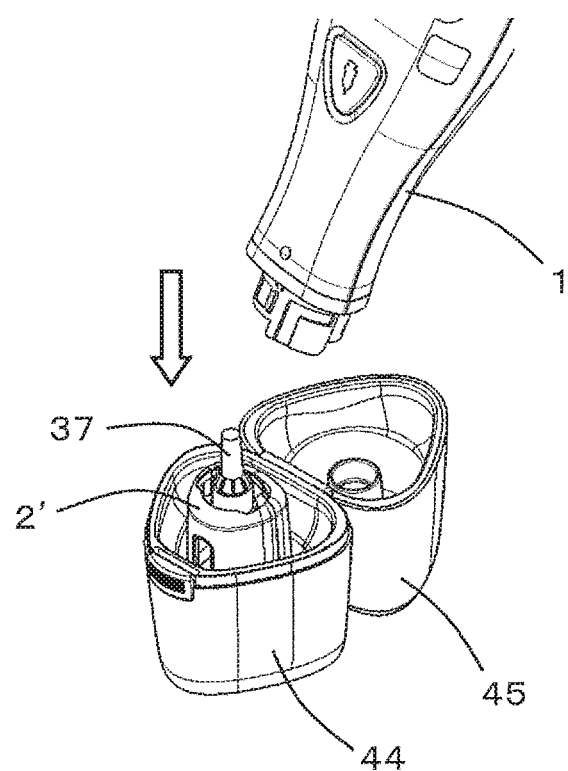
FIG. 25B is an oblique view of the method for removing the injection needle shown in FIG. 14 and the pharmaceutical syringe unit shown in FIG. 5.
Figure 25C:
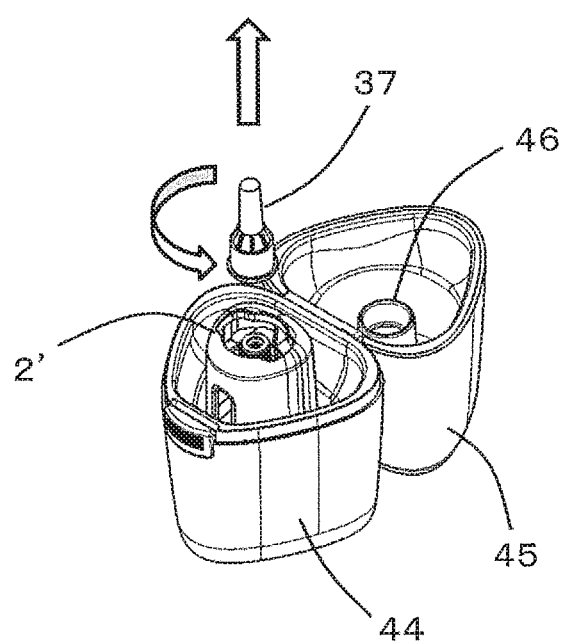
FIG. 25C is an oblique view of the method for removing the injection needle shown in FIG. 14 and the pharmaceutical syringe unit shown in FIG. 5.

FIGS. 25A, 25B, and 25C are oblique views of the procedure in which the pharmaceutical syringe unit 2' (or the pharmaceutical syringe unit 2) is removed from the pharmaceutical injection device, after which the injection needle 14 is removed from the pharmaceutical syringe unit 2'.

The user removes the distal end cap 3 of the pharmaceutical injection device from where he had placed it against his skin, and pushes the distal end side of the pharmaceutical injection device in and downward in the state which the distal end side of the pharmaceutical injection device is toward the needle case 37 located in the needle case holder 46 shown in FIG. 24D.

Specifically, since the injection needle 14 is mounted on the distal end side of the pharmaceutical injection device, the injection needle 14 is covered by the needle case 37.

In this case, the needle case 37 is such that its diameter at the rear end gradually increases from the distal end portion, the large-diameter part 37*b* is located at the rear end portion, and the injection needle 14 is inserted from the rear end side on which this large-diameter part 37*b* is provided, so even in a state in which the injection needle 14 has been mounted to the pharmaceutical injection device, the injection needle 14 can be easily covered with the needle case 37 (see FIG. 25A). Also, the external shape of the pharmaceutical syringe unit 2' (or the pharmaceutical syringe unit 2) is guided by the shape provided on the inside of the lid 45 of the storage case 43, which makes operation even easier.

After this, the pharmaceutical injection device is pulled straight up as shown in FIG. 25A, the pharmaceutical syringe unit 2' (or the pharmaceutical syringe unit 2) is turned in the rotation direction shown in FIG. 25A (the opposite direction from the direction shown in FIG. 24D) in a state in which the injection needle 14 is covered by the needle case 37, and the pharmaceutical syringe unit 2' is removed from the pharmaceutical injection device.

Specifically, the protrusions 4*a* provided around the outside on the rear end side of the syringe cover 4 are disengaged from the L-shaped grooves 11*a* of the inner case 11 inside the main body case 1, and this releases the fixing (see FIG. 6).

Also at this point, the protrusions 3*b* provided to the inner peripheral part of the distal end cap 3 are disengaged from the main body grooves 1*a* provided on the distal end side of the main body case 1 (see FIGS. 6 and 10).

The removed pharmaceutical syringe unit 2' (in a state in which the injection needle 14 mounted on the distal end side is covered by the needle case 37) is placed with its distal end side facing up (with the needle case 37 facing up) in the pharmaceutical syringe unit housing 47 inside the base component 44 (see FIG. 25B).

After this, the needle case 37 is turned in the direction of the arrow shown in FIG. 25C (counter-clockwise; the opposite direction from the rotation direction shown in FIG. 24C) to remove the needle case 37 and the injection needle 14 that it covers from the pharmaceutical syringe unit 2'.

Specifically, when the needle case 37 is turned counter-clockwise, the injection needle 14 rotates along with the needle case 37, the female threads 38*b* provided around the inside of the needle base 38 of the injection needle 14 are disengaged from the male threads 28a of the needle mounting component 28 provided on the distal end side of the syringe cover 4, and as a result the injection needle 14 that is covered by the needle case 37 is removed from the pharmaceutical syringe unit 2' (see FIGS. 15, 21, etc.).

Here, the state in FIGS. 25B and 25C is the same as the state in the cross section shown in FIGS. 21 and 23. The pharmaceutical syringe unit 2' is mounted to the stationary part 39 provided at the lower part of the pharmaceutical syringe unit housing 47, and as a result the syringe cover 4 having the needle mounting component 28 to which the injection needle 14 is mounted is slid (moved) to the distal end side (in the example in FIGS. 21 and 23, to a position where the flanges 27 of the syringe cover 4 hit the risers 26a (the stopper 60a) on the distal end side of the guide components 26).

Therefore, in the state in which the pharmaceutical syringe unit 2' in FIGS. 25B and 25C are stored in the pharmaceutical syringe unit housing 47, the syringe cover 4 is pushed in the distal end direction by the stationary part 39 just as in FIG. 21 or 23, and moves to the position where the flanges 27 of the syringe cover 4 hit the risers 26a (the stopper 60a) on the distal end side of the guide components 26 provided inside the distal end cap 3 (moves to the distal end side by a distance of L2 as shown in FIG. 21 or 23).

The movement range (stroke) L2 of the guide components 26 is greater than the movement range L1 in a state of having been mounted to the pharmaceutical injection device. Therefore, this is a state of projecting more to the distal end face 3a of the distal end cap 3, so the needle case 37 can be easily removed.

After this, the needle case 37 including the injection needle 14 may be discarded, making this product extremely good in terms of both being easy to use and being hygienic.

Specifically, in this embodiment, because the sliding range (L2) of the syringe cover 4 within the distal end cap 3 is greater than the distance (L1) between the needle insertion position and the needle withdrawal position of the pharmaceutical injection device, when the injection needle is mounted or removed, the needle case 37 can be exposed up to the large-diameter part 37b and the knurled part 37c, which are away from the center axis of the injection needle 14. Consequently, the needle case 37 (protective cover) is easy to grab with the fingers 48 and can be easily turned for the purpose of mounting or removal, so the job of mounting or removing the needle case 37 or the needle unit 35 including the injection needle 14 can be accomplished with the greatest of ease.

Embodiment 2

The pharmaceutical injection device in Embodiment 2 pertaining to the present invention will now be described.

The pharmaceutical injection device in Embodiment 2 has the same basic configuration as the pharmaceutical injection device in Embodiment 1, but the configuration of the restrictor is different. Therefore, the description of Embodiment 2 below will focus on the differences from Embodiment 1. Those components that are the same as in Embodiment 1 will be numbered the same and will not be described again.

Figure 26:
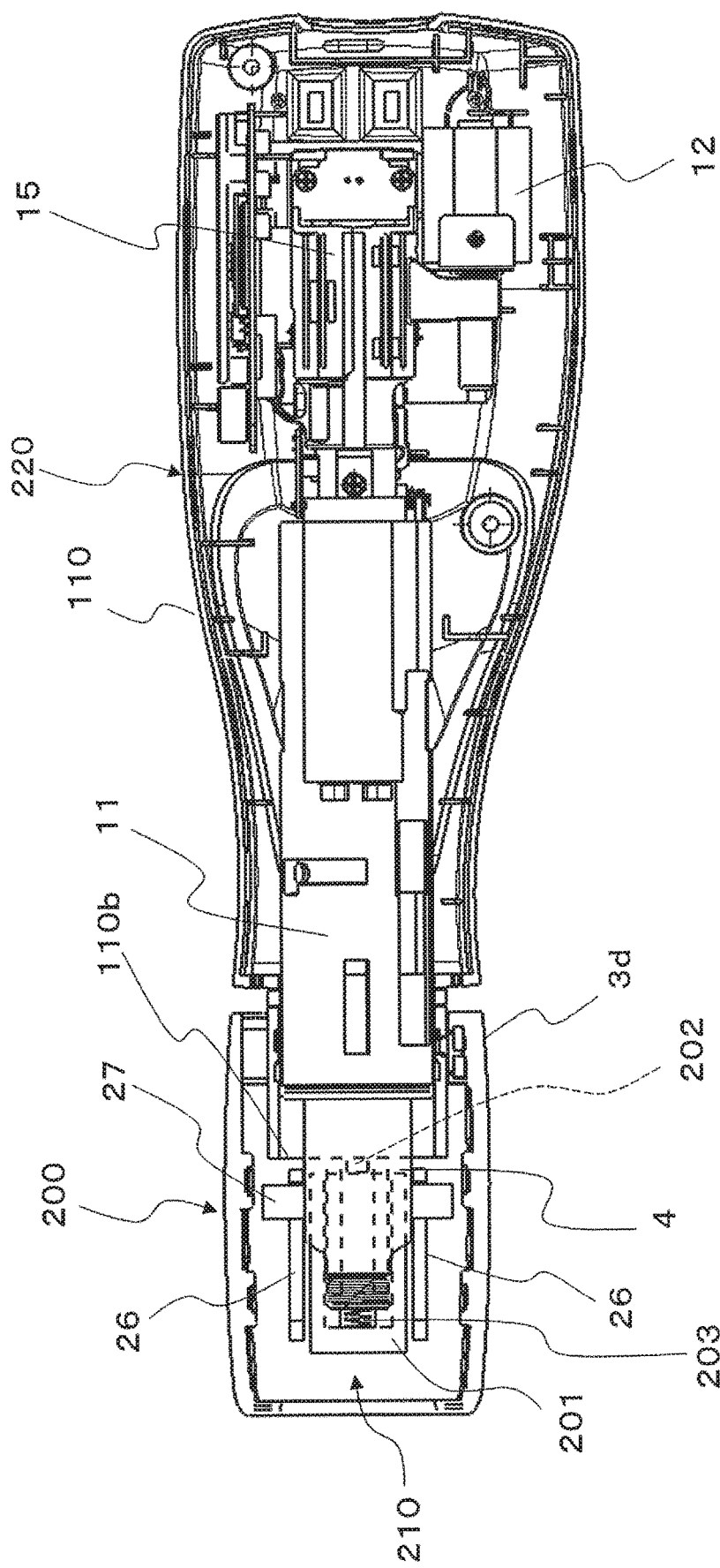
FIG. 26 is a cross section of the internal configuration of the pharmaceutical injection device in Embodiment 2 pertaining to the present invention.

FIG. 26 is a diagram of the internal configuration of the pharmaceutical injection device in this embodiment. As shown in FIG. 26, the pharmaceutical injection device in this embodiment has a pharmaceutical injection device main body 220 and a pharmaceutical syringe unit 200. The pharmaceutical injection device main body 220 has a main body case 110. The pharmaceutical syringe unit 200 in this embodiment differs from the pharmaceutical syringe unit 2 in Embodiment 1 in that it does not have the restrictor 29 described in Embodiment 1, and has a restrictor 210 instead. Also, the main body case 110 in Embodiment 2 differs from the main body case 1 Embodiment 1 in that it does not have the protrusion 40 that engages with the restrictor 29 described in Embodiment 1, and instead has a protrusion 110b (discussed below).

1. Pharmaceutical Syringe Unit in Unmounted State

First, we will describe the pharmaceutical syringe unit 200 in a state of having been removed from the main body case 110 of the pharmaceutical injection device main body 220.

Figure 27:
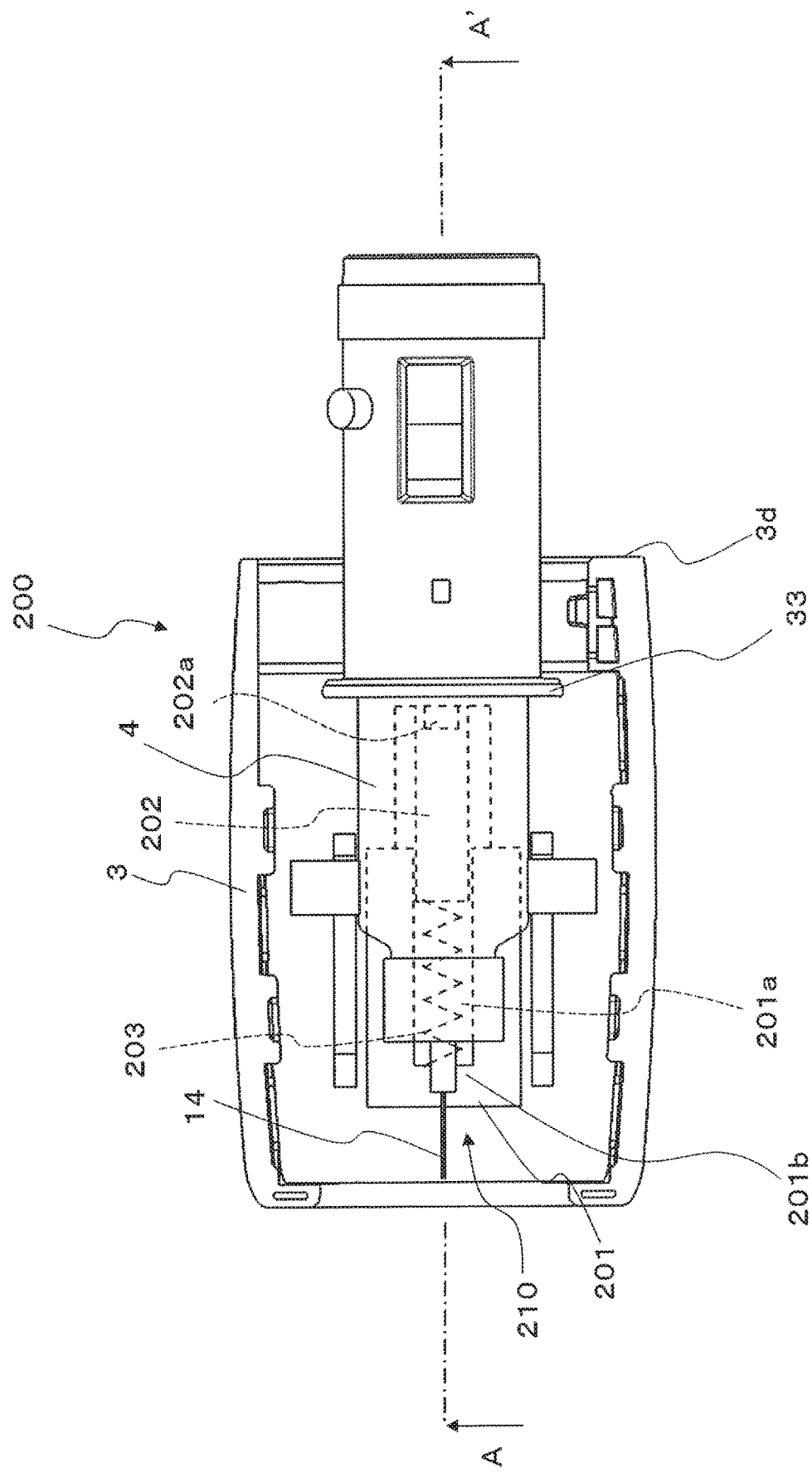
FIG. 27 is a diagram of the internal configuration of the pharmaceutical syringe unit in a state of having been removed from the main body case in the pharmaceutical injection device in FIG. 26.
Figure 28:
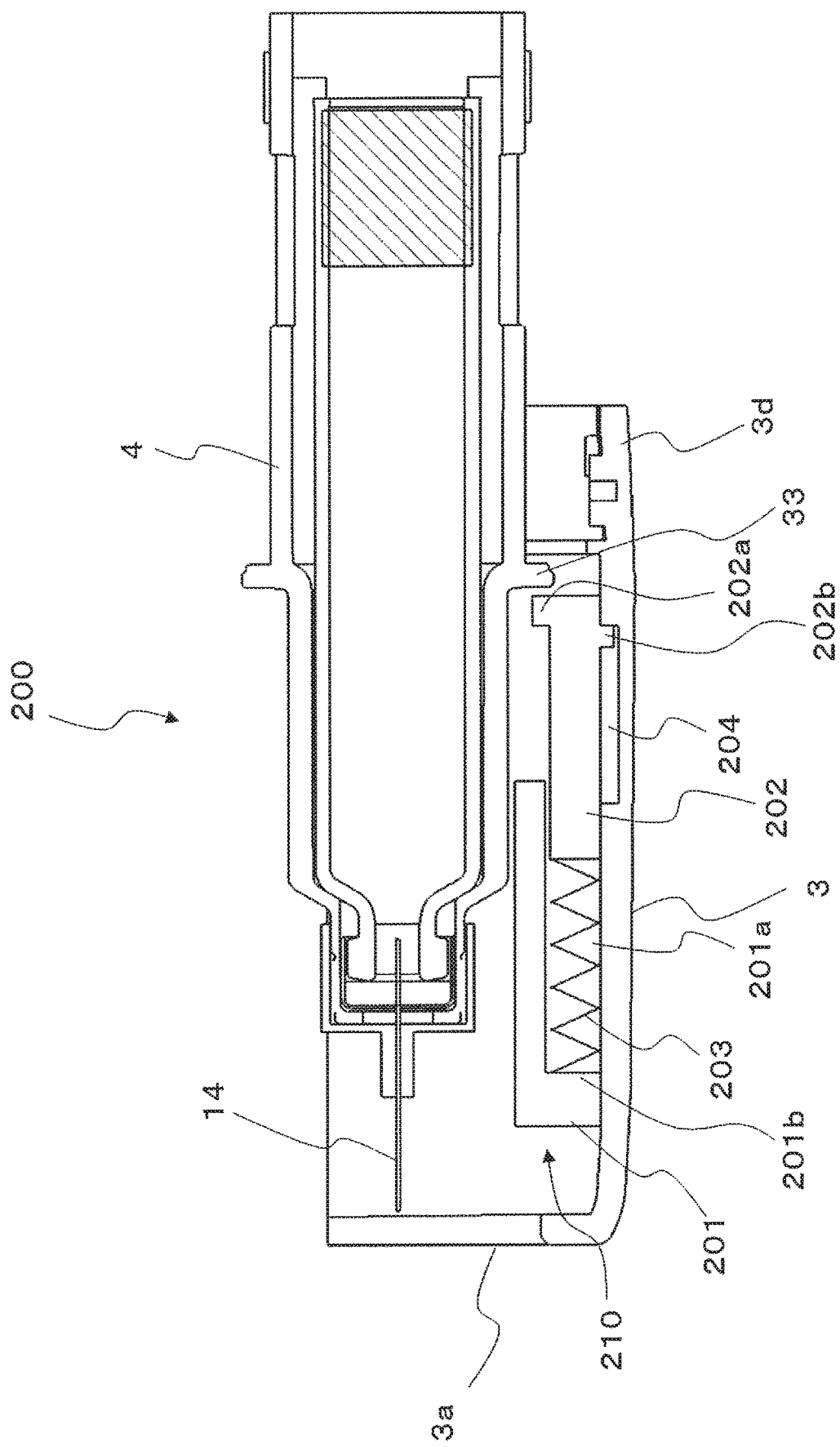
FIG. 28 is a cross section along the A-A' line in FIG. 27.

FIG. 27 is a diagram of the internal configuration of the pharmaceutical syringe unit 200 in a state of having been removed from the main body case 110 of the pharmaceutical injection device main body 220. In FIG. 27, the upper member 3g (see FIG. 10B) constituting the distal end cap 3 has been removed (the same applies to FIG. 28). FIG. 28 is a cross section along the A-A' line in FIG. 27.

As shown in FIGS. 27 and 28, the pharmaceutical syringe unit 200 in Embodiment 2 has the restrictor 210. The restrictor 210 has a stopper guide 201, a stopper 202, and a stopper spring 203.

The stopper guide 201 has a guide groove 201a formed from the rear toward the front. The rear end side of the guide groove 201a is open, and the front end side of the guide groove 201a is blocked off.

The stopper 202 is inserted into the guide groove 201a from the rear end thereof. The stopper 202 has at its rear end a protrusion 202a that protrudes upward. Also, the stopper 202 has on its lower face a protrusion 202b that protrudes downward. This protrusion 202b is inserted into a groove 204 formed in the forward and backward direction in the inner peripheral face of the lower member 3d constituting the distal end cap 3. The movable range over which the stopper 202 slides in the forward and backward direction is restricted by this groove 204.

The stopper spring 203 is provided inside the guide groove 201a. The front end of the stopper spring 203 is latched to the front part 201b of the stopper guide 201, and the rear end is latched to the front end of the stopper 202.

Thus, the stopper 202 and the stopper spring 203 are configured so that in a state in which the pharmaceutical syringe unit 200 has been removed from the main body case 110 of the pharmaceutical injection device main body 220, the protrusion 202a of the stopper 202 is located a short distance (about 0.5 mm) away from the flange 33 provided around the outside of the syringe cover 4.

As shown in FIG. 28, the protrusion 202a is provided at a location overlapping the flange 33, as seen from the front side (seen from the left in FIG. 28). Therefore, in a state in which the pharmaceutical syringe unit 200 has been removed from the main body case 110 of the pharmaceutical injection device main body 220, even if the syringe cover 4 tries to move to the front end side, the flange 33 will interfere with the protrusion 202a, and since the protrusion 202a is biased to the rear by the stopper spring 203, the syringe cover 4 will be prevented from moving forward.

The sliding of the syringe cover 4 is thus such that movement in the distal end direction is restricted by the load (biasing force) of the stopper spring 203. Specifically, with the pharmaceutical syringe unit 200 in a state of not having been mounted to the pharmaceutical injection device, even when the injection needle 14 has been mounted on the distal end side of the syringe cover 4, the injection needle 14 will not be exposed from the distal end face 3a of the distal end cap 3 because of the restrictor 210 (consisting of the stopper spring 203, etc.), so safe operation is ensured.

The stopper spring 203 is set to a light load (about several dozen grams, or about 0.2 to 0.5 N), one which allows the sliding operation of the syringe cover 4 to be restricted.

2. Unmounted Pharmaceutical Syringe Unit

Next, the pharmaceutical syringe unit 200 in a state of having been attached to the main body case 110 of the pharmaceutical injection device main body 220 will be described.

2-1. Needle Withdrawal Position

Figure 29:
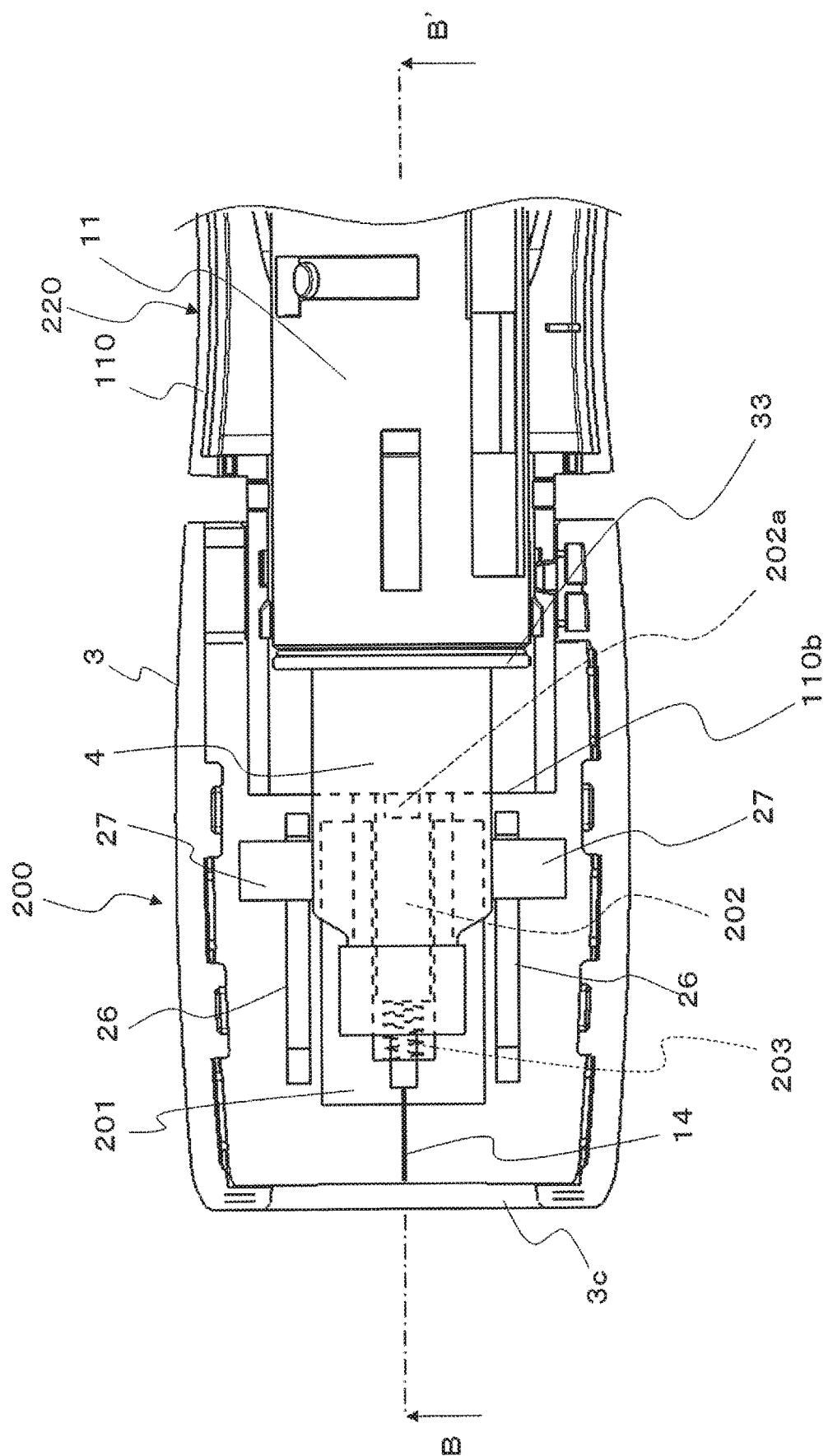
FIG. 29 shows the state of the pharmaceutical syringe unit in the needle withdrawal position of the pharmaceutical injection device in FIG. 26.
Figure 30:
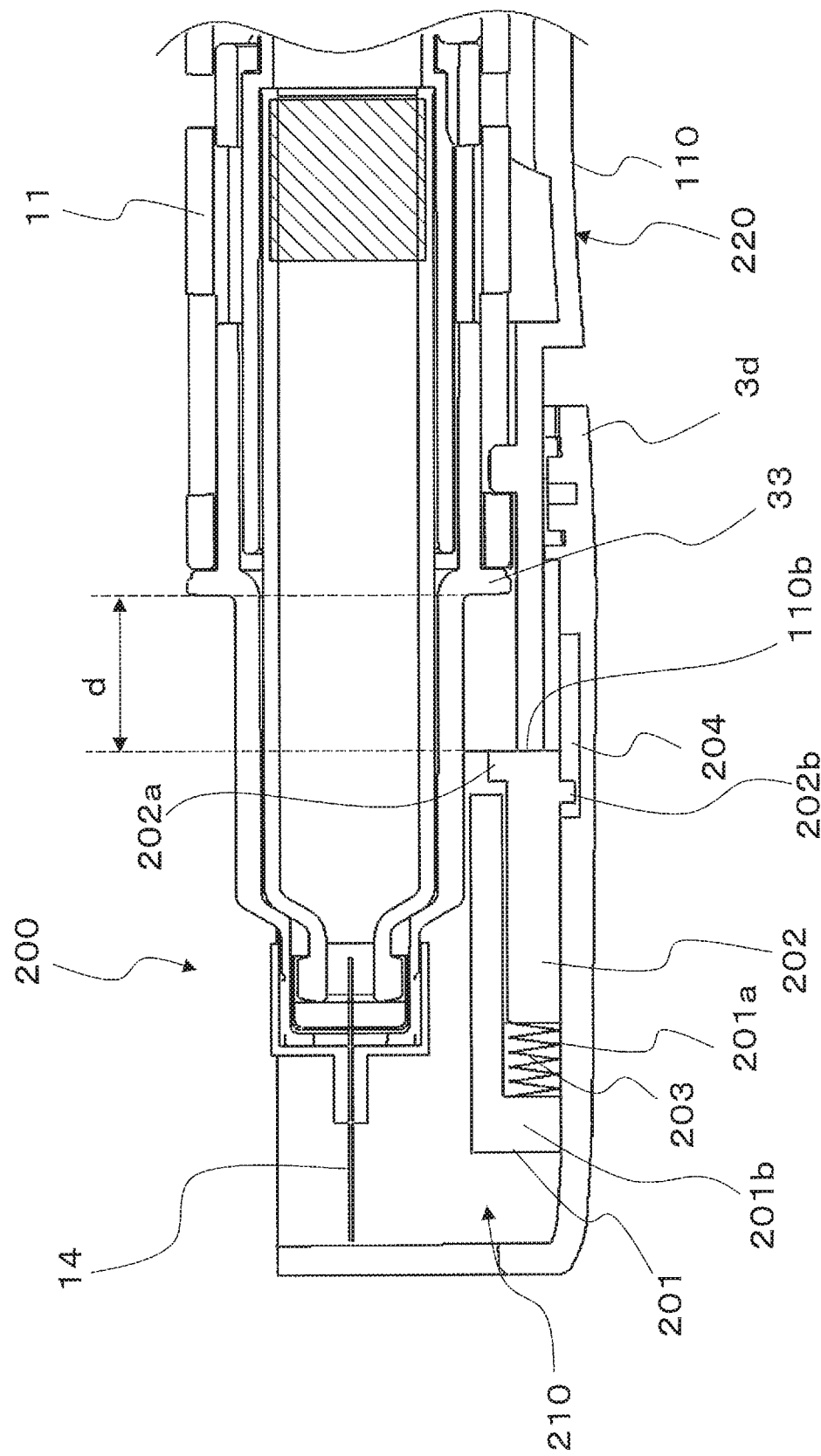
FIG. 30 is a cross section along the B-B' line in FIG. 29.
Figure 31:
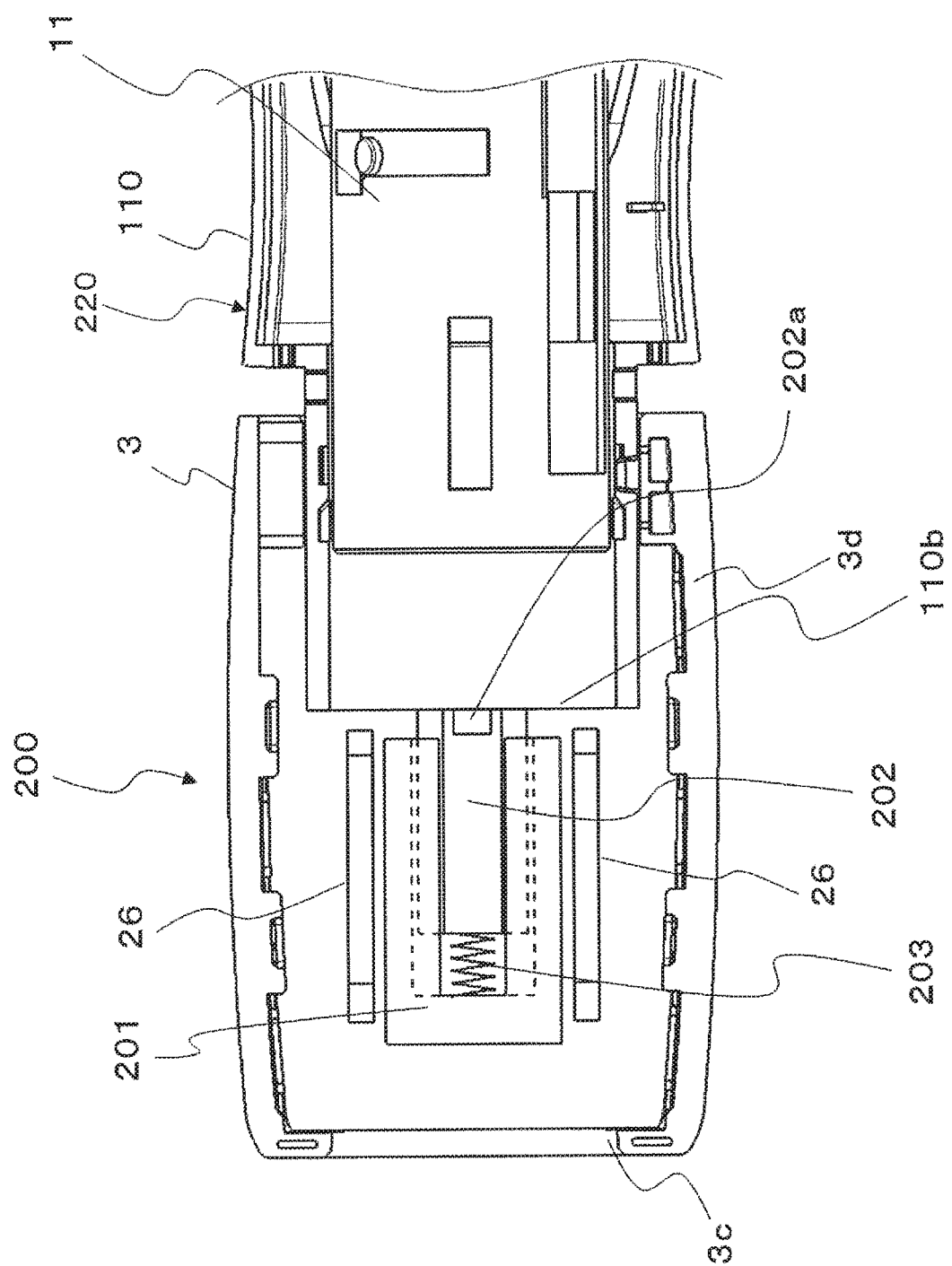
FIG. 31 shows the state when a syringe cover 4 has been removed from the state shown in FIG. 29.

First, the pharmaceutical syringe unit 200 in the needle withdrawal position will be described. FIG. 29 shows the internal configuration of the pharmaceutical syringe unit 200 in a state of having been attached to the main body case 110 of the pharmaceutical injection device main body 220. FIG. 30 is a cross section along the B-B' line in FIG. 29. FIG. 31 shows the state when the syringe cover 4 has been removed from FIG. 29 for the purpose of illustration. FIGS. 29 and 30 show a state in which the injection needle 14 is disposed in the needle withdrawal position.

As shown in FIGS. 29 and 30, when the pharmaceutical syringe unit 200 is mounted to the main body case 110, the main body case 110 pushes the protrusion 202a of the stopper 202 forward. The stopper 202 is biased to the rear by the stopper spring 203, but the stopper 202 is moved forward by the main body case 110 against this biasing force. More precisely, in this embodiment, as shown in FIG. 30, the protrusion 110b that protrudes forward is formed at the distal end on the lower side of the main body case 110 (the lower member 3d side of the distal end cap 3), and this protrusion 110b pushes the stopper 202 forward.

Even in a state in which the stopper 202 is pushed forward by this protrusion 110b, the syringe cover 4 having the injection needle 14 mounted on the distal end side (having the pharmaceutical syringe 5 contained in the interior) is mounted to the main body case 110 of the pharmaceutical injection device, and is held to the rear (disposed at the needle withdrawal position) by the slide motor 12 in the main body case 110 (see the above-mentioned FIG. 4), so the injection needle 14 is not exposed from the distal end face 3a of the distal end cap 3.

That is, when the pharmaceutical syringe unit 200 has been mounted to the pharmaceutical injection device main body 220 as above, even in a state in which the stopper 202 is pushed forward by the protrusion 110b, a gap d (see FIG. 30) that is greater than the stroke of the slide motor 12 is formed between the flange 33 of the syringe cover 4 and the rear end (protrusion 202a) of the stopper 202 of the restrictor 210 provided inside the distal end cap 3. Consequently, interference between the stopper 202 and the flange 33 is eliminated.

2-2. Needle Insertion Position

Next, the pharmaceutical syringe unit 200 at the needle insertion position will be described.

Figure 32:
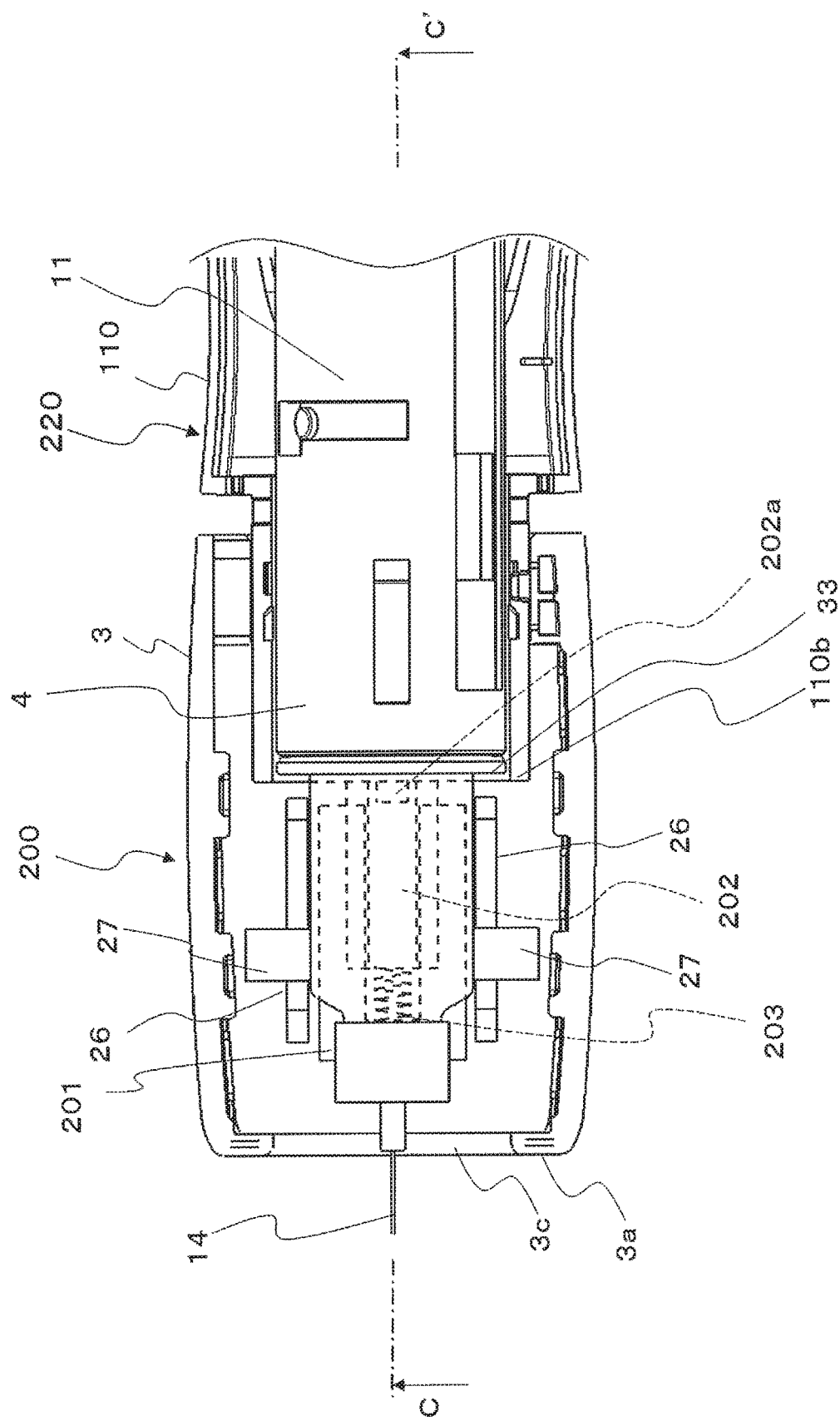
FIG. 32 shows the state of the pharmaceutical syringe unit in the needle insertion position of the pharmaceutical injection device in FIG. 26.
Figure 33:
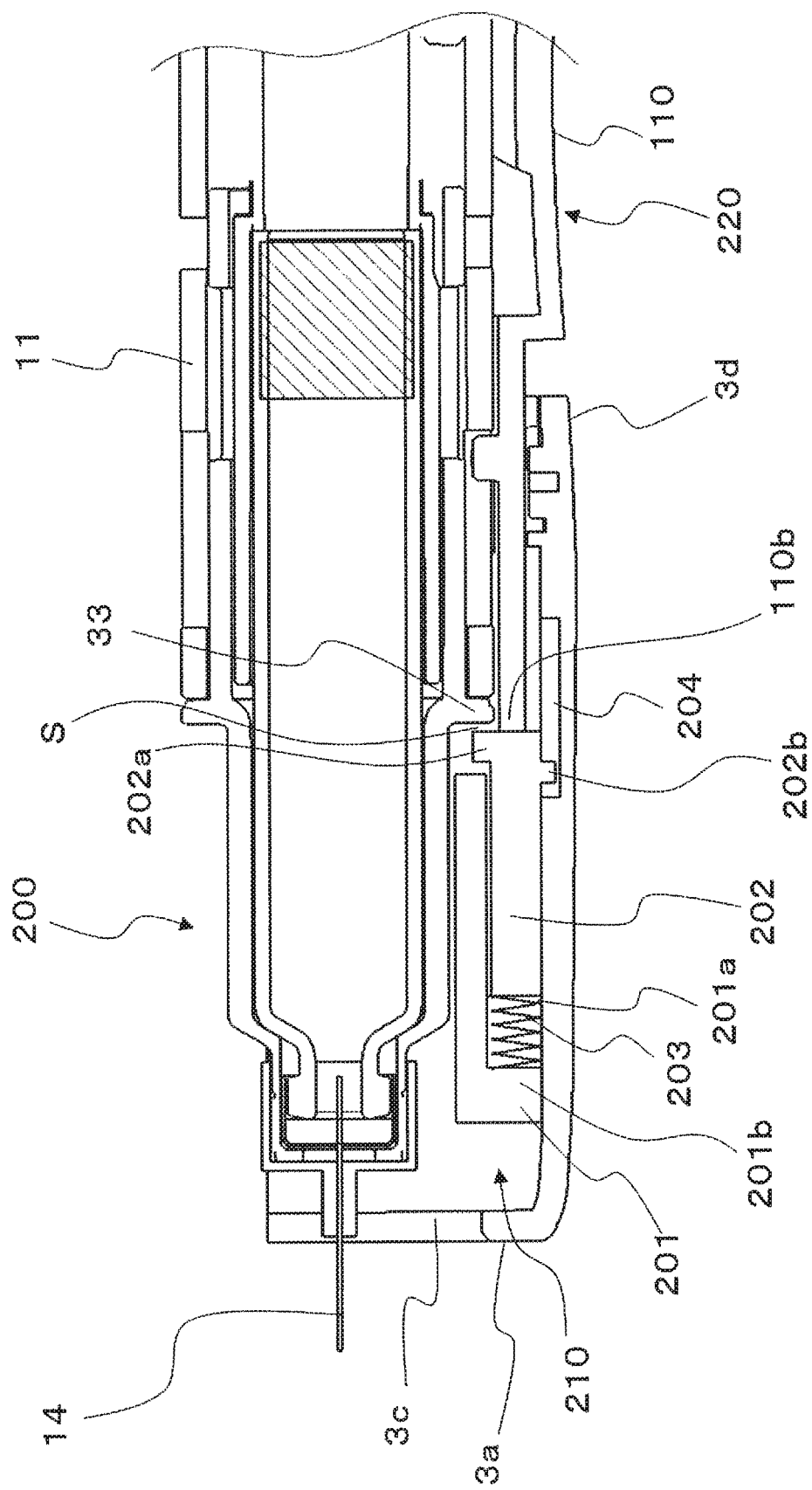
FIG. 33 is a cross section along the C-C' line in FIG. 32.

FIG. 32 shows the internal configuration of the pharmaceutical syringe unit 200 in a state in which the syringe cover 4 has moved to the needle insertion position. FIG. 33 is a cross section along the C-C' line in FIG. 32.

When the inject button 7 (see FIGS. 1, 4, etc.) is pressed, the slide motor 12 (see FIG. 4) is driven, and the inner case 11 moves (slides) from the needle withdrawal position toward the needle insertion position to the distal end side. The syringe cover 4 moves along with the inner case 11. The movement of the syringe cover 4 to the distal end side causes the injection needle 14 mounted to the distal end of the syringe cover 4 to protrude from the distal end face 3a via the distal end opening 3c in the distal end cap 3 (see FIGS. 32 and 33).

As shown in FIGS. 32 and 33, the flange 33 of the syringe cover 4 is not touching the protrusion 202a at the needle insertion position (see the gap S in FIG. 33).

Specifically, even though the syringe cover 4 moves forward from the needle withdrawal position toward the needle insertion position, the protrusion 202a of the stopper 202 does not interfere with the flange 33. Thus, since the stopper 202 is moved forward by the protrusion 110b of the main body case 110, the sliding operation of the syringe cover 4 accompanying needle insertion and withdrawal is not hindered by the stopper 202.

That is, this is because the distance between the flange 33 and the protrusion 202a of the stopper 202 (the gap d (see FIG. 30)) is set to be greater than the distance between the needle insertion position and the needle withdrawal position (which is the stroke of the slide motor 12).

3. Operation of Pharmaceutical Syringe Unit

When the pharmaceutical syringe unit 200 is removed from the main body case 110, since the protrusion 110b of the main body case 110 does not push the protrusion 202a, the stopper 202 moves to the rear under the biasing force of the stopper spring 203.

Consequently, as shown in FIG. 28, the protrusion 202a of the stopper 202 hinders movement of the flange 33 of the syringe cover 4, and in normal operation the injection needle 14 does not protrude from the distal end face 3a of the distal end cap 3. The term "normal operation" here means operation that does not exceed the load (biasing force) of the stopper spring 203.

Specifically, with the pharmaceutical syringe unit 200 in this embodiment, since movement of the syringe cover 4 is only restricted by the load of the stopper spring 203, if a force greater than the load of the stopper spring 203 is exerted, such as when the pharmaceutical syringe unit 200 is mounted to the main body case 110, the syringe cover 4 can be moved in the distal end direction.

This is the same when the pharmaceutical syringe unit 200 is disposed in the above-mentioned storage case 43. This will be discussed in further detail below, but when the pharmaceutical syringe unit 200 in a state of having been removed from the main body case 110 of the pharmaceutical injection device main body 220 is disposed on the stationary part 39 of the injection needle mounting and removal tool 80 provided to the base component 44 of the storage case 43 (see FIG. 23), the syringe cover 4 is pushed out in the distal end direction by the slide component 391, the stopper spring 203 is compressed, and the needle mounting component 28 moves to the distal end side (see FIG. 23). Accordingly, the mounting of the injection needle 14 to the needle mounting component 28 and the removal of the injection needle 14 from the needle mounting component 28 (the series of jobs including the mounting of the injection needle 14 to the needle case 37, the subsequent removal of the needle unit 35, etc.) can be carried out easily.

As discussed above, the pharmaceutical syringe unit 200 in Embodiment 2 is such that in a state of having been removed from the main body case 110, the sliding of the syringe cover 4 can be easily restricted by the restrictor 210, and in normal operation the injection needle 14 is not exposed from the distal end face 3a of the distal end cap 3, which affords better safety, and the syringe cover 4 can be moved to the distal end side merely by pushing the pharmaceutical syringe unit 200 into the stationary part 39, which makes the job of replacing the injection needle easier.

4. Mounting and Removal of Injection Needle

The method for mounting the needle unit 35 to the needle mounting component 28 of the pharmaceutical syringe unit 200, and the method for removing the injection needle 14 from the needle mounting component 28 will now be described through reference to FIGS. 34 to 37.

As explained in Embodiment 1, the mounting of the needle unit 35 including the injection needle 14, or the removal of the needle case 37 including the injection needle 14 is generally performed in a state in which the pharmaceutical syringe unit 200 has been mounted to the main body case 110. However, when mounting or removing the injection needle 14, the syringe cover 4 is disposed at the needle withdrawal position, so although mounting and removal are possible, they can hardly be considered easy.

Figure 34:
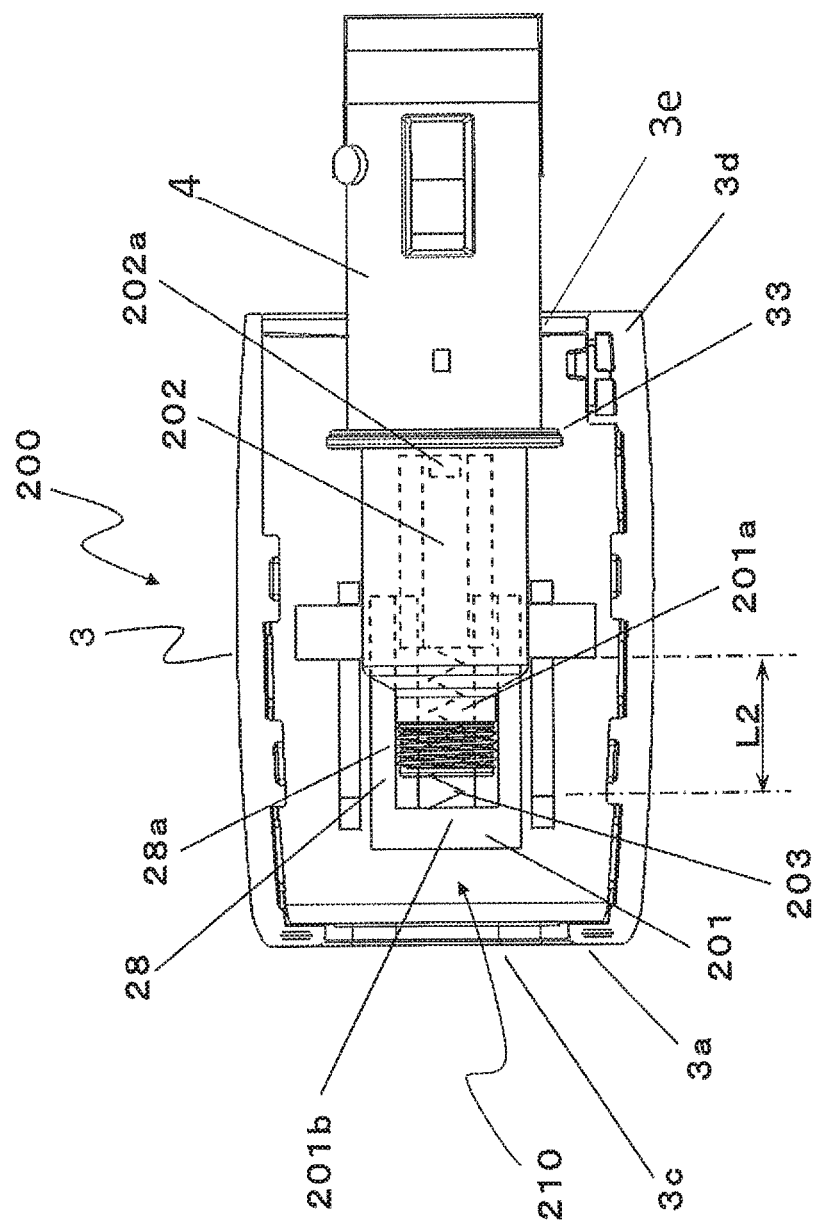
FIG. 34 shows the state when the injection needle has been removed from the pharmaceutical syringe unit in FIG. 27.

Also, as shown in FIG. 34, in a state in which the pharmaceutical syringe unit 200 is removed from the main body case 1 of the pharmaceutical injection device, the flange 33 is pushed to the rear end opening 3e side by the biasing force of the stopper spring 203, so the needle mounting component 28 is located at the back of the distal end cap 3. Accordingly, here again, although mounting and removal are possible, they can hardly be considered easy.

Figure 35:
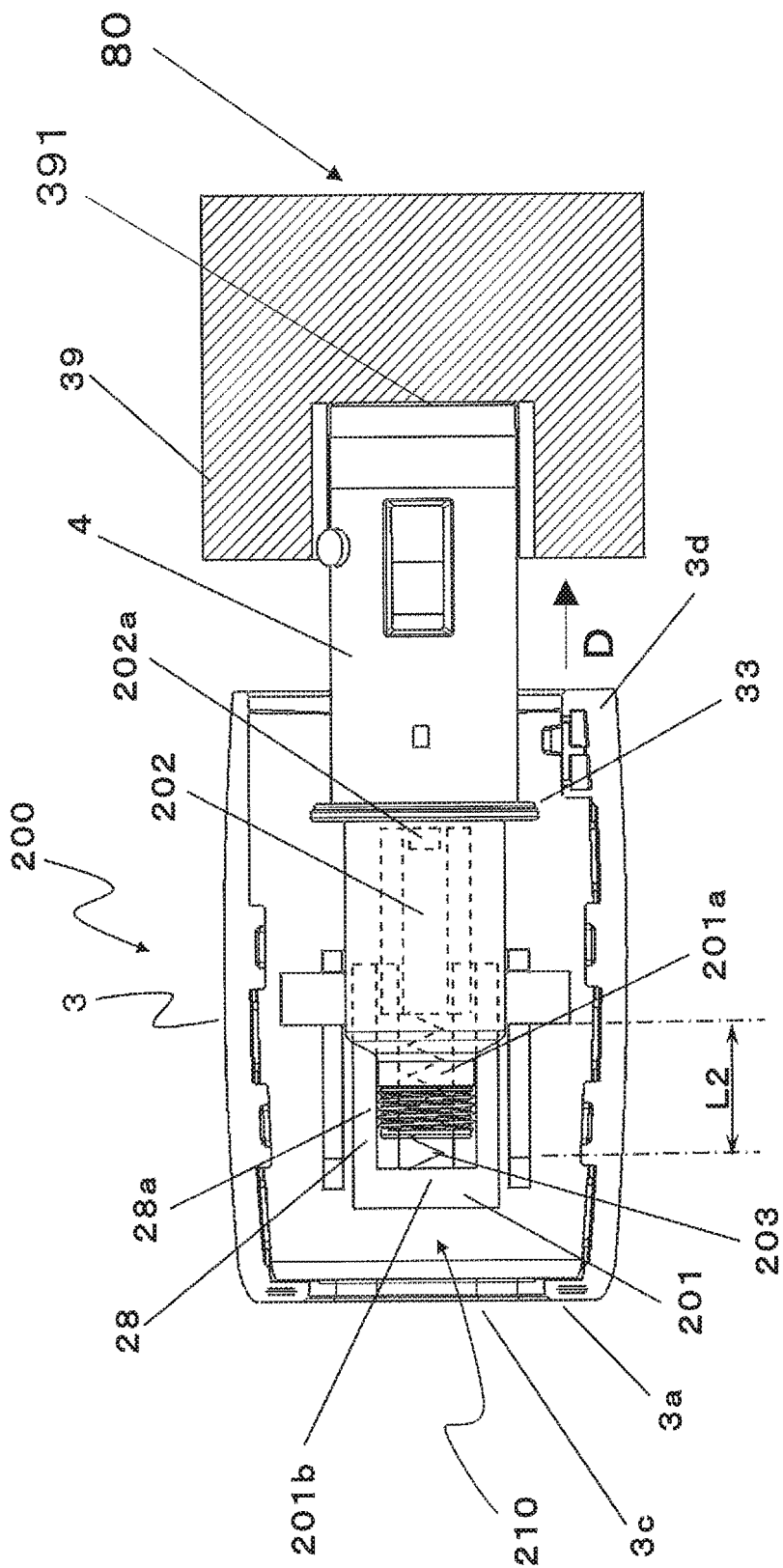
FIG. 35 is a cross section of the method for attaching and removing the injection needle to and from the pharmaceutical syringe unit in FIG. 34.
Figure 36:
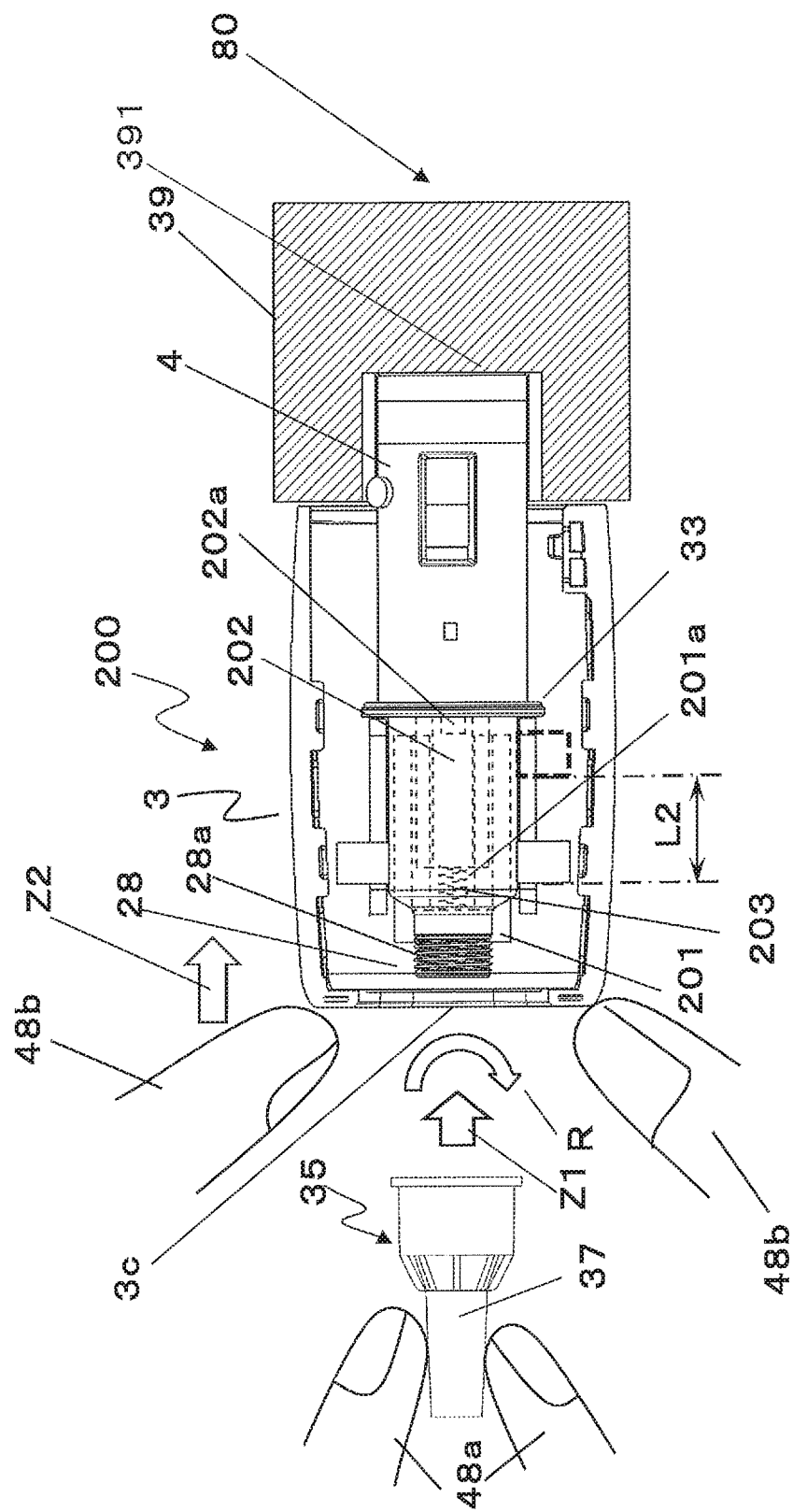
FIG. 36 is a cross section of the method for attaching and removing the injection needle to and from the pharmaceutical syringe unit in FIG. 34.
Figure 37:
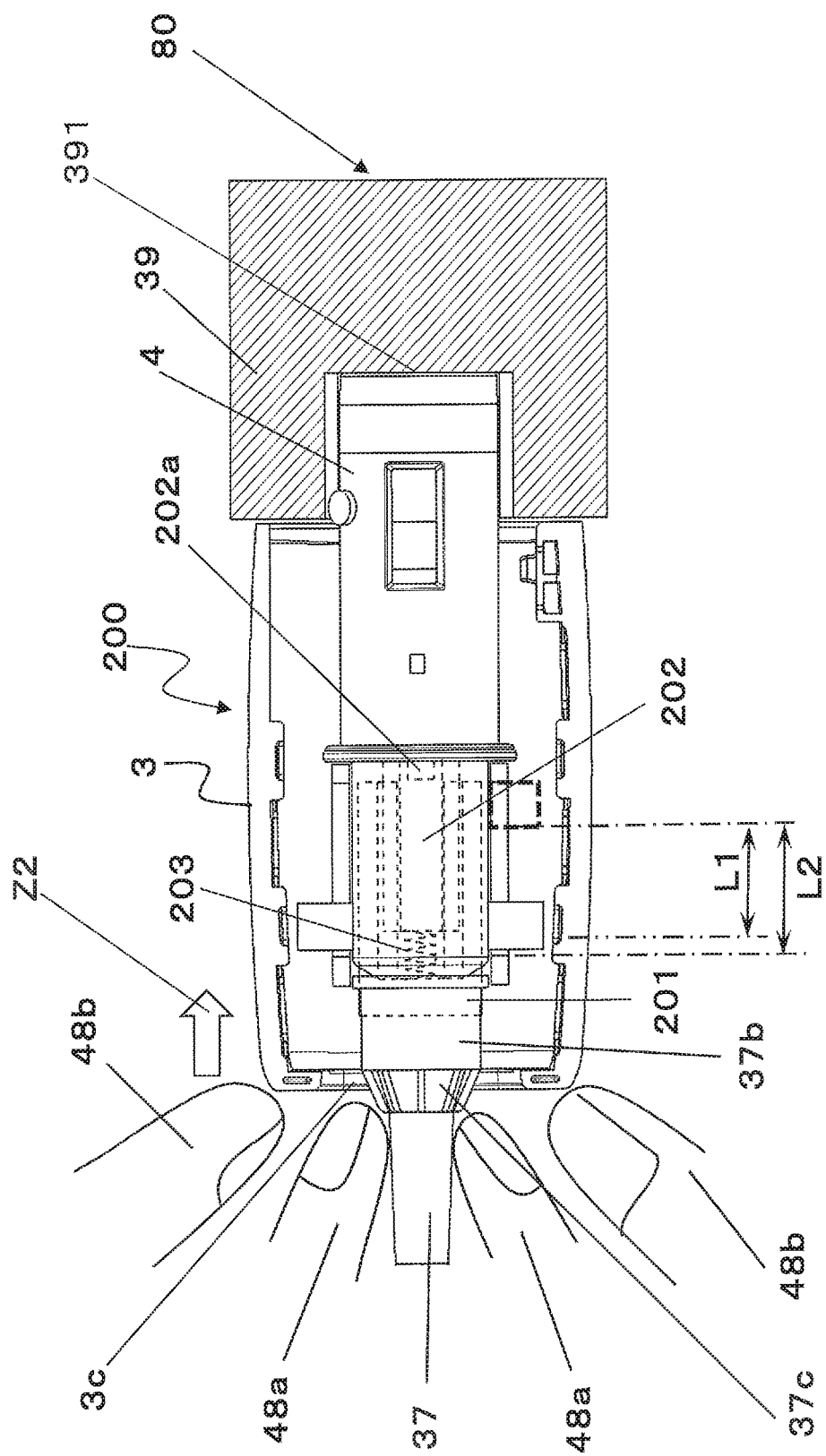
FIG. 37 is a cross section of the method for attaching and removing the injection needle to and from the pharmaceutical syringe unit in FIG. 34.

In view of this, in this embodiment the mounting and removal of the injection needle 14 can be easily performed by using the injection needle mounting and removal tool 80 shown in FIG. 35. FIG. 35 shows the state when the pharmaceutical syringe unit 200 removed from the pharmaceutical injection device main body 220 is put in the injection needle mounting and removal tool 80 described in Embodiment 1. FIG. 36 shows the state when the distal end cap 3 has been pushed to the injection needle mounting and removal tool 80 side from the state in FIG. 35. FIG. 37 shows the state when the needle case 37 is mounted in the state in FIG. 36.

As discussed above, in a state of having been removed from the pharmaceutical injection device main body 220, the pharmaceutical syringe unit 200 is such that the flange 33 is pushed to the rear end opening 3e side by the biasing force of the stopper spring 203, and the syringe cover 4 slides in the rear end direction (to the right in FIG. 34) with respect to the distal end cap 3. In other words, the distal end cap 3 can be said to slide in the distal end direction (to the left in FIG. 34) with respect to the syringe cover 4 under the biasing force of the stopper spring 203.

As shown in FIG. 35, in the mounting and removal of the injection needle 14, the pharmaceutical syringe unit 200 is disposed in the injection needle mounting and removal tool 80. More specifically, the pharmaceutical syringe unit 200 is disposed in the injection needle mounting and removal tool 80 so that the rear end of the syringe cover 4 is inserted into the concave shape of the slide component 391 formed on the stationary part 39 of the injection needle mounting and removal tool 80.

In a state in which the rear end of the syringe cover 4 is disposed in the concave shape of the slide component 391, the distal end cap 3 is biased in the distal end direction (the opposite side from the injection needle mounting and removal tool 80) by the stopper spring 203. Accordingly, the distal end cap 3 is not touching the stationary part 39.

Then, as shown in FIG. 36, when the distal end face 3a of the distal end cap 3 is pushed with the fingers 48b to the injection needle mounting and removal tool 80 side (see the arrow Z2), the stopper spring 203 built into the distal end cap is compressed, and the needle mounting component 28 of the syringe cover 4 moves closer to the distal end opening 3c.

Once this state is reached, it is easy to mount the needle unit 35 to the male threads 28a of the needle mounting component 28 through the distal end opening 3c, or to remove the injection needle 14 from the male threads 28a.

More specifically, when the injection needle 14 is mounted to the needle mounting component 28 of the syringe cover 4, the needle unit 35 including the injection needle 14 is inserted from the arrow Z1 direction and turned to the right (clockwise) in the arrow R direction, which causes the female threads 38b of the needle base 38 of the injection needle 14 housed in the interior of the needle unit 35 to mesh with the male threads 28a of the needle mounting component 28, and the injection needle 14 to be mounted to the needle mounting component 28. At this point, as shown in FIG. 37, since the needle case 37 is located in the distal end opening 3c up to the portion of the knurled part 37c, it is easy to grab and turn with the fingers 48a.

Meanwhile, when the injection needle 14 is removed from the needle mounting component 28, in a state in which the injection needle 14 mounted to the needle mounting component 28 is covered by the needle case 37, rotation in the opposite direction from the arrow R (counter-clockwise) unscrews the male threads 28a of the needle mounting component 28 from the female threads 38b of the injection needle 14, and the injection needle 14 goes into the needle case 37. The injection needle 14 can then be simply removed by pulling out the needle case 37 in the opposite direction from the arrow Z1 (see FIG. 36). At this point, as shown in FIG. 37, since the knurled part 37c is located in the distal end opening 3c, it can be grabbed by the fingers 48a, and the male threads 28a can be easily unscrewed from the female threads 38b.

Just as in Embodiment 1, L1 shown in FIG. 37 is the stroke of the slide motor 12 of the syringe cover 4 in the mounting of the pharmaceutical syringe unit 200 to the pharmaceutical injection device main body 220. L2 is the slide stroke of the guide components 26. L2 is formed longer than L1, and in drive by the slide motor 12, the syringe cover 4 mounted to the inner case 11 does not hit the risers 26a (the stopper 60a) on the distal end side of the guide components 26 (see FIG. 17, etc.).

Because L2 is greater than L1, the syringe cover 4 can protrude more to the distal end side when mounted to the stationary part 39 than when mounted to the pharmaceutical injection device main body 220 (in this example, L2 is about 2 mm longer, but anywhere between 1 and 10 mm is effective).

Specifically, the needle unit 35 and so forth will be more exposed from the distal end opening 3c to the outside, when the pharmaceutical syringe unit 2 is mounted to the stationary part 39 than when it is mounted to the pharmaceutical injection device.

Therefore, as discussed above, the knurled part 37c can be located in the distal end opening 3c, and the injection needle 14 will be easier to mount and remove.

5. Storage Case

An example of when the injection needle mounting and removal tool of this embodiment is applied to the storage case 43 will now be described through reference to FIGS. 38 to 40. The storage case 43 in Embodiment 2 has the same basic configuration as in Embodiment 1, and its description will be omitted as appropriate.

Figure 38:
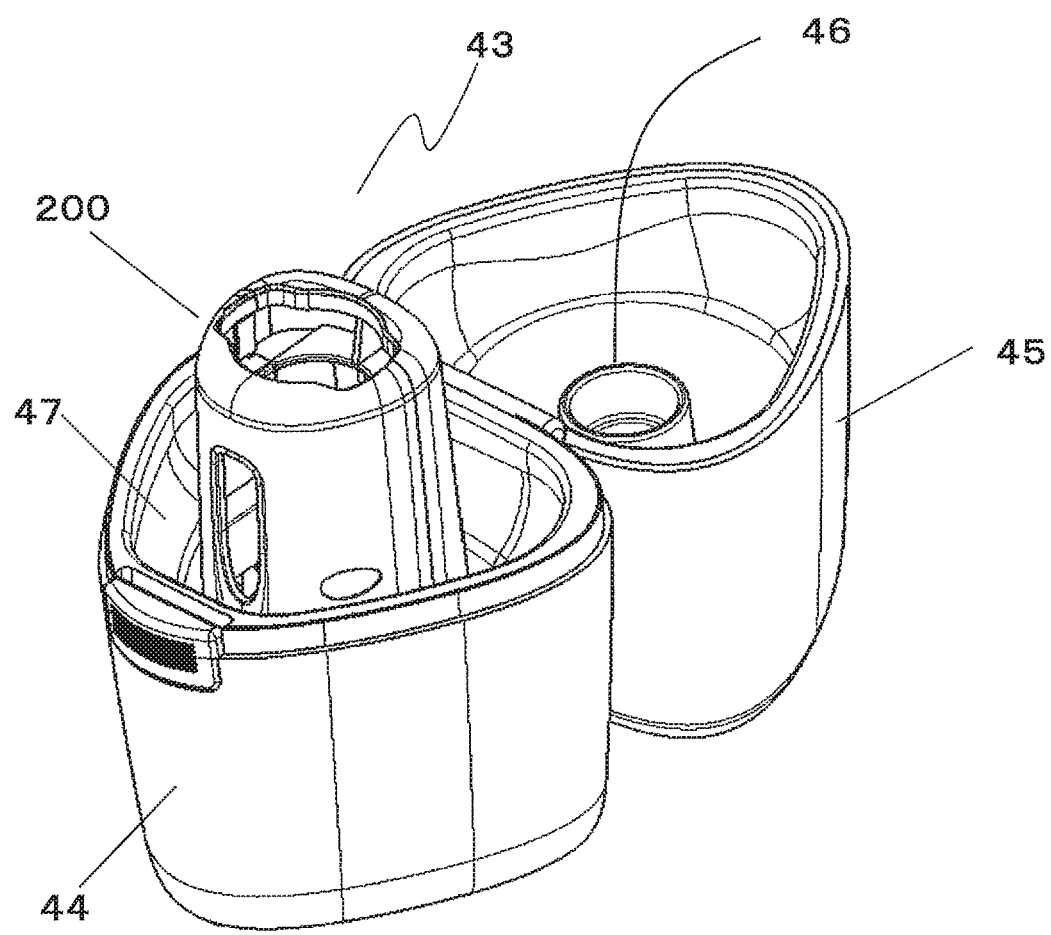
FIG. 38 is an oblique view of the method for attaching and removing an injection needle using the storage case for the pharmaceutical syringe unit in FIG. 34.

FIG. 38 shows the state when the lid 45 of the storage case 43 is open upwards. The pharmaceutical syringe unit housing 47 is provided in the interior of the base component 44 of the storage case 43. Also, the pharmaceutical syringe unit housing 47 has the injection needle mounting and removal tool 80 shown in FIGS. 35 to 37.

Next, the operation for mounting the injection needle 14 to the pharmaceutical syringe unit 200 disposed in the storage case 43 will be described.

As shown in FIG. 38, when the lid 45 is opened, the pharmaceutical syringe unit 200 is disposed on the base component 44 of the storage case 43. At this point the pharmaceutical syringe unit 200 is in the state shown in FIG. 35, and the right direction in FIG. 35 corresponds to downward in FIG. 38.

Figure 39A:
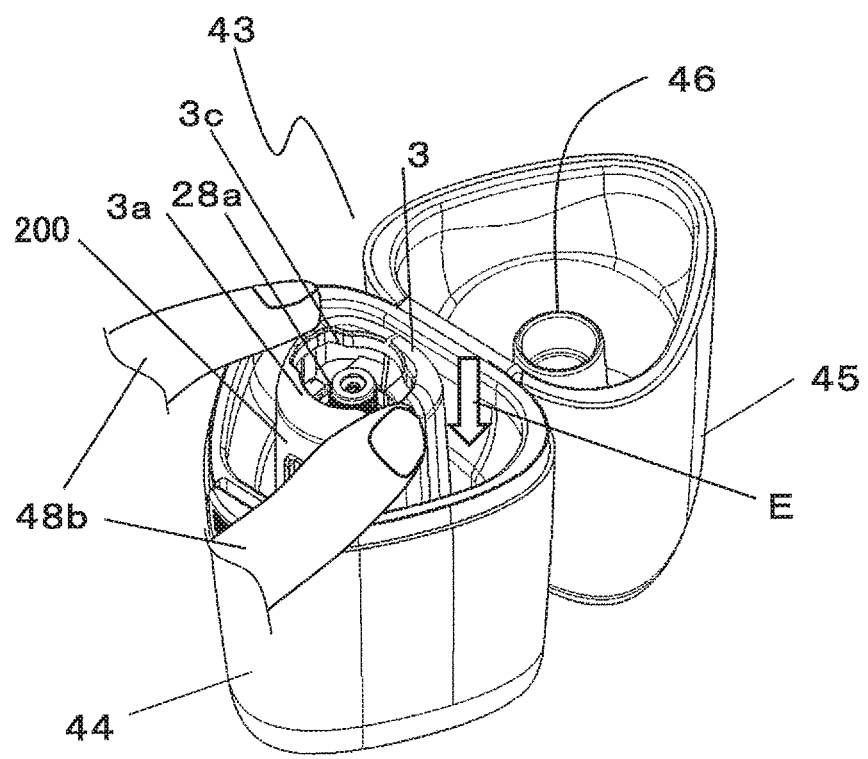
FIG. 39A is an oblique view of the method for attaching and removing an injection needle using the storage case for the pharmaceutical syringe unit in FIG. 34.
Figure 39B:
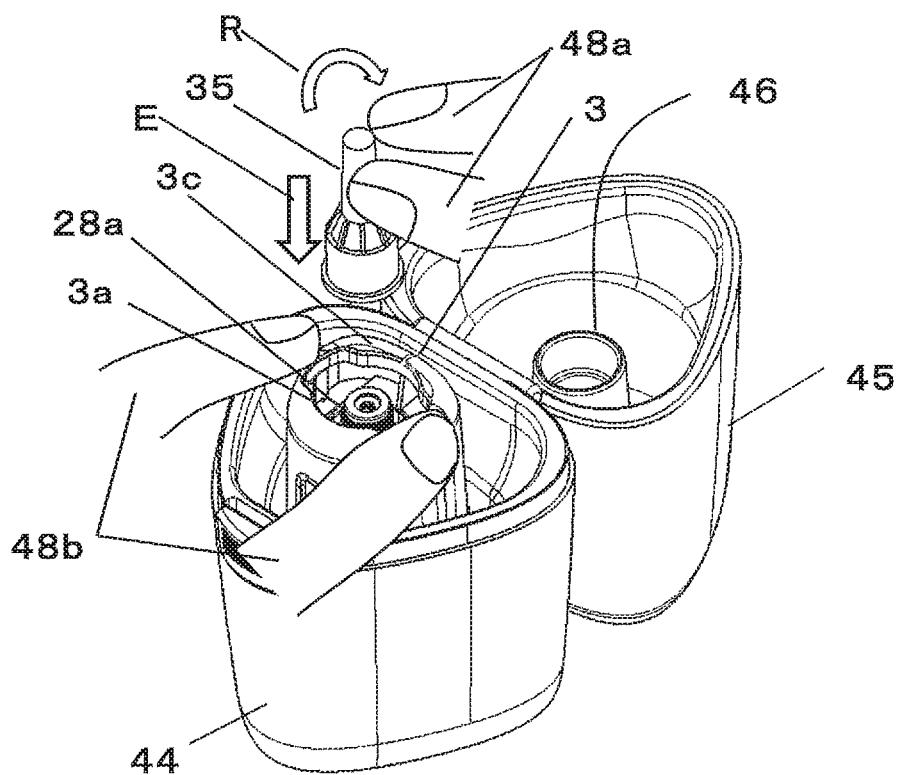
FIG. 39B is an oblique view of the method for attaching and removing an injection needle using the storage case for the pharmaceutical syringe unit in FIG. 34.
Figure 40:
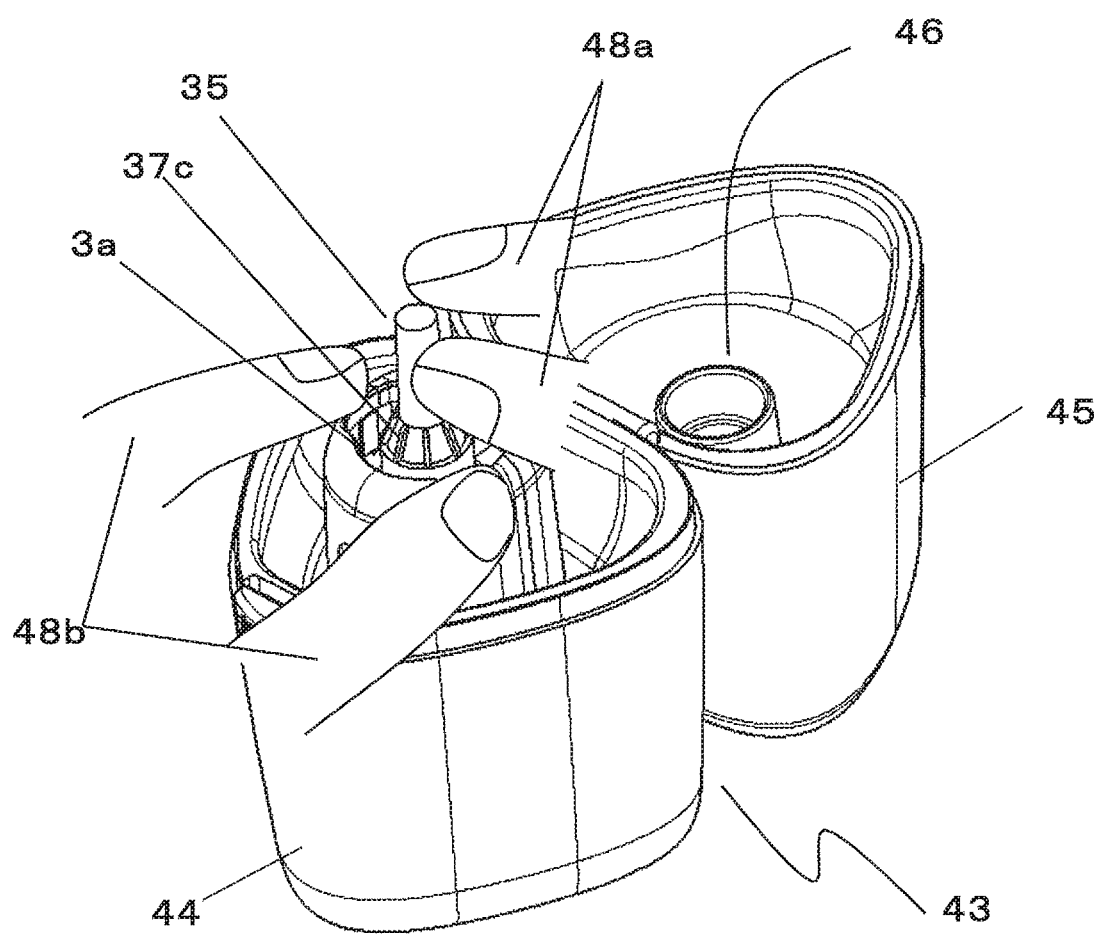
FIG. 40 is an oblique view of the method for attaching and removing an injection needle using the storage case for the pharmaceutical syringe unit in FIG. 34.

In this state, as shown in FIG. 39A, the area near the distal end face 3a of the distal end cap 3 is pushed downward with the fingers 48b to move the male threads 28a of the needle mounting component 28 closer to the distal end opening 3c (see FIG. 36). Next, as shown in FIG. 39B, the needle unit 35 is threaded onto the male threads 28a of the needle mounting component 28 provided on the distal end side of the syringe cover 4, to mount the needle unit 35 to the pharmaceutical syringe unit 200 as shown in FIG. 40. The state shown in FIG. 40 corresponds to the state shown in FIG. 37.

More specifically, the needle unit 35 is moved downward as shown in FIG. 39B and inserted into the needle mounting component 28 through the distal end opening 3c of the distal end cap 3 (see the arrow E). After this, the needle unit 35 is mounted to the male threads 28a while being turned to the right (clockwise; see the arrow R). At this point the knurled part 37c of the needle case 37 is located in the distal end opening 3c, so the knurled part 37c can be grabbed by the fingers 48a, and the needle case 37 can be easily turned.

Next, the operation for removing the injection needle 14 from the pharmaceutical syringe unit 200 disposed in the storage case 43 will be described. As described in Embodiment 1, when the pharmaceutical injection operation is finished, the needle case 37 is mounted to the pharmaceutical syringe unit 200 so as to cover the injection needle 14. After this, the pharmaceutical syringe unit 200 is removed from the pharmaceutical injection device main body 220 and disposed in the pharmaceutical syringe unit housing 47 with the needle case 37 side facing up.

When the distal end cap 3 is thus pushed downward with the fingers 48b with respect to the pharmaceutical syringe unit 200 disposed in the storage case 43, the stopper spring 203 is compressed, and the needle mounting component 28 is located near the distal end opening 3c. Accordingly, as shown in FIGS. 37 and 40, a portion of the knurled part 37c of the needle case 37 is located in the distal end opening 3c and can be grabbed with the fingers 48a, and the needle case 37 can be easily turned.

The needle case 37 is then turned counter-clockwise, and as a result the injection needle 14 also rotates, and the injection needle 14 is unscrewed from the male threads 28a. After this, the injection needle 14, along with the needle case 37, is moved upward, allowing the injection needle 14 to be removed from the pharmaceutical syringe unit 200.

Also, with the pharmaceutical syringe unit 2 in Embodiment 1, when the syringe cover 4 is moved to the distal end side using the stationary part 41 (see FIG. 22) as a tool, the sliding part 42 must be moved so that the syringe cover 4 is moved to the distal end side after the pharmaceutical syringe unit 2 has been mounted to the stationary part 41. Thus, in Embodiment 1 a two-stage operation is required, entailing mounting to the stationary part 41 and movement of the sliding part 42.

With the pharmaceutical syringe unit 200 in Embodiment 2, however, in mounting to the stationary part 39, the syringe cover 4 can be moved to the distal end side merely by pushing the pharmaceutical syringe unit 200 into the stationary part 39. Specifically, with the pharmaceutical syringe unit 200 in Embodiment 2, the syringe cover 4 can be moved to the distal end side with a single operation, which makes the unit easier to operate.

INDUSTRIAL APPLICABILITY

Certain implementations of the pharmaceutical syringe unit of the present invention may prove to be extremely safe and convenient to use in the replacement of the injection needle, and is expected to find use in injection needle mounting and removal tools, injection needle replacement mechanisms, and so forth provided to a pharmaceutical storage case or a housing case of a pharmaceutical injection device that performs pharmaceutical injection that involves the use of a pharmaceutical syringe and an injection needle and entails mounting and removal at each use.

The invention claimed is:

1. A pharmaceutical syringe unit configured to hold a pharmaceutical-filled pharmaceutical syringe and be mounted to a pharmaceutical injection device main body in order to mount the pharmaceutical syringe to a pharmaceutical injection device, the pharmaceutical syringe unit comprising:
    a distal end cap having a front end side opening and a rear end side opening; and
    a syringe cover that can slide forward and backward with respect to the distal end cap,
    wherein the distal end cap has:
    a guide component configured to guide sliding of the syringe cover forward and backward; and
    a first engagement component that can be engaged with the pharmaceutical injection device main body,
    a front end portion of the syringe cover has a needle mounting component configured to mount an injection needle for injecting the pharmaceutical,
    wherein the syringe cover is configured to slide forward and backward with respect to the distal end cap by operation of the pharmaceutical injection device main body, and is able to move between a needle insertion position at which operation of inserting the injection needle into a target is to be completed, and a needle withdrawal position at which operation of withdrawing the injection needle from the target is to be completed, and
    wherein the guide component is configured to guide the syringe cover over a range that is greater than a distance between the needle insertion position and the needle withdrawal position.

2. The pharmaceutical syringe unit according to claim 1, wherein the syringe cover is inside the distal end cap, and the guide component has a stopper configured to prevent the syringe cover from coming loose from the distal end cap.

3. The pharmaceutical syringe unit according to claim 2, wherein the syringe cover has a guided part that is on an outer peripheral part of the syringe cover and is configured to be guided by the guide component of the distal end cap.

4. The pharmaceutical syringe unit according to claim 3, wherein the guide component is a riser on an inside of the distal end cap.

5. The pharmaceutical syringe unit according to claim 4, wherein the guided part is a flange.

6. The pharmaceutical syringe unit according to claim 5, wherein the riser is one of multiple risers,
wherein the flange is one of multiple flanges, and
wherein the flanges are sandwiched between the risers.

7. The pharmaceutical syringe unit according to claim 5, wherein the riser has a guide groove into which the flange is configured to fit.

8. The pharmaceutical syringe unit according to claim 7, wherein at least one of a front side of the guide groove and a rear side of the guide groove defines a stopper configured to prevent the syringe cover from coming loose from the distal end cap.

9. The pharmaceutical syringe unit according to claim 1, wherein the syringe cover has a holder configured to removably hold the pharmaceutical syringe.

10. The pharmaceutical syringe unit according to claim 1, wherein the syringe cover has:
a pharmaceutical syringe housing that is substantially cylindrical and configured to house the pharmaceutical syringe;
a piston insertion component on one end of the pharmaceutical syringe housing, the piston insertion component being configured to receive a piston configured to push the pharmaceutical out of the pharmaceutical syringe; and
a second engagement component that can be engaged with the pharmaceutical injection device main body.

11. A pharmaceutical injection device, comprising:
the pharmaceutical syringe unit according to claim 10;
a main body case, the pharmaceutical syringe unit being mounted to a front end side of the main body case;
the piston being inside the main body case; and
a driver configured to drive the piston forward and backward with respect to the main body case,
wherein the front end side of the main body case has:
a first engaged part configured to engage with the first engagement component of the distal end cap; and
a second engaged part configured to engage with the second engagement component of the syringe cover, the second engaged part being on a rear end side of the syringe cover.

12. The pharmaceutical syringe unit according to claim 1, to and from which an injection needle is attached and removed by an injection needle attachment and removal fixture, the injection needle attachment and removal fixture comprising a unit mounting component to which the pharmaceutical syringe unit is mounted, and a slide component configured to move the syringe cover to a front end side of a sliding range with respect to the distal end cap in order to mount the injection needle to the needle mounting component or to remove the injection needle mounted to the needle mounting component, the needle mounting component being on a front end side of the syringe cover of the pharmaceutical syringe unit,
wherein a distance that the syringe cover is configured to slide forward and backward with respect to the distal end cap is different:
(a) when the pharmaceutical syringe unit is mounted to the pharmaceutical injection device main body; and
(b) when the pharmaceutical syringe unit is mounted to the unit mounting component of the injection needle attachment and removal fixture.

13. The pharmaceutical syringe unit according to claim 12,
wherein the distance that the syringe cover is configured to slide forward and backward with respect to the distal end cap when the pharmaceutical syringe unit is mounted to the unit mounting component of the injection needle attachment and removal fixture is greater than the distance that the syringe cover is configured to slide forward and backward with respect to the distal end cap when the pharmaceutical syringe unit is mounted to the pharmaceutical injection device main body.

14. The pharmaceutical syringe unit according to claim 12,
wherein a position to which the slide component is configured to move the syringe cover to a front end side of the sliding range with respect to the distal end cap when the pharmaceutical syringe unit is mounted to the unit mounting component of the injection needle attachment and removal fixture, is on a front side of the needle insertion position when the pharmaceutical syringe unit is mounted to the pharmaceutical injection device main body.

15. The pharmaceutical syringe unit according to claim 1, wherein the guide component is a riser on an inside of the distal end cap.

16. An injection needle attachment and removal fixture, comprising a unit mounting component to which the pharmaceutical syringe unit according to claim 1 is mounted,
wherein a rear end side of the pharmaceutical syringe unit is on the unit mounting component.

17. The injection needle attachment and removal fixture according to claim 16,
further comprising a slide component configured to move the syringe cover to a front end side of a sliding range with respect to the distal end cap in order to mount the injection needle to the needle mounting component or to remove the injection needle that has been mounted to the needle mounting component, the needle mounting component being on a front end side of the syringe cover of the pharmaceutical syringe unit,
wherein the rear end side of the pharmaceutical syringe unit is on the unit mounting component, and a position of the syringe cover after being moved to the front end side by the slide component with respect to the distal end cap sticks out more to a front side than to the needle insertion position.

18. The injection needle attachment and removal fixture according to claim 17,
wherein the syringe cover of the pharmaceutical syringe unit is mounted to the unit mounting component and configured to move to the front end side when the slide component is moved to the front end side.

19. The injection needle attachment and removal fixture according to claim 17,
wherein the unit mounting component also serves as the slide component, and
when the pharmaceutical syringe unit is mounted to the unit mounting component, the syringe cover is configured to be pushed by a center portion of the unit mounting component and move to the front end side.

20. A storage case for storing the pharmaceutical syringe unit,
comprising the injection needle attachment and removal fixture according to claim 16.

* * * * *